(12) United States Patent
Seguin et al.

(10) Patent No.: US 8,579,966 B2
(45) Date of Patent: Nov. 12, 2013

(54) PROSTHETIC VALVE FOR TRANSLUMINAL DELIVERY

(75) Inventors: Jacques Seguin, Old Windsor (GB); Georg Börtlein, Meudon (FR)

(73) Assignee: Medtronic CoreValve LLC, Minneapolis, MN (US)

( * ) Notice: Subject to any disclaimer, the term of this patent is extended or adjusted under 35 U.S.C. 154(b) by 423 days.

(21) Appl. No.: 10/772,101

(22) Filed: Feb. 4, 2004

(65) Prior Publication Data

US 2004/0210304 A1  Oct. 21, 2004

Related U.S. Application Data

(63) Continuation-in-part of application No. 10/412,634, filed on Apr. 10, 2003, now Pat. No. 7,018,406, which is a continuation-in-part of application No. 10/130,355, filed as application No. PCT/FR00/03176 on Nov. 15, 2000, now Pat. No. 6,830,584, said application No. 10/412,634 is a continuation-in-part of application No. PCT/FR01/03258, filed on Oct. 19, 2001.

(51) Int. Cl.
    *A61F 2/24*  (2006.01)

(52) U.S. Cl.
    USPC .......................................... 623/2.18

(58) Field of Classification Search
    USPC ............................... 623/1.12–2.42
    See application file for complete search history.

(56) References Cited

U.S. PATENT DOCUMENTS

| 3,334,629 A | 8/1967 | Cohn |
| 3,409,013 A | 11/1968 | Berry |
| 3,540,431 A | 11/1970 | Mobin-Uddin |
| 3,587,115 A | 6/1971 | Shiley |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |

(Continued)

FOREIGN PATENT DOCUMENTS

| DE | 19532846 | 3/1997 |
| DE | 19546692 | 6/1997 |

(Continued)

OTHER PUBLICATIONS

*Balloon-Expandable Intracoronary Stent in the Adult Dog*; Schatz, Richard MD, et al.; *Laboratory Investigation—Myocardial Ischemia*; pp. 450-457; 1987.

(Continued)

*Primary Examiner* — David Isabella
*Assistant Examiner* — Ann Schillinger

(57) ABSTRACT

A prosthetic valve assembly for use in replacing a deficient native valve comprises a replacement valve supported on an expandable valve support. The valve support, which entirely supports the valve annulus, valve leaflets, and valve commissure points, is configured to be collapsible for transluminal delivery and expandable contact the anatomical annulus of the native valve when the assembly is properly positioned. Portions of the valve support may expand to a preset diameter to maintain coaptivity of the replacement valve and to prevent occlusion of the coronary ostia.

21 Claims, 42 Drawing Sheets

(56) References Cited

U.S. PATENT DOCUMENTS

| | | | |
|---|---|---|---|
| 3,795,246 A | 3/1974 | Sturgeon | |
| 3,839,741 A | 10/1974 | Haller | |
| 3,868,956 A | 3/1975 | Alfidi et al. | |
| 3,874,388 A | 4/1975 | King et al. | |
| 4,035,849 A | 7/1977 | Angell et al. | |
| 4,056,854 A | 11/1977 | Boretos et al. | |
| 4,106,129 A | 8/1978 | Carpentier et al. | |
| 4,222,126 A | 9/1980 | Boretos et al. | |
| 4,233,690 A | 11/1980 | Akins | |
| 4,265,694 A | 5/1981 | Boretos | |
| 4,291,420 A | 9/1981 | Reul | |
| 4,297,749 A | 11/1981 | Davis et al. | |
| 4,339,831 A | 7/1982 | Johnson | |
| 4,343,048 A | 8/1982 | Ross et al. | |
| 4,345,340 A | 8/1982 | Rosen | |
| 4,425,908 A | 1/1984 | Simon | |
| 4,470,157 A | 9/1984 | Love | |
| 4,501,030 A | 2/1985 | Lane | |
| 4,574,803 A | 3/1986 | Storz | |
| 4,580,568 A | 4/1986 | Gianturco | |
| 4,592,340 A | 6/1986 | Boyles | |
| 4,610,688 A | 9/1986 | Silvestrini et al. | |
| 4,612,011 A | 9/1986 | Kautzky | |
| 4,647,283 A | 3/1987 | Carpentier et al. | |
| 4,648,881 A | 3/1987 | Carpentier et al. | |
| 4,655,771 A | 4/1987 | Wallsten | |
| 4,662,885 A | 5/1987 | DiPisa, Jr. | |
| 4,665,906 A | 5/1987 | Jervis | |
| 4,681,908 A | 7/1987 | Broderick et al. | |
| 4,710,192 A | 12/1987 | Liotta et al. | |
| 4,733,665 A | 3/1988 | Palmaz | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |
| 4,819,751 A | 4/1989 | Shimada et al. | |
| 4,834,755 A | 5/1989 | Silvestrini et al. | |
| 4,856,516 A | 8/1989 | Hillstead | |
| 4,872,874 A | 10/1989 | Taheri | |
| 4,878,495 A | 11/1989 | Grayzel | |
| 4,878,906 A | 11/1989 | Lindemann et al. | |
| 4,883,458 A | 11/1989 | Shiber | |
| 4,909,252 A | 3/1990 | Goldberger | |
| 4,917,102 A | 4/1990 | Miller et al. | |
| 4,922,905 A | 5/1990 | Strecker | |
| 4,954,126 A | 9/1990 | Wallsten | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,002,559 A | 3/1991 | Tower | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Samuels | |
| 5,059,177 A | 10/1991 | Towne et al. | |
| 5,061,273 A | 10/1991 | Yock | |
| 5,085,635 A | 2/1992 | Cragg | |
| 5,089,015 A | 2/1992 | Ross | |
| 5,104,404 A * | 4/1992 | Wolff | 623/1.16 |
| 5,152,771 A | 10/1992 | Sabbaghian et al. | |
| 5,161,547 A | 11/1992 | Tower | |
| 5,163,953 A | 11/1992 | Vince | |
| 5,167,628 A | 12/1992 | Boyles | |
| 5,217,483 A | 6/1993 | Tower | |
| 5,232,445 A | 8/1993 | Bonzel | |
| 5,272,909 A | 12/1993 | Nguyen et al. | |
| 5,295,958 A | 3/1994 | Shturman | |
| 5,327,774 A | 7/1994 | Nguyen et al. | |
| 5,332,402 A | 7/1994 | Teitelbaum | |
| 5,350,398 A | 9/1994 | Pavcnik et al. | |
| 5,370,685 A | 12/1994 | Stevens | |
| 5,389,106 A | 2/1995 | Tower | |
| 5,397,351 A | 3/1995 | Pavcnik et al. | |
| 5,411,552 A * | 5/1995 | Andersen et al. | 623/2.18 |
| 5,415,633 A | 5/1995 | Lazarus et al. | |
| 5,431,676 A | 7/1995 | Dubrul et al. | |
| 5,443,446 A | 8/1995 | Shturman | |
| 5,480,424 A | 1/1996 | Cox | |
| 5,489,294 A | 2/1996 | McVenes et al. | |
| 5,489,297 A | 2/1996 | Duran | |
| 5,496,346 A | 3/1996 | Horzewski et al. | |
| 5,500,014 A | 3/1996 | Quijano et al. | |
| 5,507,767 A | 4/1996 | Maeda et al. | |
| 5,545,209 A | 8/1996 | Roberts et al. | |
| 5,545,211 A | 8/1996 | An et al. | |
| 5,545,214 A | 8/1996 | Stevens | |
| 5,554,185 A | 9/1996 | Block et al. | |
| 5,575,818 A | 11/1996 | Pinchuk | |
| 5,580,922 A | 12/1996 | Park et al. | |
| 5,591,195 A | 1/1997 | Taheri et al. | |
| 5,609,626 A | 3/1997 | Quijano et al. | |
| 5,645,559 A | 7/1997 | Hachtman et al. | |
| 5,665,115 A * | 9/1997 | Cragg | 623/1.13 |
| 5,667,523 A | 9/1997 | Bynon et al. | |
| 5,674,277 A | 10/1997 | Freitag | |
| 5,695,498 A | 12/1997 | Tower | |
| 5,702,368 A | 12/1997 | Stevens et al. | |
| 5,713,953 A | 2/1998 | Vallana et al. | |
| 5,716,417 A | 2/1998 | Girard et al. | |
| 5,749,890 A | 5/1998 | Shaknovich | |
| 5,766,151 A | 6/1998 | Valley et al. | |
| 5,782,809 A | 7/1998 | Umeno et al. | |
| 5,800,456 A | 9/1998 | Maeda et al. | |
| 5,800,508 A * | 9/1998 | Goicoechea et al. | 623/1.15 |
| 5,817,126 A | 10/1998 | Imran | |
| 5,824,041 A | 10/1998 | Lenker | |
| 5,824,043 A | 10/1998 | Cottone, Jr. | |
| 5,824,053 A | 10/1998 | Khosravi et al. | |
| 5,824,056 A | 10/1998 | Rosenberg | |
| 5,824,061 A | 10/1998 | Quijano et al. | |
| 5,824,064 A | 10/1998 | Taheri | |
| 5,840,081 A | 11/1998 | Andersen et al. | |
| 5,843,158 A * | 12/1998 | Lenker et al. | 623/1.13 |
| 5,855,597 A | 1/1999 | Jayaraman | |
| 5,855,601 A | 1/1999 | Bessler et al. | |
| 5,860,966 A | 1/1999 | Tower | |
| 5,861,028 A | 1/1999 | Angell | |
| 5,868,783 A | 2/1999 | Tower | |
| 5,876,448 A | 3/1999 | Thompson et al. | |
| 5,888,201 A | 3/1999 | Stinson et al. | |
| 5,891,191 A | 4/1999 | Stinson | |
| 5,906,619 A | 5/1999 | Olson et al. | |
| 5,907,893 A | 6/1999 | Zadno-Azizi et al. | |
| 5,913,842 A | 6/1999 | Boyd et al. | |
| 5,925,063 A | 7/1999 | Khosravi | |
| 5,944,738 A | 8/1999 | Amplatz et al. | |
| 5,954,766 A | 9/1999 | Zadno-Azizi et al. | |
| 5,957,949 A * | 9/1999 | Leonhardt et al. | 623/1.24 |
| 5,968,068 A | 10/1999 | Dehdashtian et al. | |
| 5,984,957 A | 11/1999 | Laptewicz, Jr. et al. | |
| 5,997,573 A | 12/1999 | Quijano et al. | |
| 6,022,370 A | 2/2000 | Tower | |
| 6,027,525 A | 2/2000 | Suh et al. | |
| 6,029,671 A | 2/2000 | Stevens et al. | |
| 6,042,589 A | 3/2000 | Marianne | |
| 6,042,598 A | 3/2000 | Tsugita et al. | |
| 6,051,014 A | 4/2000 | Jang | |
| 6,059,809 A | 5/2000 | Amor et al. | |
| 6,110,201 A | 8/2000 | Quijano et al. | |
| 6,146,366 A | 11/2000 | Schachar | |
| 6,159,239 A | 12/2000 | Greenhalgh | |
| 6,162,208 A | 12/2000 | Hipps | |
| 6,162,245 A | 12/2000 | Jayaraman | |
| 6,168,614 B1 | 1/2001 | Andersen et al. | |
| 6,171,335 B1 | 1/2001 | Wheatley et al. | |
| 6,200,336 B1 | 3/2001 | Pavcnik et al. | |
| 6,203,550 B1 | 3/2001 | Olson | |
| 6,210,408 B1 * | 4/2001 | Chandrasekaran et al. | 606/41 |
| 6,218,662 B1 | 4/2001 | Tchakarov et al. | |
| 6,221,006 B1 | 4/2001 | Dubrul et al. | |
| 6,221,091 B1 | 4/2001 | Khosravi | |
| 6,241,757 B1 | 6/2001 | An et al. | |

(56) References Cited

U.S. PATENT DOCUMENTS

| | | |
|---|---|---|
| 6,245,102 B1 | 6/2001 | Jayaraman |
| 6,258,114 B1 | 7/2001 | Konya et al. |
| 6,258,115 B1 | 7/2001 | Dubrul |
| 6,258,120 B1 | 7/2001 | McKenzie et al. |
| 6,264,691 B1 * | 7/2001 | Gabbay ................... 623/2.14 |
| 6,277,555 B1 | 8/2001 | Duran et al. |
| 6,299,637 B1 * | 10/2001 | Shaolian et al. ............ 623/1.24 |
| 6,302,906 B1 | 10/2001 | Goicoechea et al. |
| 6,305,436 B1 * | 10/2001 | Andersen et al. ............ 140/107 |
| 6,309,382 B1 | 10/2001 | Garrison et al. |
| 6,309,417 B1 | 10/2001 | Spence et al. |
| 6,327,772 B1 | 12/2001 | Zadno-Azizi et al. |
| 6,338,735 B1 | 1/2002 | Stevens |
| 6,348,063 B1 | 2/2002 | Yassour et al. |
| 6,350,277 B1 * | 2/2002 | Kocur ..................... 623/1.11 |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 * | 8/2002 | DiMatteo et al. ............ 623/1.24 |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,031 B2 * | 5/2003 | Chandrasekaran et al. .... 606/41 |
| 6,562,058 B2 | 5/2003 | Seguin et al. |
| 6,569,196 B1 | 5/2003 | Vesely |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 * | 9/2003 | Gilligan et al. ............. 623/1.12 |
| 6,622,604 B1 | 9/2003 | Chouinard et al. |
| 6,632,243 B1 | 10/2003 | Zadno-Azizi et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon et al. |
| 6,790,229 B1 | 9/2004 | Berreklouw |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,115,141 B2 | 10/2006 | Menz et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,374,571 B2 | 5/2008 | Pease et al. |
| 7,381,218 B2 | 6/2008 | Schreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,556,646 B2 | 7/2009 | Yang et al. |
| 2001/0001314 A1 * | 5/2001 | Davison et al. ................. 606/41 |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 * | 8/2001 | Drasler et al. ............... 623/1.24 |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 * | 11/2001 | Pinchuk et al. .............. 623/1.13 |
| 2002/0010508 A1 * | 1/2002 | Chobotov .................. 623/1.44 |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 * | 3/2002 | Heath ..................... 623/1.15 |
| 2002/0042650 A1 * | 4/2002 | Vardi et al. ................. 623/1.35 |
| 2002/0042651 A1 | 4/2002 | Liddicoat et al. |
| 2002/0052651 A1 | 5/2002 | Myers et al. |
| 2002/0058995 A1 * | 5/2002 | Stevens .................... 623/2.11 |
| 2002/0072789 A1 | 6/2002 | Hackett et al. |

(56) References Cited

U.S. PATENT DOCUMENTS

| | | |
|---|---|---|
| 2002/0095209 A1 | 7/2002 | Zadno-Azizi et al. |
| 2002/0099439 A1* | 7/2002 | Schwartz et al. ............ 623/1.24 |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1* | 9/2002 | Snyders ....................... 623/2.18 |
| 2002/0133183 A1* | 9/2002 | Lentz et al. .................. 606/155 |
| 2002/0138138 A1 | 9/2002 | Yang |
| 2002/0151970 A1* | 10/2002 | Garrison et al. ............. 623/2.11 |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1* | 1/2003 | Cribier ......................... 623/2.11 |
| 2003/0023300 A1* | 1/2003 | Bailey et al. ................. 623/1.13 |
| 2003/0023303 A1* | 1/2003 | Palmaz et al. ................ 623/2.18 |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040792 A1* | 2/2003 | Gabbay ........................ 623/2.11 |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0069636 A1* | 4/2003 | Solem et al. ................. 623/2.37 |
| 2003/0109924 A1* | 6/2003 | Cribier ......................... 623/2.18 |
| 2003/0125795 A1 | 7/2003 | Pavcnik et al. |
| 2003/0130726 A1* | 7/2003 | Thorpe et al. ................ 623/1.24 |
| 2003/0130729 A1* | 7/2003 | Paniagua et al. ............. 623/2.11 |
| 2003/0139804 A1* | 7/2003 | Hankh et al. ................. 623/1.22 |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1* | 10/2003 | Lombardi et al. ............ 623/1.13 |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0199972 A1 | 10/2003 | Zadno-Azizi et al. |
| 2003/0212410 A1 | 11/2003 | Stenzel et al. |
| 2003/0212452 A1 | 11/2003 | Zadno-Azizi et al. |
| 2003/0212454 A1 | 11/2003 | Scott et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0093005 A1 | 5/2004 | Durcan |
| 2004/0093060 A1 | 5/2004 | Seguin et al. |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1* | 5/2005 | Kato ............................. 600/585 |
| 2005/0096692 A1 | 5/2005 | Linder et al. |
| 2005/0096724 A1 | 5/2005 | Stenzel et al. |
| 2005/0096727 A1* | 5/2005 | Allen et al. .................. 623/1.15 |
| 2005/0096734 A1 | 5/2005 | Majercak et al. |
| 2005/0096735 A1* | 5/2005 | Hojeibane et al. ........... 623/1.24 |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Berheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143809 A1 | 6/2005 | Salahieh |
| 2005/0148997 A1 | 7/2005 | Valley et al. |
| 2005/0165477 A1 | 7/2005 | Anduiza et al. |
| 2005/0187616 A1 | 8/2005 | Realyvasquez |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoefer et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |

(56) References Cited

U.S. PATENT DOCUMENTS

| | | |
|---|---|---|
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0043435 A1 | 2/2007 | Seguin et al. |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0138079 A1 | 5/2009 | Tuval et al. |
| 2009/0164004 A1 | 6/2009 | Cohn |
| 2009/0171447 A1 | 7/2009 | VonSegesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0240264 A1 | 9/2009 | Tuval et al. |
| 2009/0240320 A1 | 9/2009 | Tuval |

FOREIGN PATENT DOCUMENTS

| | | |
|---|---|---|
| DE | 19857887 | 7/2000 |
| DE | 19907646 | 8/2000 |
| DE | 100 48 814 | 9/2000 |
| DE | 10049812 | 4/2002 |
| DE | 10049813 | 4/2002 |
| DE | 10049814 | 4/2002 |
| DE | 10049815 | 4/2002 |
| EP | 0103546 | 3/1984 |
| EP | 0103546 A1 | 3/1984 |
| EP | 0103546 B1 | 3/1984 |
| EP | 0597967 | 12/1994 |
| EP | 0850607 | 7/1998 |
| EP | 1057459 A1 | 6/2000 |
| EP | 1057460 | 12/2000 |
| EP | 1088529 | 4/2001 |
| EP | 1255510 | 11/2002 |
| EP | 0937439 B1 | 9/2003 |
| EP | 1340473 | 9/2003 |
| EP | 0819013 | 6/2004 |
| FR | 2788217 | 7/2000 |
| GB | 2056023 | 3/1981 |
| GB | 2433700 | 12/2007 |
| SU | 1271508 A1 | 11/1986 |
| WO | WO 91/17720 | 11/1991 |
| WO | WO 92/17118 | 10/1992 |
| WO | WO 93/01768 | 2/1993 |
| WO | 95/29640 | 11/1995 |
| WO | 98/14137 | 4/1998 |
| WO | WO 98/29057 | 7/1998 |
| WO | WO 99/33414 | 7/1999 |
| WO | WO 00/41652 | 7/2000 |
| WO | 00/44313 | 8/2000 |
| WO | 00/47136 | 8/2000 |
| WO | WO 00/47139 | 8/2000 |
| WO | 01/35870 | 5/2001 |
| WO | WO 01/49213 | 7/2001 |
| WO | WO 01/54625 | 8/2001 |
| WO | WO 01/62189 | 8/2001 |
| WO | WO 01/64137 | 9/2001 |
| WO | 01/76510 | 10/2001 |
| WO | WO 01/76510 | 10/2001 |
| WO | 02/22054 | 3/2002 |
| WO | 02/36048 | 5/2002 |
| WO | WO 02/22054 | 5/2002 |
| WO | WO 02/41789 | 5/2002 |
| WO | 02/49540 | 6/2002 |
| WO | WO 02/43620 | 6/2002 |
| WO | WO 02/47575 | 6/2002 |

(56) References Cited

FOREIGN PATENT DOCUMENTS

| | | |
|---|---|---|
| WO | WO 02/49540 | 6/2002 |
| WO | 03/003943 | 1/2003 |
| WO | 03/003949 | 1/2003 |
| WO | 03/011195 | 2/2003 |
| WO | 03/028592 | 4/2003 |
| WO | 03/030776 | 4/2003 |
| WO | 2004/019811 | 3/2004 |
| WO | 2004/019825 | 3/2004 |
| WO | 2004/023980 | 3/2004 |
| WO | 2004/041126 | 5/2004 |
| WO | 2004/058106 | 7/2004 |
| WO | 2004/089250 | 10/2004 |
| WO | WO 2004/096100 A1 | 11/2004 |
| WO | 2005/004753 | 1/2005 |
| WO | 2005/027790 | 3/2005 |
| WO | 2005/046528 | 5/2005 |
| WO | 2008/047354 | 4/2008 |
| WO | 2008/100599 | 8/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | 2009/061389 | 5/2009 |
| WO | 2009/091509 | 7/2009 |

OTHER PUBLICATIONS

U.S. Appl. No. 12/250,163, filed Oct. 13, 2008.
U.S. Appl. No. 61/192,199, filed Sep. 15, 2008.
U.S. Appl. No. 12/253,858, filed Oct. 17, 2008.
U.S. Appl. No. 12/596,343, filed Apr. 14, 2008.
U.S. Appl. No. 61/129,170, filed Jun. 9, 2008.
Andersen, H.R. et al, "Transluminal implantation of artificial heart valves. Description of a new expandable aortic valve and initial results with implantation by catheter technique in closed chest pigs." Euro. Heart J. (1992) 13:704-708.
Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.
Bailey, "Percutaneous Expandable Prosthetic Valves," In: Topol EJ, ed. Textbook of Interventional Cardiology. Volume II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Insertion of the Pulmonary Valve," Journal of the American College of Cardiology (United States), May 15, 2002, pp. 1664-1669.
Bonhoeffer, et al, "Percutaneous Mitral Valve Dilatation with the Multi-Track System," Catheterization and Cardiovascular Interventions—Official Journal of the Society for Cardiac Angiography & Interventions (United States), Oct. 1999, pp. 178-183.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Technique and Results of Percutaneous Mitral Valvuloplasty With the Multi-Track System," Journal of Interventional Cardiology (United States), 200, pp. 263-268.
Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Images in Cardiovascular Medicine. Percutaneous Aortic Valve Replacement in Animals," Circulation (United States), Mar. 16, 2004, 109, p. el61.
Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.
Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Closure of a Paravalvular Mitral Regurgitation with Amplatzer and Coil Prostheses," Archives des Maladies du Coeur Et Des Vaisseaux (France), May 2002, pp. 483-486.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Implantation of a Valve in the Descending Aorta in Lambs," European Heart Journal (England), Jul. 2002, pp. 1045-1049.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Hanzel, et al., "Complications of percutaneous aortic valve replacement: experience with the Criber-Edwards™ percutaneous heart valve," EuroIntervention Supplements (2006), 1 (Supplement A) A3-A8.
Huber, et al., "Do Valved Stents Compromise Coronary Flow?" Eur. J. Cardiothorac. Surg. 2004;25:754-759.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al., "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Khambadkone, et al, "Percutaneous Pulmonary Valve Implantation: Impact of Morphology on Case Selection," Circulation 108 (17 Supplement), Oct. 28, 2003, p. IV-642-IV-643.
Lutter, et al, "Percutaneous Aortic Valve Replacement: An Experimental Study. 1. Studies on Implantation," The Journal of Thoracic and Cardiovascular Surgery, Apr. 2002 pp. 768-776.

(56) References Cited

OTHER PUBLICATIONS

Lutter, et al, "Percutaneous Valve Replacement: Current State and Future Prospects," Annals of Thoracic Surgery (Netherlands), Dec. 2004, pp. 2199-2206.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Webb, et al., "Percutaneous Aortic Valve Implantation Retrograde from the Femoral Artery," Circulation (2006), 113;842-850.
Yonga, et al, "Effect of Percutaneous Balloon Mitral Valvotomy on Pulmonary Venous Flow in Severe Mitral Stenosis," East African Medical Journal (Kenya), Jan. 1999, pp. 28-30.
Yonga, et al, "Percutaneous Balloon Mitral Valvotomy: Initial Experience in Nairobi Using a New Multi-Track Catheter System," East African Medical Journal (Kenya), Feb. 1999, pp. 71-74.
Yonga, et al, "Percutaneous Transluminal Balloon Valvuloplasty for Pulmonary Valve Stenosis: Report on Six Cases," East African Medical Journal (Kenya), Apr. 1994, pp. 232-235.
Yonga, et al, "Percutaneous Transvenous Mitral Commissurotomy in Juvenile Mitral Stenosis," East African Medical Journal (Kenya), Apr. 2003, pp. 172-174.
Commeau et al, "Percutaneous balloon dilatation of calcific aortic valve stenosis: anatomical and haemodynamic evaluation," 1988, British Heart Journal, 59:227-238.
Stassano et al., "Mid-term results of the valve-on-valve technique for bioprosthetic failure," Eur. J. Cardiothorac. Surg. 2000; 18:453-457.
Expert report of Dr. Nigel Buller, dated Jan. 12, 2009, Edwards' United Kingdom action for invalidity, Claim No. HC 08CO0934.
Expert report of Dr. Nigel Buller, non-confidential annex—infringement, dated Jan. 12, 2009, Edwards' United Kingdom action for invalidity, Claim No. HC 08CO0934.
Expert report of Dr. Rodolfo Quijano, dated Jan. 9, 2009, Edwards' United Kingdom action for invalidity, Claim No. HC 08CO0934.
First Expert report of Prof. David Williams, dated Jan. 12, 2009, Edwards' United Kingdom action for invalidity, Claim No. HC 08CO0934.
First Expert report of Prof. Martin Rothman, dated Jan. 12, 2009, Edwards' United Kingdom action for invalidity, Claim No. HC 08CO0934.
Fourth Expert report of Prof. Martin Rothman, dated Apr. 22, 2009, Edwards' United Kingdom action for invalidity, Claim No. HC 08CO0934.
Second Expert report of Dr. Nigel Buller, dated Feb. 25, 2009, Edwards' United Kingdom action for invalidity, Claim No. HC 08CO0934.
Second Expert report of Dr. Rodolfo Quijano, dated Feb. 26, 2009, Edwards' United Kingdom action for invalidity, Claim No. HC 08CO0934.
Second Expert report of Prof. David Williams, dated Feb. 5, 2009, Edwards' United Kingdom action for invalidity, Claim No. HC 08CO0934.
Second Expert report of Prof. Martin Rothman, dated Feb. 5, 2009, Edwards' United Kingdom action for invalidity, Claim No. HC 08CO0934.
Third Expert report of Dr. Nigel Buller, dated Apr. 21, 2009, Edwards' United Kingdom action for invalidity, Claim No. HC 08CO0934.
Third Expert report of Dr. Rudolfo Quijano, dated Apr. 27, 2009, Edwards' United Kingdom action for invalidity, Claim No. HC 08CO0934.
Third Expert report of Prof. David Williams, dated Apr. 22, 2009, Edwards' United Kingdom action for invalidity, Claim No. HC 08CO0934.
Pavcnik et al., "Aortic and venous valve for percutaneous insertion," Min. Invas. Ther. & Allied Techol. 2000, vol. 9, pp. 287-292.
First Expert report of Dr. Nigel Person Buller (30 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Second Expert report of Dr. Nigel Person Buller (5 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Drawing by Dr. Buller (Edwards Expert) of his interpretation of the "higher stent" referred to at col. 8, lines 13-222 of Andersen EP 592410B1 (1 page), *Corevalve, Inc. v. Edwards Lifesciences AG and Edwards Lifesciences PVT, Inc.*, High Court of Justice—Chancery Division Patents Court, United Kingdom, Case No. HC-07-C01243.
Drawing by Dr. Buller (Edwards Expert) of "higher stent" on the schematic representation of the aortic valve area set out in Figure 2 of Rothman's first expert report (1 page), *Corevalve, Inc. v. Edwards Lifesciences AG and Edwards Lifesciences PVT, Inc.*, High Court of Justice—Chancery Division Patents Court, United Kingdom, Case No. HC-07-C01243.
First Expert report of Professor John R. Pepper (20 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Second Expert report of Professor John R. Pepper (3 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
First Expert report of Dr. Anthony C. Lunn (7 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
First Witness statement of Stanton Rowe (9 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Second Witness statement of Stanton Rowe (3 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
PVT slides naming Alain Cribier, Martin Leon, Stan Rabinovich and Stanton Rowe (16 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
First Expert report of Professor Martin Terry Rothman (75 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Reply Expert report of Professor Martin Terry Rothman (9 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
First Expert report of Richard A. Hillstead (41 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Reply Expert report of Richard A. Hillstead (9 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.

\* cited by examiner

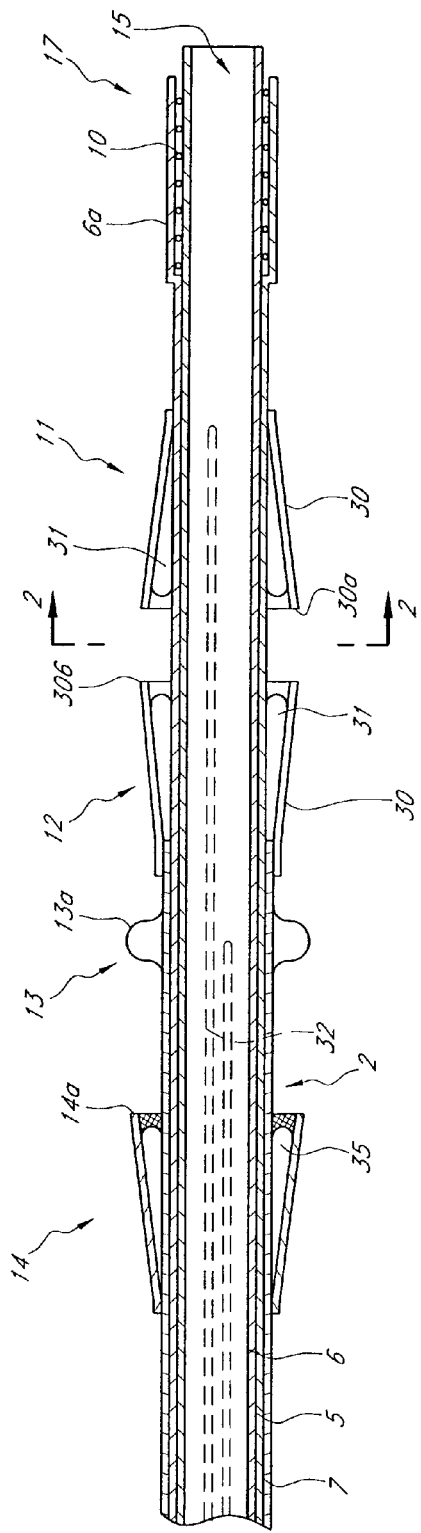
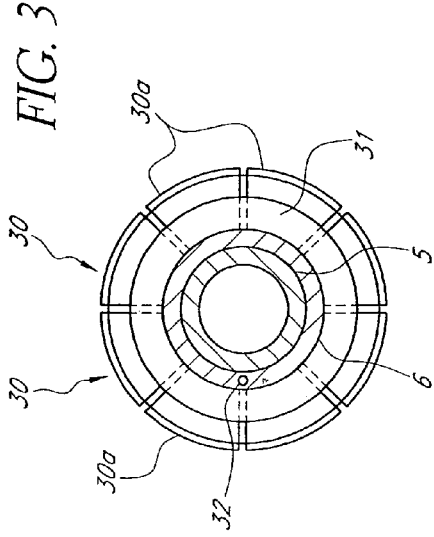
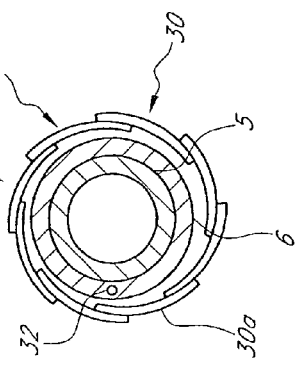

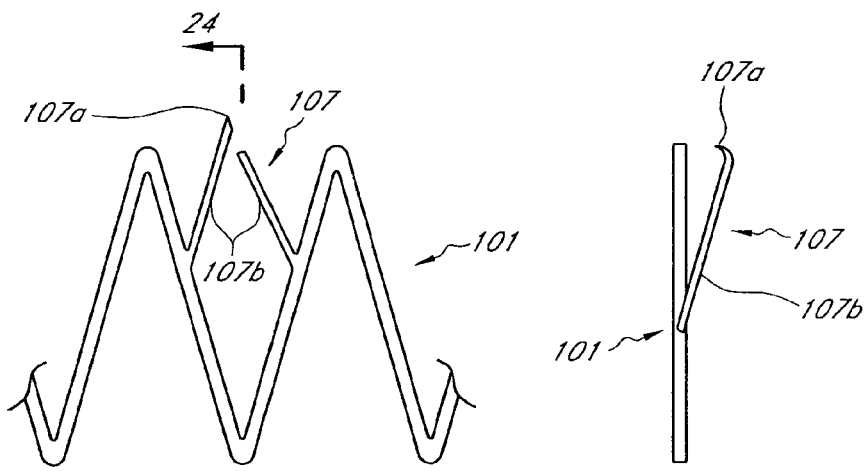
FIG. 23
FIG. 24
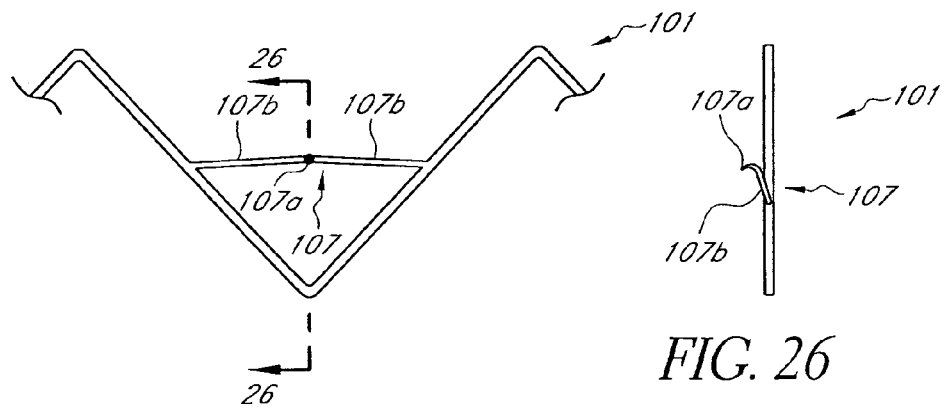
FIG. 25
FIG. 26
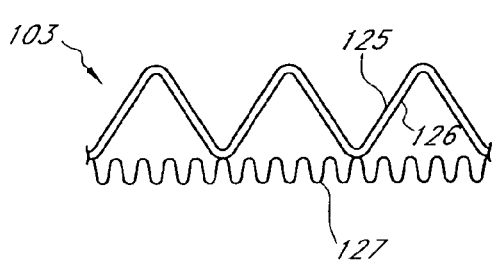
FIG. 27
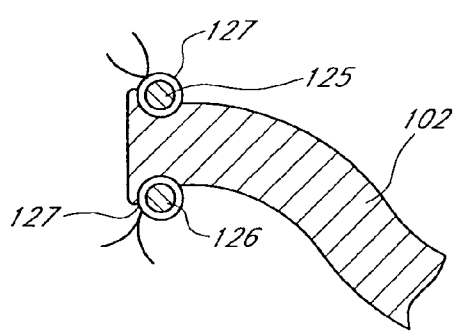
FIG. 28

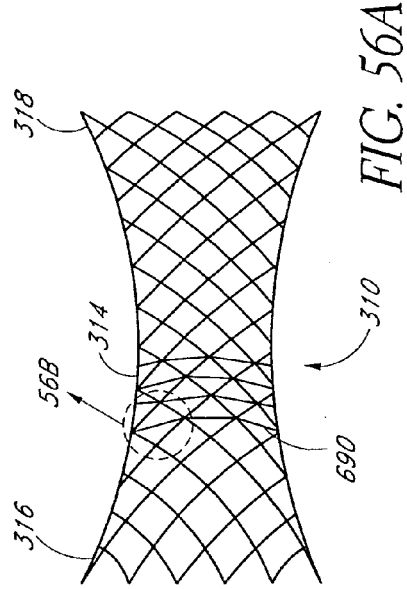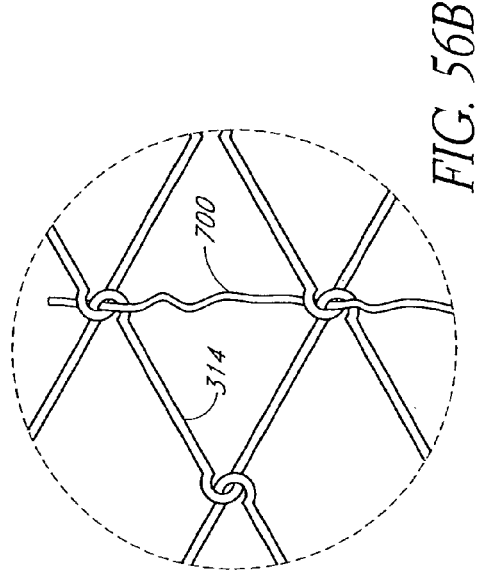

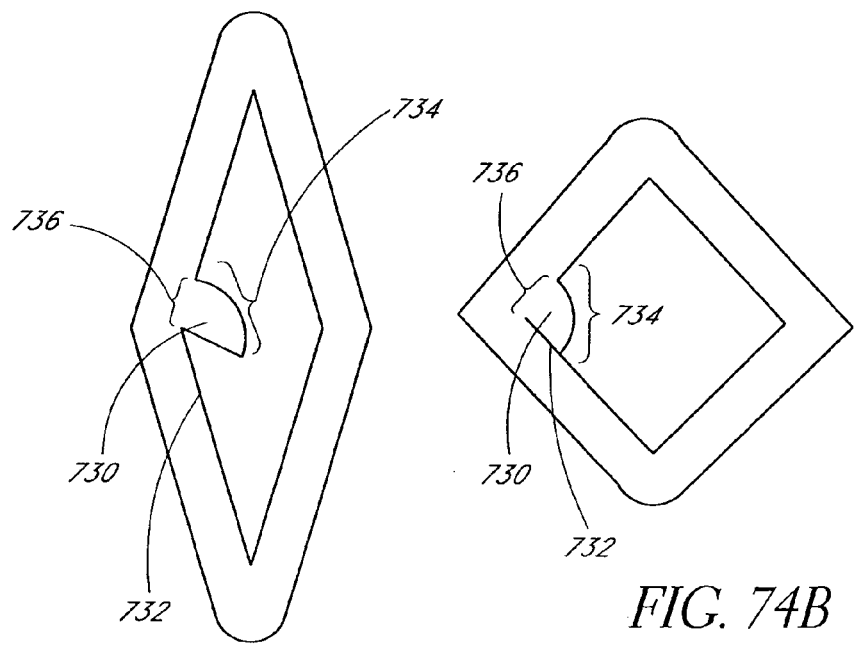
FIG. 74A
FIG. 74B
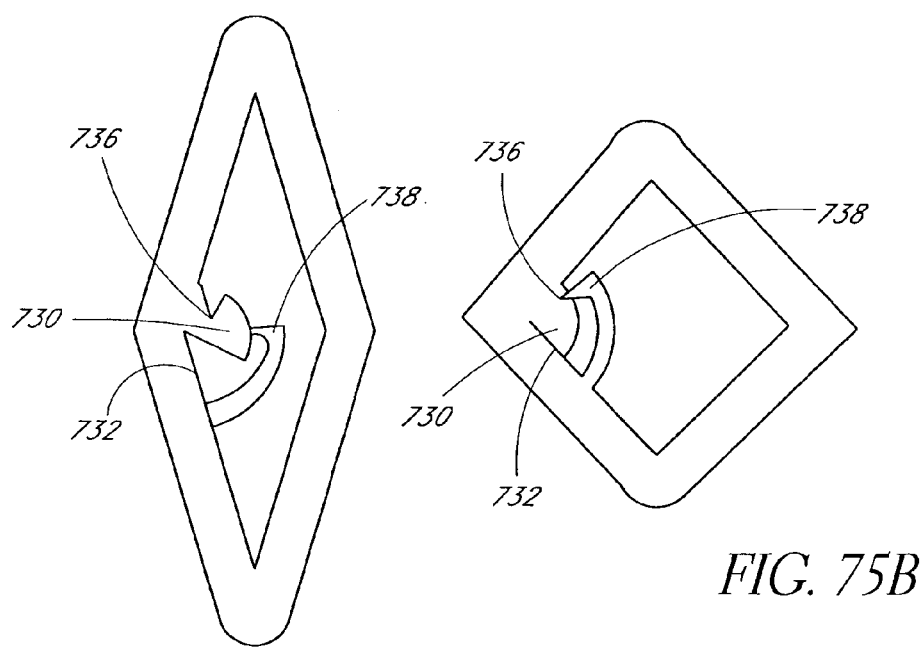
FIG. 75A
FIG. 75B

PROSTHETIC VALVE FOR TRANSLUMINAL DELIVERY

CROSS-REFERENCE TO RELATED APPLICATIONS

The present application is a continuation-in-part of U.S. Ser. No. 10/412,634 filed on Apr. 10, 2003, which is (1) a continuation-in-part of U.S. Ser. No. 10/130,355 filed on May 17, 2002, which is the U.S. national phase under §371 of International Application No. PCT/FR00/03176, filed on Nov. 15, 2000, which was published in a language other than English and which claimed priority from French Application No. 99/14462 filed on Nov. 17, 1999, now French Patent No. 2,800,984, and (2) also a continuation-in-part of International Application No. PCT/FR01/03258 filed on Oct. 19, 2001, which was published in a language other than English and which claimed priority from French Application No. 00/14028 filed on Oct. 31, 2000, now French Patent No. 2,815,844.

FIELD OF THE INVENTION

The present invention relates to a prosthetic cardiac valve and related deployment system that can be delivered percutaneously through the vasculature, and a method for delivering same.

BACKGROUND OF THE INVENTION

Currently, the replacement of a deficient cardiac valve is often performed by opening the thorax, placing the patient under extracorporeal circulation or peripheral aorto-venous heart assistance, temporarily stopping the heart, surgically opening the heart, excising the deficient valve, and then implanting a prosthetic valve in its place. U.S. Pat. No. 4,106,129 to Carpentier describes a bioprosthetic heart valve with compliant orifice ring for surgical implantation. This procedure generally requires prolonged patient hospitalization, as well as extensive and often painful recovery. It also presents advanced complexities and significant costs.

To address the risks associated with open heart implantation, devices and methods for replacing a cardiac valve by a less invasive means have been contemplated. For example, French Patent Application No. 99 14462 illustrates a technique and a device for the ablation of a deficient heart valve by percutaneous route, with a peripheral valvular approach. International Application (PCT) Nos. WO 93/01768 and WO 97/28807, as well as U.S. Pat. No. 5,814,097 to Sterman et al., U.S. Pat. No. 5,370,685 to Stevens, and U.S. Pat. No. 5,545,214 to Stevens illustrate techniques that are not very invasive as well as instruments for implementation of these techniques.

U.S. Pat. No. 3,671,979 to Moulopoulos and U.S. Pat. No. 4,056,854 to Boretos describe a catheter-mounted artificial heart valve for implantation in close proximity to a defective heart valve. Both of these prostheses are temporary in nature and require continued connection to the catheter for subsequent repositioning or removal of the valve prosthesis, or for subsequent valve activation.

With regard to the positioning of a replacement heart valve, attaching this valve on a support with a structure in the form of a wire or network of wires, currently called a stent, has been proposed. This stent support can be contracted radially in such a way that it can be introduced into the body of the patient percutaneously by means of a catheter, and it can be deployed so as to be radially expanded once it is positioned at the desired target site. U.S. Pat. No. 3,657,744 to Ersek discloses a cylindrical, stent-supported, tri-leaflet, tissue, heart valve that can be delivered through a portion of the vasculature using an elongate tool. The stent is mounted onto the expansion tool prior to delivery to the target location where the stent and valve are expanded into place. More recently, U.S. Pat. No. 5,411,552 to Andersen also illustrates a technique of this type. In the Andersen patent, a stent-supported tissue valve is deliverable percutaneously to the native heart valve site for deployment using a balloon or other expanding device. Efforts have been made to develop a stent-supported valve that is self-expandable, using memory materials such as Nitinol.

The stent-supported systems designed for the positioning of a heart valve introduce uncertainties of varying degree with regard to minimizing migration from the target valve site. A cardiac valve that is not adequately anchored in place to resist the forces of the constantly changing vessel wall diameter, and turbulent blood flow therethrough, may dislodge itself, or otherwise become ineffective. In particular, the known stents do not appear to be suited to sites in which the cardiac wall widens on either proximally and/or distally of the valve annulus situs. Furthermore, the native cardiac ring remaining after ablation of the native valve can hinder the positioning of these stents. These known systems also in certain cases create problems related to the sealing quality of the replacement valve. In effect, the existing cardiac ring can have a surface that is to varying degrees irregular and calcified, which not only lessens the quality of the support of the stent against this ring but also acts as the source of leaks between the valve and this ring. Also, these systems can no longer be moved at all after deployment of the support, even if their position is not optimal. Furthermore, inflating a balloon on a stented valve as described by Andersen may traumatize the valve, especially if the valve is made from a fragile material as a living or former living tissue.

Also, the existing techniques are however considered not completely satisfactory and capable of being improved. In particular, some of these techniques have the problem of involving in any case putting the patient under extracorporeal circulation or peripheral aorto-venous heart assistance and temporary stopping of the heart; they are difficult to put into practice; they do not allow precise control of the diameter according to which the natural valve is cut, in view of the later calibration of the prosthetic valve; they lead to risks of diffusion of natural valve fragments, often calcified, into the organism, which can lead to an embolism, as well as to risks of perforation of the aortic or cardiac wall; they moreover induce risks of acute reflux of blood during ablation of the natural valve and risk of obstruction of blood flow during implantation of the device with a balloon expandable stent for example.

SUMMARY OF THE INVENTION

The object of the present invention is to transluminally provide a prosthetic valve assembly that includes features for preventing substantial migration of the prosthetic valve assembly once delivered to a desired location within a body. The present invention aims to remedy these significant problems. Another objective of the invention is to provide a support at the time of positioning of the replacement valve that makes it possible to eliminate the problem caused by the native valve sheets, which are naturally calcified, thickened and indurated, or by the residues of the valve sheets after valve resection. Yet another objective of the invention is to provide a support making possible complete sealing of the replacement valve, even in case of an existing cardiac ring which has a surface which is to varying degrees irregular and/or to varying degrees calcified. Another objective of the invention is to have a device that can adapt itself to the local anatomy (i.e. varying diameters of the ring, the subannular zone, the sino-tubular junction) and maintain a known diameter of the valve prosthesis to optimize function and durability. The invention also has the objective of providing a support whose position can be adapted and/or corrected if necessary at the time of implantation.

The present invention is a prosthesis comprising a tissue valve supported on a self-expandable stent in the form of a wire or a plurality of wires that can be contracted radially in order to make possible the introduction of the support-valve assembly into the body of the patient by means of a catheter, and which can be deployed in order to allow this structure to engage the wall of the site where the valve is to be deployed. In one embodiment, the valve is supported entirely within a central, self-expandable, band. The prosthetic valve assembly also includes proximal and distal anchors. In one embodiment, the anchors comprise discrete self-expandable bands connected to the central band so that the entire assembly expands in unison into place to conform more naturally to the anatomy.

The valve can be made from a biological material, such as an animal or human valve or tissue, or from a synthetic material, such as a polymer, and includes an annulus, leaflets and commissure points. The valve is attached to the valve support band with, for example, a suture. The suture can be a biologically compatible thread, plastic, metal or adhesive, such as cyanoacrylate. In one embodiment, the valve support band is made from a single wire bent in a zigzag manner to form a cylinder. Alternatively, the valve support band can be made from a plurality of wires interwoven with one another. The wire can be made from stainless steel, silver, tantalum, gold, titanium, or any suitable tissue or biologically compatible plastic, such as ePTFE or Teflon. The valve support band may have a loop at its ends so that the valve support band can be attached to an upper anchor band at its upper end, and a lower anchor band at its lower end. The link can be made from, for example, stainless steel, silver, tantalum, gold, titanium, any suitable plastic material, or suture.

The prosthetic valve assembly is compressible about its center axis such that its diameter can be decreased from an expanded position to a compressed position. The prosthetic valve assembly may be loaded onto a catheter in its compressed position, and so held in place. Once loaded onto the catheter and secured in the compressed position, the prosthetic valve assembly can be transluminally delivered to a desired location within a body, such as a deficient valve within the heart. Once properly positioned within the body, the catheter can be manipulated to release the prosthetic valve assembly and permit it to into its expanded position. In one embodiment, the catheter includes adjustment hooks such that the prosthetic valve assembly may be partially released and expanded within the body and moved or otherwise adjusted to a final desired location. At the final desired location, the prosthetic valve assembly may be totally released from the catheter and expanded to its fully expanded position. Once the prosthetic valve assembly is fully released from the catheter and expanded, the catheter may be removed from the body.

Other embodiments are contemplated. In one such alternative embodiment, this structure comprises an axial valve support portion that has a structure in the form of a wire or in the form of a network of wires suitable for receiving the replacement valve mounted on it, and suitable for supporting the cardiac ring remaining after the removal of the deficient native valve. The embodiment may further comprise at least one axial wedging portion, that has a structure in the form of a wire or in the form of a network of wires that is distinct from the structure of said axial valve support portion, and of which at least a part has, when deployed a diameter greater or smaller than that of said deployed axial valve support portion, such that this axial wedging portion or anchor is suitable for supporting the wall bordering said existing cardiac ring. The embodiment preferably further comprises at least one wire for connecting the two portions, the wire or wires being connected at points to these portions in such a way as not to obstruct the deployment of said axial portions according to their respective diameters. The embodiment thus provides a support in the form of at least two axial portions that are individualized with respect to one another with regard to their structure, and that are connected in a localized manner by at least one wire; where this wire or these wires do not obstruct the variable deployment of the axial portion with the valve and of the axial wedging portion(s) or anchors. The anchors may be positioned distally or proximally.

The presence of a structure in the form of a wire or in the form of a network of wires in the axial valve support portion makes possible a perfect assembly of this valve with this structure, and the shape as well as the diameter of this axial portion can be adapted for supporting the existing cardiac ring under the best conditions. In particular, this axial valve support portion can have a radial force of expansion such that it pushes back ("impacts") the valve sheets that are naturally calcified or the residues of the valve sheets after valve resection onto or into the underlying tissues, so that these elements do not constitute a hindrance to the positioning of the replacement valve and also allow for a greater orifice area. This structure also makes it possible to support an optional anchoring means and/or optional sealing means for sealing the space between the existing cardiac ring and the replacement valve, as indicated below.

The configuration of each anchor portion can be adapted for supporting the cardiac wall situated at the approach to the existing cardiac ring under the best conditions. In particular, this anchor portion can have a tubular shape with a constant diameter greater than that of the axial valve support portion, or the form of a truncated cone whose diameter increases with distance from the axial valve support portion. By attaching at least one anchor portion to the axial valve support portion, the prosthetic valve assembly assumes a non-cylindrical or toroidal configuration. This non-cylindrical configuration provides an increased radial expansion force and increased diameter at both ends of the prosthetic valve assembly that may tighten the fit between the valve assembly and surrounding tissue structures. The tighter fit from a non-cylindrical configuration can favorably increase the anchoring and sealing characteristics of the prosthesis. The axial valve support portion itself may be non-cylindrical as well.

Preferably, the tubular support has an axial valve support portion in the form of at least two parts, of which at least one is suitable for supporting the valve and of which at least another is suitable for pushing back the native valve sheets or the residues of the native valve sheets after valve resection, into or onto the adjacent tissue in order to make this region able to receive the tubular support. This axial valve support portion eliminates the problem generated by these valve or cardiac ring elements at the time of positioning of the replacement valve. The radial force of this axial valve support portion, by impacting all or part of the valvular tissue or in the wall or its vicinity in effect ensures a more regular surface more capable of receiving the valve support axis. It also ensures a better connection with the wall while reducing the risk of peri-prosthetic leakage. Furthermore, such a structure permits the valve to maintain a diameter within a preset range to ensure substantial coaptivity and avoid significant leakage.

The particular method of maintaining the valve diameter within a preset range described above relates to the general concept of controlling the expanded diameter of the prosthesis. The diameter attained by a portion of the prosthesis is a function of the radial inward forces and the radial expansion forces acting upon that portion of the prosthesis. A portion of the prosthesis will reach its final diameter when the net sum of these forces is equal to zero. Thus, controlling the diameter of the prosthesis can be addressed by addressing the radial expansion force, the radial inward forces, or a combination of both. Changes to the radial expansion force generally occur in a diameter-dependent manner and can occur extrinsically or intrinsically. Resisting further expansion can occur extrinsically by using structural restraints that oppose the intrinsic radial expansion force of the prosthesis, or intrinsically by changing the expansion force so that it does not expand beyond a preset diameter. The first way, referred to previously, relates to controlling expansion extrinsically to a preset diameter to ensure coaptivity. In one embodiment configured to control diameter, a maximum diameter of at least a portion of the support structure may be ensured by a radial restraint provided along at least a portion of circumference of the support structure. The radial restraint may comprise a wire, thread or cuff engaging the support structure. The restraint may be attached to the support structure by knots, sutures or adhesives, or may be integrally formed with the support structure. The radial restraints may also be integrally formed with the support structure during the manufacturing of the support structure. The configuration of the radial restraint would depend upon the restraining forces necessary and the particular stent structure used for the prosthesis. A radial restraint comprising a mechanical stop system is also contemplated. A mechanical stop system uses the inverse relationship between the circumference of the support structure and the length of the support structure. As the support structure radially expands, the longitudinal length of the support structure will generally contract or compress as the wires of the support structure having a generally longitudinal orientation change to a circumferential orientation during radial expansion. By limiting the distance by which the support structure can compress in a longitudinal direction, or the angle to which the support structure wires reorient, radial expansion in turn can be limited to a maximum diameter. The radial restraint may comprise a plurality of protrusions on the support structure where the protrusions abut or form a mechanical stop against another portion of the support structure when the support structure is expanded to the desired diameter.

In an embodiment configured to control the expanded diameter intrinsically for a portion of the support, the radial expansion force of the valve support may be configured to apply up to a preset diameter. This can be achieved by the use of the shape memory effect of certain metal alloys like nickel titanium or Nitinol. When Nitinol material is exposed to body heat, it will expand from a compressed diameter to its original diameter. As the Nitinol prosthesis expands, it will exert a radial expansion force that decreases as the prosthesis expands closer to its original diameter, reaching a zero radial expansion force when its original diameter is reached. Thus, use of a shape memory alloy such as Nitinol is one way to provide an intrinsic radial restraint. A non-shape memory material that is elastically deformed during compression will also exhibit diameter-related expansion forces when allowed to return to its original shape.

Although both shape memory and non-shape memory based material may provide diameter-dependent expansion forces that reach zero upon attaining their original shapes, the degree of force exerted can be further modified by altering the thickness of the wire or structure used to configure the support or prosthesis. The prosthesis may be configured with thicker wires to provide a greater expansion force to resist, for example, greater radial inward forces located at the native valve site, but the greater expansion force will still reduce to zero upon the prosthesis attaining its preset diameter. Changes to the wire thickness need not occur uniformly throughout a support or a prosthesis. Wire thickness can vary between different circumferences of a support or prosthesis, or between straight portions and bends of the wire structure.

The other way of controlling diameter previously mentioned is to alter or resist the radial inward or recoil forces acting upon the support or prosthesis. Recoil forces refer to any radially inward force acting upon the valve assembly that prevents the valve support from maintaining a desired expanded diameter. Recoil forces include but are not limited to radially inward forces exerted by the surrounding tissue and forces caused by elastic deformation of the valve support. Opposing or reducing recoil forces help to ensure deployment of the support structure to the desired diameter.

Means for substantially minimizing recoil are also contemplated. Such means may include a feature, such as a mechanical stop, integral with the support structure to limit recoil. By forming an interference fit between the mechanical stop and another portion of the support structure when the support structure is expanded to its preset diameter, the support structure can resist collapse to a smaller diameter and resist further expansion beyond the preset diameter. The interference fit may comprise an intercalating teeth configuration or a latch mechanism. Alternatively, a separate stent may be applied to the lumen of the cardiac ring to further push aside the native valve leaflets or valve remnants by plastically deforming a portion of the prosthesis. This separate stent may be placed in addition to the support structure and may overlap at least a portion of the support structure. By overlapping a portion of the support structure, the separate stent can reduce any recoil force acting on the support structure. It is also contemplated that this separate stent might be applied to the native lumen before the introduction of the valve prosthesis described herein. Another alternative is to plastically deform the valve assembly diameter beyond its yield point so that the prosthesis does not return to its previous diameter.

At portions of the prosthesis where the control of the expansion force against surrounding tissue is desired, the various methods for controlling diameter can be adapted to provide the desired control of expansion force. Portions of the prosthesis may include areas used for anchoring and sealing such as the axial wedging portions previously described.

Specifically, in order to support the valve, the axial valve support portion can have a part in the form of an undulating wire with large-amplitude undulations, and a part in the form of an undulating wire with small-amplitude undulations, adjacent to said part with large amplitude undulations, having a relatively greater radial force in order to make it possible to push said valvular tissue against or into the wall of the passage. Preferably, the support according to one embodiment of the present invention has two axial wedging portions, one connected to an axial end of said valve support portion and the other to the other axial end of this same valve support portion. These two axial wedging portions thus make it possible to wedge the support on both sides of the existing cardiac ring, and consequently make possible complete wedging of the support in two opposite directions with respect to the treated site. If necessary, for example, in the case in which the passage with the valve has an aneurysm, the support according to the invention has: an axial holding portion, suitable for supporting in the deployed state the wall of the passage, and connecting wires such as the aforementioned connecting wires, connecting said axial valve support portion and said axial holding portion, these wires having a length such that the axial holding portion is situated after implantation a distance away from the axial valve support portion. This distance allows said axial holding portion to rest against a region of the wall of the passage not related to a possible defect which may be present at the approach to the valve, particularly an aneurysm. The length of the connecting wires can also be calculated in order to prevent the axial holding portion from coming into contact with the ostia of the coronary arteries. The aforementioned axial portions (valve support, wedging, holding portions) can have a structure in the form of an undulating wire, in zigzag form, or preferably a structure in diamond-shaped mesh form, the mesh parts being juxtaposed in the direction of the circumference of these portions. This last structure allows a suitable radial force making it possible to ensure complete resting of said portions against the wall that receives them.

As previously mentioned, the support according to the invention can be produced from a metal that can be plastically deformed. The instrument for positioning of the support then includes a balloon which has an axial portion with a predetermined diameter, adapted for realizing the deployment of said axial valve support portion, and at least one axial portion shaped so as to have, in the inflated state, a greater cross section than that of the passage to be treated, in such a way as to produce the expansion of the axial wedging portion placed on it until this axial wedging portion encounters the wall which it is intended to engage. The support according to this embodiment of the present invention can also be produced from a material that can be elastically deformed or even a material with shape memory, such as Nitinol, which can be contracted radially at a temperature different from that of the body of the patient and which regains its original shape when its temperature approaches or reaches that of the body of the patient.

Alternatively, the support may be made from a shape memory material that can be plastically deformed, or may be partially made from a shape memory material and partially made from a material that can be plastically deformed. With this embodiment, the support can be brought, by shape memory or plastic deformation, from a state of contraction to a stable intermediate state of deployment between the state of contraction and the state of total deployment, and then by plastic deformation or shape memory respectively, from said intermediate state of deployment to said state of total deployment. In said intermediate state of deployment, the support is preferably configured such that it remains mobile with respect to the site to be treated. The support may thus be brought to the site to be treated and then deployed to its intermediate state; its position can then possibly be adapted and/or corrected, and then the support be brought to its state of total deployment. One example of a shape memory material that can be plastically deformed may be a nickel-titanium alloy of the type called "martensitic Nitinol" that can undergo plastic deformation by means of a balloon. By using a balloon to expand and stress the alloy beyond its yield point, plastic deformation can occur. Plastic deformation by a balloon of a portion of the prosthesis that has already undergone self-expansion can also be used to compensate for any recoil that occurs.

Advantageously, the support according to the invention has some anchoring means suitable for insertion into the wall of the site to be treated, and is shaped in such a way as to be mobile between an inactive position, in which it does not obstruct the introduction of the support into the body of the patient, and an active position, in which it is inserted into the wall of the site to be treated. Substantially complete immobilization of the support at the site is thus obtained. In particular, this anchoring means can be in the form of needles and can be mounted on the support between retracted positions and radially projected positions. Advantageously, the axial valve support portion has, at the site of its exterior surface, a sealing means shaped in such a way as to absorb the surface irregularities that might exist at or near the existing cardiac ring. This sealing means can consist of a peripheral shell made from a compressible material such as polyester or tissue identical to the valve or a peripheral shell delimiting a chamber and having a radially expandable structure, this chamber being capable of receiving an inflating fluid suitable for solidifying after a predetermined delay following the introduction into said chamber. This sealing means can also include a material that can be applied between the existing cardiac ring and the axial valve support portion, this material being capable of solidifying after a predetermined delay following this application. Specifically, in this case, this material is capable of heat activation, for example, by means of a laser, through the balloon, or capable of activation by emission of light of predetermined frequency, for example, by means of an ultraviolet laser, through the balloon. Said sealing means can also be present in the form of an inflatable insert with a spool-shaped cross section in the inflated state, which can be inserted between the existing cardiac ring and the axial valve support portion, Said spool shape allows this insert to conform to the best extent possible to the adjacent irregular structures and to provide a better seal.

In one embodiment of the invention, a drug-eluting component is contemplated. This component comprises a surface coating or matrix bonding to at least a portion of support structure. Drug elution is well known to those in the art. Potential drugs may include but are not limited to antibiotics, cellular anti-proliferative and anti-thrombogenic drugs.

An assembly and method for removing the native valve is also contemplated. In particular, the invention has the objective of providing a device that gives complete satisfaction with regard to the exeresis and replacement of the valve, while allowing one to operate without opening of the thorax, stopping of the heart and/or opening of the heart, and preventing any diffusion into the circulatory system of fragments of the removed valve. In one embodiment, the assembly comprises: (a) an elongated support element; (b) a first set of elongated blades arranged around the circumference of said elongated element and connected in a pivoting manner to the elongated element at the site of their proximal longitudinal ends, each blade having a sharp edge at the site of its distal longitudinal end and configured to pivot with respect to the elongated element between a folded up (retracted) position, in which they are near the wall of the elongated element in such a way that they do not stand in the way of the introduction and sliding of the device in the body channel in which the valve is located, in particular in the aorta, and an opened out (protracted) position, in which these blades are spread out in the form of a corolla in such a way that their sharp edges are placed in extension of one another and thus constitute a sharp circular edge; (c) a second set of blades arranged consecutively to said first series of blades in the distal direction; the blades of this second set have a structure identical to that of the blades of said first set, wherein the blades of this second series are connected to the elongated element by their distal longitudinal ends and wherein each has a sharp edge at the site of its proximal longitudinal end; (d) means making it possible to bring the blades of said first and second set from their retracted position to their protracted position; (e) means for permitting axial movement of the sets of blades axially relative to one another between a spaced position in which one set of blades can be placed axially on one side of the natural valve while the other set of blades is placed axially on the other side of this valve, and a proximate position in which the sharp circular edges of the two sets of blades may be brought into mutual contact for excising the natural valve.

A method of using this assembly comprises the steps of introducing the assembly percutaneously into said body channel and delivering the assembly to a position where the first and second sets of blades are spaced on opposite sides of the natural valve using the means of identification. The method may further comprise putting in place a system of peripheral aorto-venous heart assistance, extracorporeal circulation or a blood pump through the center of the delivery system for pumping blood, in the case of an aortic valve replacement, from the left ventricle (proximal to the aortic valve) to the aorta (distal to the aortic valve) in order to facilitate the flow of the blood, for the purpose of preventing stagnation of the blood in the heart. One embodiment of a blood flow pump is described further below. After the assembly is positioned in place, the method further comprises spreading the blades of the two sets of blades out; then bringing the two sets closer together to excise the valve. The configuration of these blades makes it possible to execute this cutting in a single operation, minimizing the generation of fragments that can be diffused into the circulatory system. This configuration moreover makes possible precise control of the diameter according to which the natural valve is cut, in view of later calibration of the prosthetic valve. The blades may then be retracted for placement of the prosthetic valve.

The prosthetic valve may be deployed discretely from the assembly, in which case the method may comprise removing the assembly and then separately deploying the prosthetic valve. Preferably however, the assembly comprises a proximal prosthetic valve having an expandable support structure that may occupy a contracted position near the wall of said elongated element for transmission through the body channel, and an expanded position to replace the natural cardiac valve.

After excising the natural valve, the method further comprises sliding the assembly axially in the distal direction in order to bring the prosthetic valve to the desired site in the channel, and then expanding the prosthetic valve support into place. The assembly may then be withdrawn, recovering the excised natural valve.

Preferably, the elongated support element is a tubular catheter permitting blood to flow through it during the excision of the natural valve. The cross section of the channel of this catheter can be sufficient to allow the blood to flow through this channel with or without the help of a pump. Continued blood flow during the excision procedure may limit or eliminate the need for placing the patient under extracorporeal circulation or peripheral aorto-venous heart assistance. The catheter has a lateral distal opening in order to allow the blood to rejoin the body channel, for example the ascending aorta, this opening being arranged in such a way that the length of catheter passed through the blood is as short as possible. Alternatively, the catheter may have a small diameter to facilitate the introduction and delivery of the assembly in the body channel, but a small diameter might require the provision of peripheral circulation by an external assistance system such as an extracorporeal circulation system or-peripheral aorto-venous heart assistance.

Preferably, the assembly for excising the native valve includes a distal inflatable balloon, placed at the site of the exterior surface of said elongated element; wherein the balloon is configured so as to occupy a deflated position, in which it has a cross section such that it does not stand hinder introduction and advancement of the assembly within the body channel, and an expanded position. The balloon may be inflated after the positioning of the sets of blades on both sides of the natural valve in order to prevent reflux of the blood during the ablation of the natural valve. If the elongated element is a catheter, this balloon moreover makes it possible to cause blood to flow only through the catheter. Once the prosthetic valve is positioned, the balloon is deflated to re-establish the blood flow through the body channel.

The assembly for excising the native valve may optionally include a distal filter made of flexible material placed on the exterior surface of the elongated element. The filter is configured so that it can occupy a retracted position or a contracted position. This filter serves to capture possible fragments generated by the excision of the natural valve, for removal from the blood circulation. The assembly may include means for moving the sets of blades in the axial direction relative to the balloon and/or from said filter.

The balloon and optional filter may be separate from the assembly, being mounted on an elongated support element specific to them. In case of operation on a mitral valve, this balloon or filter may be introduced into the aorta by a peripheral artery route, and the assembly is itself introduced into the heart by the peripheral venous system, up to the right atrium and then into the left atrium through the interatrial septum, up to the site of the mitral valve. The prosthetic valve can advantageously have a frame made of a material with a shape memory, particularly a nickel-titanium alloy known as "Nitinol." This same valve can have valve leaflets made of biological material (preserved animal or human valves) or synthetic material such as a polymer. When replacing an aortic valve the assembly may be alternatively introduced in a retrograde manner through a peripheral artery (femoral artery) or through a venous approach and transseptally (antegrade).

One embodiment of a system for deploying a prosthetic valve may comprise a blood pump insertable into the lumen of a catheter to facilitate blood flow across the native valve and implantation sites during the implantation procedure. When the catheter is positioned across the implantation site, a proximal opening of the delivery catheter is on one side of the implantation site and the lateral distal opening is on another side of the implantation site. By inserting the blood pump into the catheter lumen between the proximal and lateral distal openings, blood flow across the native valve and implantation sites is maintained during the procedure. One embodiment of the blood pump comprises a rotating impeller attached to a reversible motor by a shaft. When the impeller is rotated, blood flow can be created in either direction along the longitudinal axis of the catheter between the proximal and lateral distal openings to provide blood flow across the implantation site. The pump may be used during the native valve excision step if so carried out.

In one application of the present invention, the prosthetic valve may be implanted by first passing a guidewire inserted peripherally, for instance, through a vein access; transseptally from the right atrium to the left atrium and then snaring the distal end of the guidewire and externalizing the distal end out of the body through the arterial circulation. This placement of the guidewire provides access to the implantation site from both venous and arterial routes. By providing venous access to the native valve, massive valvular regurgitation during the implantation procedure may be avoided by first implanting the replacement valve and then radially pushing aside the native valve leaflets through the venous access route.

The above embodiments and methods of use are explained in more detail below.

BRIEF DESCRIPTION OF THE DRAWINGS

FIG. 1 is a cross-sectional side view of one embodiment of an assembly of the present invention for removing and replacing a native heart valve percutaneously;

FIG. 2 is a cross-section axial view of the assembly of FIG. 1 taken at line II-II, shown in a closed condition;

FIG. 3 is a cross-section axial view of the assembly of FIG. 1 taken at line II-II, shown in an opened condition;

FIG. 23 is a detail view of the support of FIG. 22 shown in the contracted state;

FIG. 24 is a detail view of the support of FIG. 23 taken along line 23-23;

FIG. 25 is a detail view of the support of FIG. 22 shown in the expanded state;

FIG. 26 is a detail view of the support of FIG. 25 taken along line 25-25;

FIG. 27 is a schematic view of an alternative embodiment of the present invention;

FIG. 28 is a detailed cross section view of the support of FIG. 27;

FIGS. 56A and 56B represent one embodiment of the radial restraint comprising a wire interwoven into the support structure;

FIGS. 74A and 74B are schematic views of an angular mechanical stop for controlling diameter; and FIGS. 75A and 75B are schematic views of an angular mechanical stop with a latch for resisting recoil.

DETAILED DESCRIPTION OF THE PREFERRED EMBODIMENT

Figure 9:
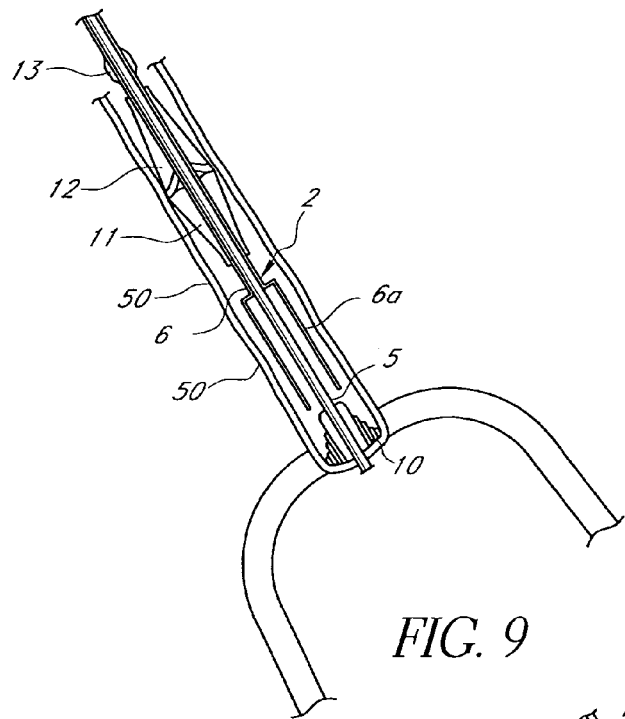
FIGS. 5 to 9 are schematic views of the assembly of the present invention positioned in a heart, at the site of the valve that is to be treated, during the various successive operations by means of which this valve is cut out and the prosthetic valve shown in FIG. 4 deployed.

Reference is now made to the figures wherein like parts are designated with like numerals throughout. FIGS. 1 to 3 represent a device 1 for replacing a heart valve by a percutaneous route. This device comprises a tubular catheter 2 formed from three tubes 5, 6, 7 engaged one inside the other and on which there are placed, from the proximal end to the distal end (considered with respect to the flow of blood, that is to say from right to left in FIG. 1), a prosthetic valve 10, two series of blades 11, 12, a balloon 13 and a filter 14. The three tubes 5, 6, 7 are mounted so that they can slide one inside the other. The interior tube 5 delimits a passage 15, the cross section of which is large enough to allow blood to flow through it. At the proximal end, the intermediate tube 6 forms a bell housing 6a delimiting, with the interior tube 5, an annular cavity 17 in which the prosthetic valve 10 is contained in the furled condition.

Figure 4:
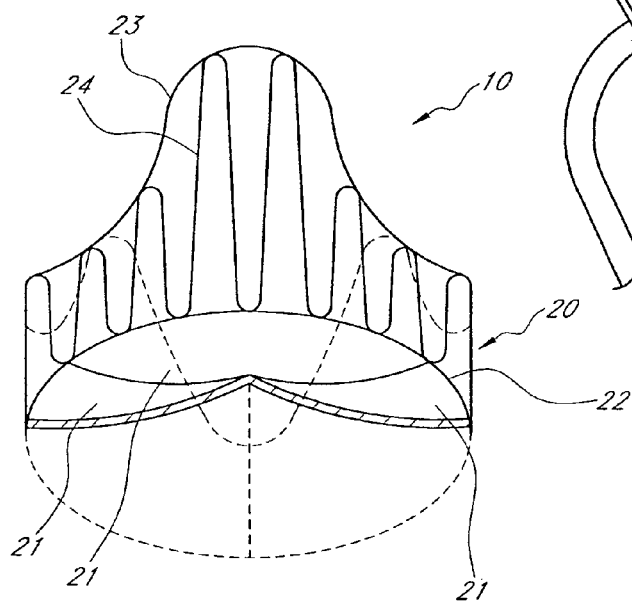
FIG. 4 is a perspective schematic view of one embodiment of a prosthetic valve of the present invention.

FIG. 4 shows that this valve 10 comprises an armature 20 and valve leaflets 21 mounted so that they are functionally mobile on this armature 20. The armature comprises a collection of wires 22, 23, 24 made of shape memory material, particularly of nickel-titanium alloy known by the name of "NITINOL;" namely, (i) a proximal end wire 22 which, when the valve 10 is in the deployed state, has a roughly circular shape; (ii) a distal end wire 23 forming three corrugations in the axial direction, these corrugations being distributed uniformly around the circumference of the valve 10, and (iii) an intermediate wire 24 forming longitudinal corrugations between the wires 22 and 23, this wire 24 being connected to the latter ones via the ends of each of these corrugations. The valve leaflets 21 for their part are made of biological material (preserved human or animal valve leaflets) or of synthetic material, such as a polymer. The armature 20 may, when its material is cooled, be radially contracted so that the valve 10 can enter the cavity 17. When this material is heated to body temperature, this armature 20 returns to its original shape, depicted in FIG. 4, in which it has a diameter matched to that of a bodily vessel, particularly the aorta, in which the native valve that is to be treated lies. This diameter of the armature 20 is such that the valve 10 bears against the wall of the bodily vessel and is immobilized in the axial direction with respect to that vessel.

Each series of blades 11, 12 comprises metal elongate blades 30 and an inflatable balloon 31 situated between the catheter 2 and these blades 30. The blades 30 have a curved profile and are arranged on the circumference of the catheter 2, as shown in FIGS. 2, 3 and 3A. The blades 30 of the proximal series 11 are connected pivotably to the tube 6 by their proximal ends and comprise a cutting distal edge 30a, while the blades 30 of the distal series 12 are connected pivotably to the exterior tube 7 by their distal ends and comprise a cutting proximal edge 30b. The connection between the blades 30 and the respective tubes 6 and 7 is achieved by welding the ends of the blades 30 together to form a ring, this ring being fixed axially to the corresponding tube 6, 7 by crimping this ring onto this tube 6, 7, the pivoting of the blades 30 being achieved by simple elastic deformation of these blades 30. This pivoting can take place between a position in which the blades 30 are furled, radially internally with respect to the catheter 2 and shown in FIGS. 1 and 2, and a position in which these blades 30 are unfurled, radially externally with respect to this catheter 2 and shown in FIG. 3. In the furled position, the blades 30 lie close to the wall of the tube 6 and partially overlap each other so that they do not impede the introduction and the sliding of the device 1 into and in the bodily vessel in which the native valve that is to be treated lies; in said unfurled position, the blades 30 are deployed in a corolla so that their cutting edges 30a, 30b are placed in the continuation of one another and thus constitute a circular cutting edge visible in FIG. 3.

Each balloon 31, placed between the tube 3 and the blades 30, may be inflated from the end of the catheter 2 which emerges from the patient, via a passage 32 formed in the tube 6. It thus, when inflated, allows the blades 30 to be brought from their furled position into their unfurled position, and performs the reverse effect when deflated. The axial sliding of the tube 6 with respect to the tube 7 allows the series of blades 11, 12 to be moved axially toward one another, between a spaced-apart position shown in FIG. 1, and a close-together position. In the former of these positions, one series of blades 11 may be placed axially on one side of the native valve while the other series of blades 12 is placed axially on the other side of this valve, whereas in the latter of these positions, the circular cutting edges of these two series of blades 11, 12 are brought into mutual contact and thus cut through the native valve in such a way as to detach it from said bodily vessel. The tubes 5 to 7 further comprise marks (not visible in the figures) in barium sulfate allowing the axial position of the device 1 with respect to the native valve to be identified percutaneously so that each of the two series of blades 11, 12 can be placed on one axial side of this valve. These tubes 5 to 7 also comprise lateral distal openings (not depicted) to allow the blood to reach the bodily vessel, these openings being formed in such a way that the length of catheter 2 through which the blood flows is as short as possible, that is to say immediately after the filter 14, in the distal direction.

The balloon 13 is placed on the exterior face of the tube 7, distally with respect to the series 12. This balloon 13 has an annular shape and is shaped to be able to occupy a furled position in which it has a cross section such that it does not impede the introduction and sliding of the device 1 into and in said bodily vessel, and an unfurled position, in which it occupies all of the space between the exterior face of the tube 7 and the wall of said bodily vessel and, via a peripheral edge 13a which it comprises, bears against this wall.

The filter 14 is placed distally with respect to the balloon 13, on the tube 7, to which it is axially fixed. This filter 14 is made of flexible material, for example polyester netting, and is shaped to be able to occupy a furled position in which it has a cross section such that it does not impede the introduction and sliding of the device 1 into and in said bodily vessel, and an unfurled position in which it occupies all of the space between the exterior face of the catheter 2 and the wall of this vessel and, via a peripheral edge 14a which it comprises, bears against this wall.

Figure 10:
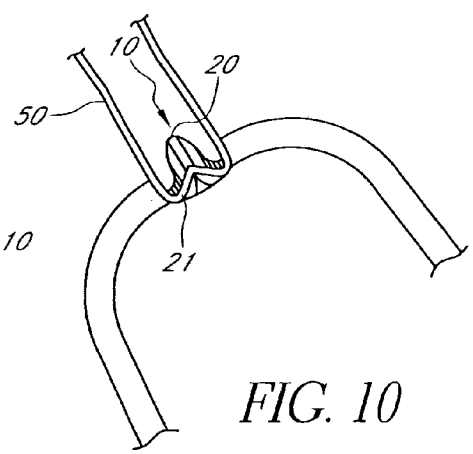
FIG. 10 is a schematic view of the prosthetic valve shown of FIG. 4 shown in a deployed state.
Figures 5, 6:
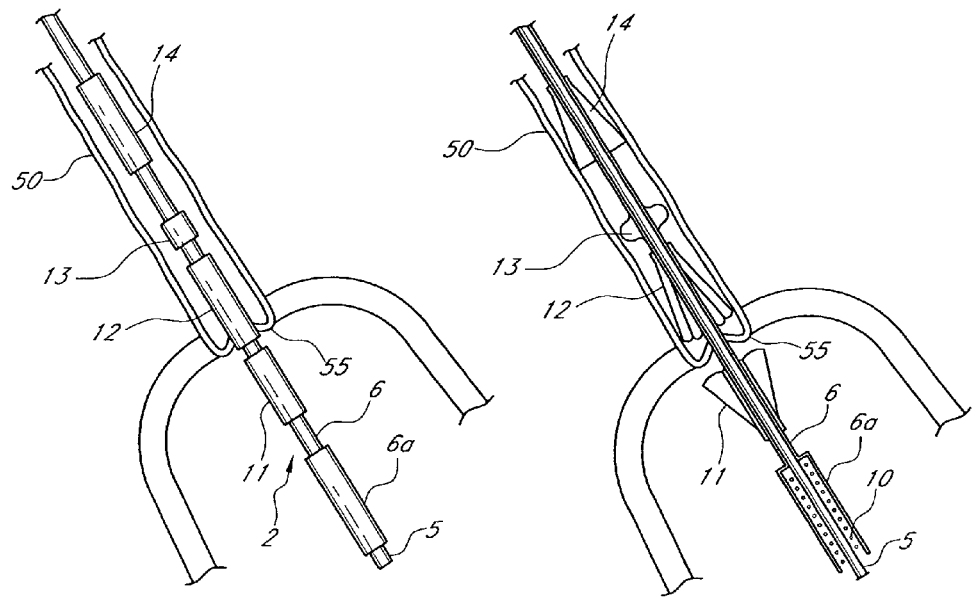
Figures 7, 8:
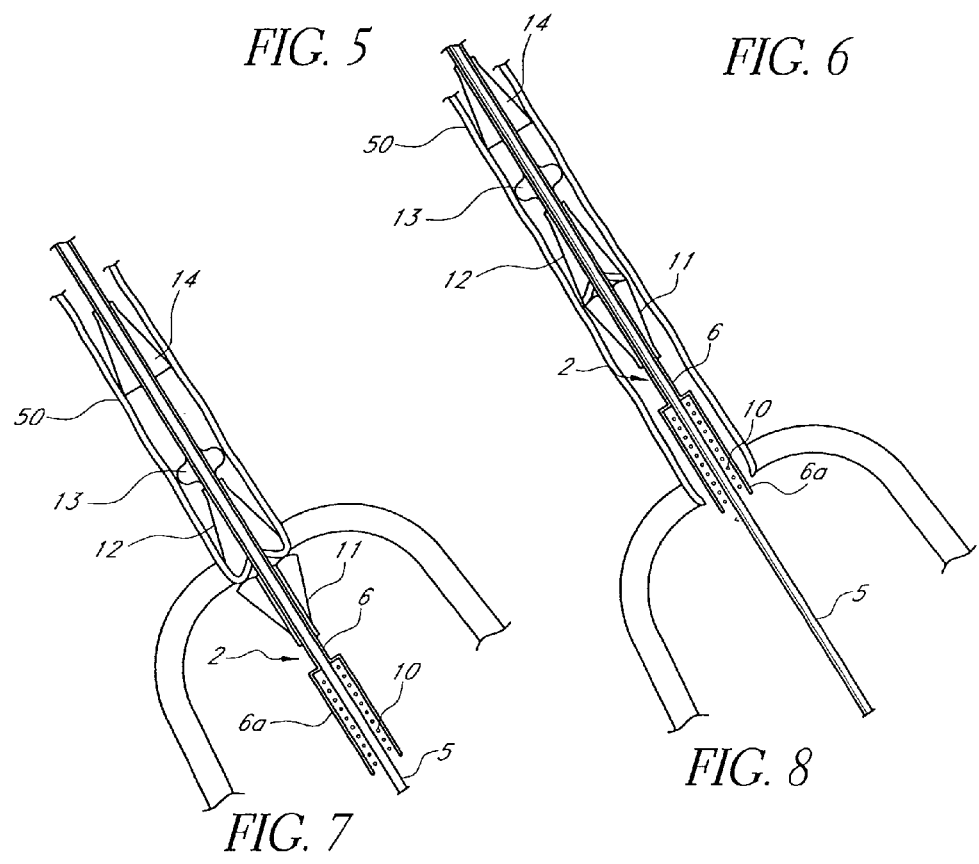

An inflatable balloon 35 is placed between the tube 7 and the filter 14 so as, depending on whether it is inflated or deflated, to bring the filter 14 into its respective unfurled and furled positions. In practice, as shown by FIGS. 5 to 9, the device 1 is introduced into said bodily vessel 50 by a percutaneous route and is slid along inside this vessel 50 until each of the series 11, 12 of blades is placed on one side of the native valve 55 that is to be treated (FIG. 5). This position is identified using the aforementioned marks. When the device is in this position, the proximal part of the catheter 2 is situated in the heart, preferably in the left ventricle, while the aforementioned distal lateral openings are placed in a peripheral arterial vessel, preferably in the ascending aorta. The balloons 13 and 35 are inflated in such a way as to cause blood to flow only through the passage 15 and prevent blood reflux during the ablation of the valve 55. A peripheral perfusion system is set in place to facilitate this flow, as further described below in connection with FIGS. 50 through 52. The blades 30 of the two series 11, 12 are then deployed (FIG. 6) by inflating the balloons 31, then these two series 11, 12 are moved closer together by sliding the tube 6 with respect to the tube 7, until the valve 55 is cut through (FIG. 7). The blades 30 are then returned to their furled position by deflating the balloons 31 while at the same time remaining in their close-together position, which allows the cut-out valve 55 to be held between them. The device 1 is then slid axially in the distal direction so as to bring the bell housing 6a to the appropriate position in the vessel 50 (FIG. 8), after which the valve 10 is deployed by sliding the tube 6 with respect to the tube 5 (FIG. 9). The balloons 13 and 35 are deflated then the device 1 is withdrawn and the cut-out valve 55 is recovered (FIG. 10).

Figure 11:
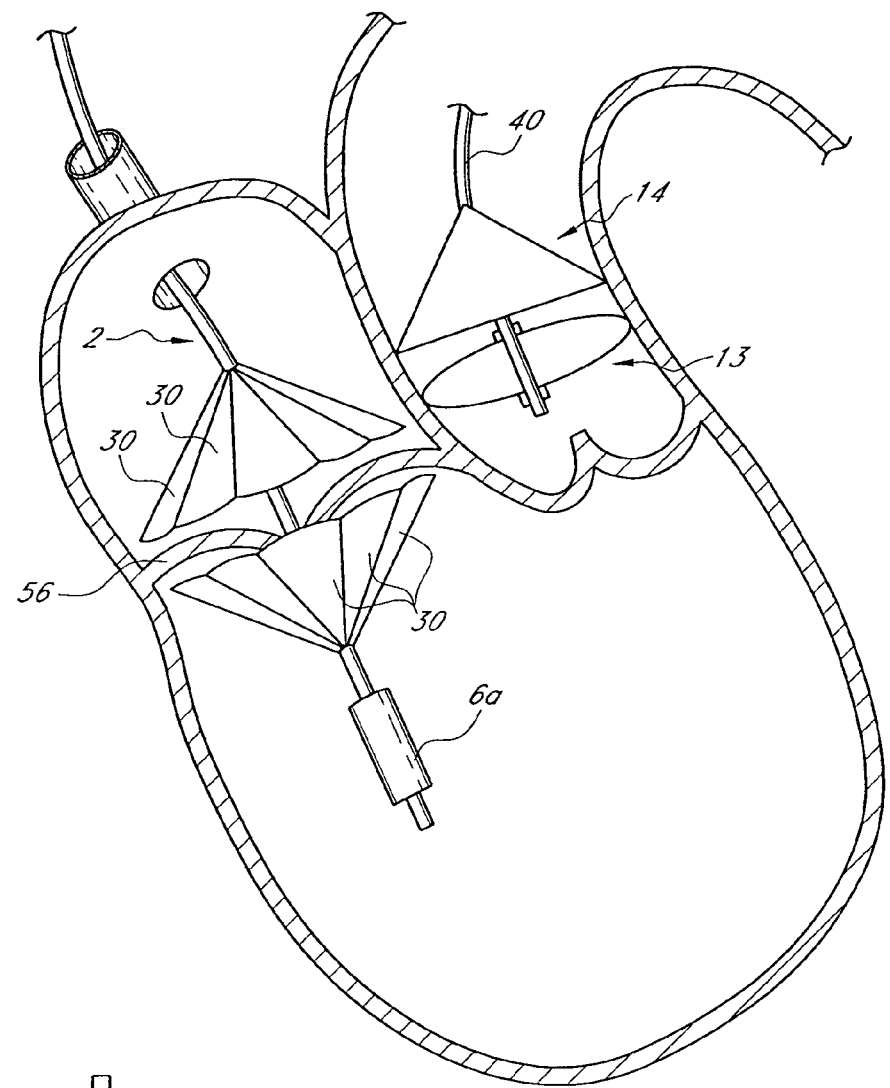
FIG. 11 is a schematic view of an alternative embodiment of the assembly of the present invention shown treating a mitral valve.

FIG. 11 shows a second embodiment of the device 1, allowing operation on a mitral valve 56. The same reference numerals are used to denote the same elements or parts as the aforementioned, as long as these elements or parts are identical or similar in both embodiments. In this case, the tubular catheter is replaced by a support wire 2, on which one of the series of blades is mounted and by a tube engaged over and able to slide along this wire, on which tube the other series of blades is mounted; the passages for inflating the balloons 31 run along this support wire and this tube; the balloon 13 and the filter 14 are separate from the device 1 and are introduced into the aorta via a peripheral arterial route, by means of a support wire 40 along which the passages for inflating the balloons 13 and 35 run. The device 1, devoid of balloon 13 and the filter 14, is for its part introduced into the heart through the peripheral venous system, as far as the right atrium then into the left atrium through the inter-auricular septum, as far as the valve 56. For the remainder, the device 1 operates in the same way as was mentioned earlier. The invention thus provides a device for replacing a heart valve by a percutaneous route, making it possible to overcome the drawbacks of the prior techniques. Indeed the device 1 is entirely satisfactory as regards the cutting-away of the valve 55, 56, making it possible to operate without stopping the heart and making it possible, by virtue of the filter 14, to prevent any dispersion of valve fragments 55, 56 into the circulatory system.

Figure 12:
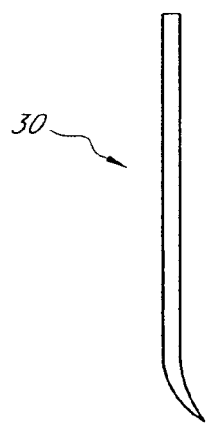
FIG. 12 is a cross-sectional view of a section of a blade used in excising the native valve.
Figure 13:
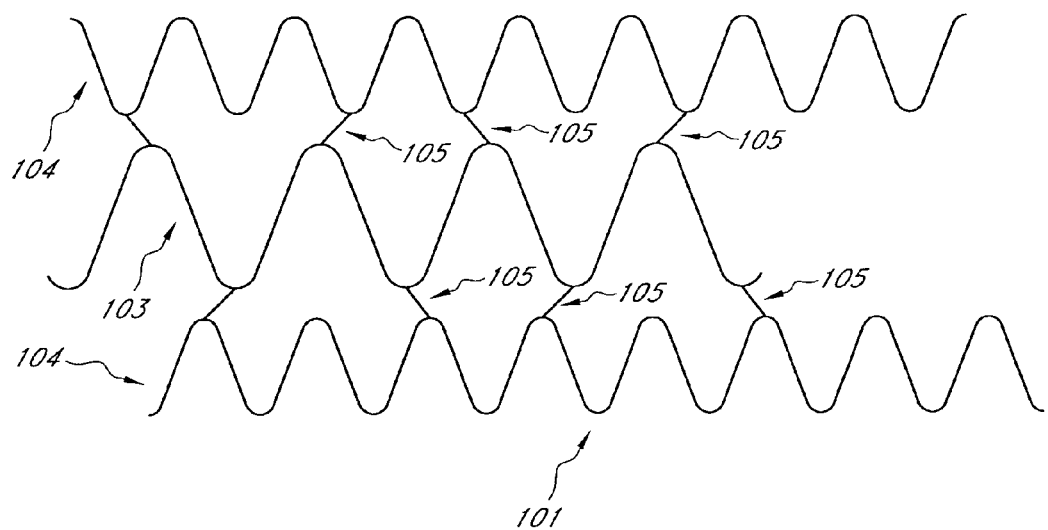
FIG. 13 is a schematic view of one embodiment of the support structure of the prosthesis assembly of the present invention.
Figure 14:
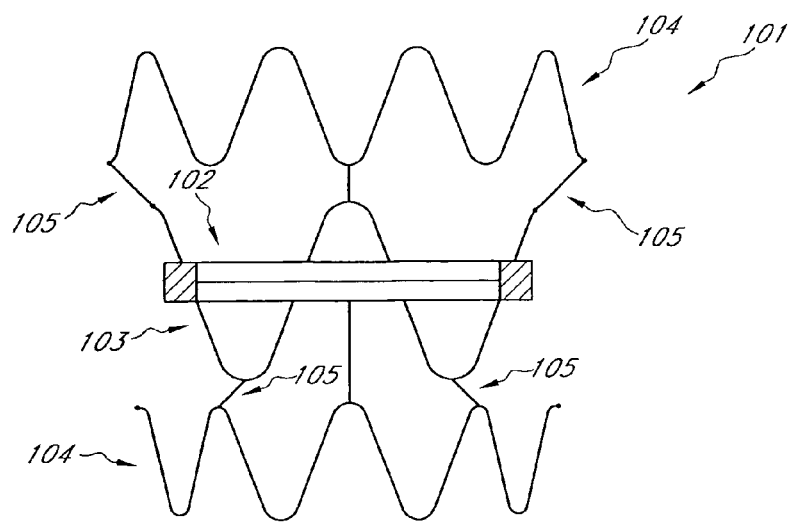
FIG. 14 is a cross-sectional view of the support of FIG. 13 showing a heart valve supported by the central portion of the support.

The above device may comprise a fourth tube, engaged on and able to slide along the tube 7, this fourth tube comprising the balloon and the filter mounted on it and allowing said series of blades to be moved in the axial direction independently of said balloon and/or of said filter; the blades may be straight as depicted in the drawing or may be curved toward the axis of the device at their end which has the cutting edge, so as to eliminate any risk of lesion in the wall of the bodily vessel, as shown in FIG. 12; the filter 14 may be of the self-expanding type and normally kept in the contracted position by a sliding tube, which covers it, making the balloon 35 unnecessary.

FIGS. 13 to 16 represent tubular support 101 for positioning, by percutaneous route, of replacement heart valve 102. The support structure 101 includes median portion 103, which contains valve 102, two extreme wedging portions 104 and wires 105 for connecting these portions 103 and 104. Median portion 103 also includes peripheral shell 106 provided with anchoring needles 107 and shell 108 made of compressible material. As is particularly apparent from FIG. 12, each of portions 103 and 104 is formed with an undulating wire, and wires 105 connect pointwise the ends of the undulations of portion 103 to the end of an adjacent wave of portion 104. Portions 104, seen in expanded form, have lengths greater than the length of portion 103, so that when the ends of the wires respectively forming portions 103 and 104 are connected in order to form the tubular support structure 101, the diameter of portion 103 is smaller than the diameter of portions 104.

Figure 15:
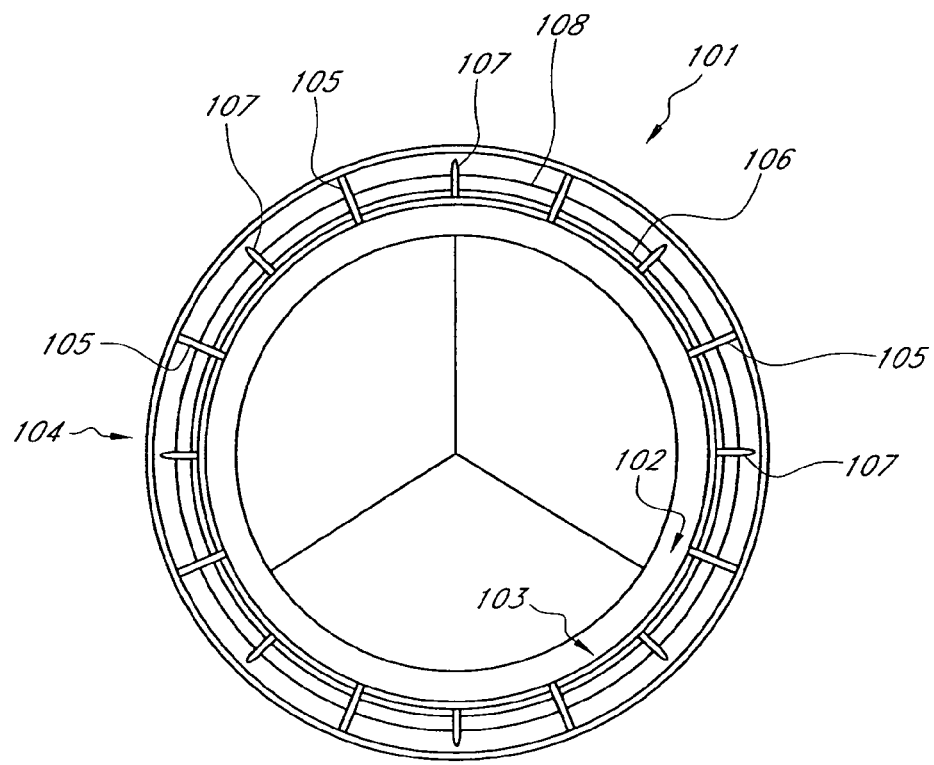
FIG. 15 is an end view of the support of FIGS. 13 and 14 in the deployed state.
Figure 16:
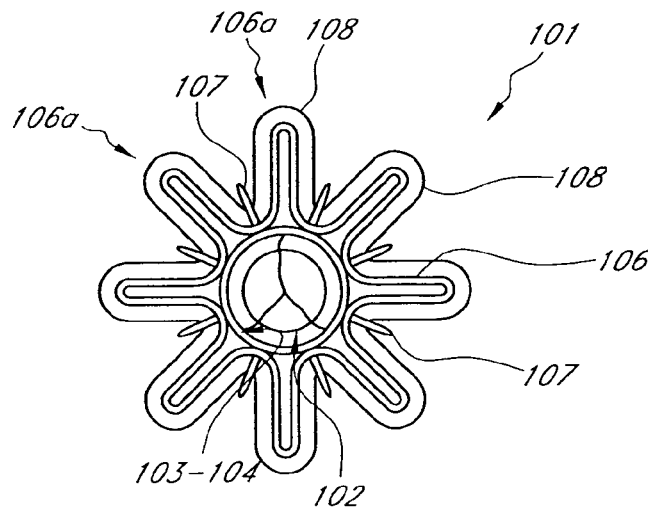
FIG. 16 is an end view of the support of FIGS. 13 and 14 in the contracted state.
Figure 17:
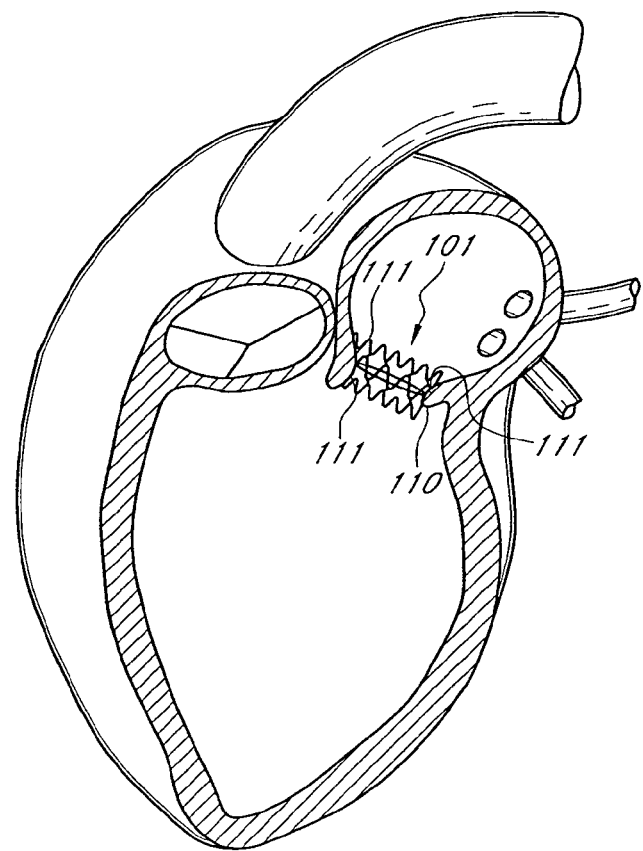
FIG. 17 is a schematic view of a heart with an embodiment of the present inventive prosthesis shown deployed in place.

The diameter of portion 103 is such that portion 103 can, as shown by FIG. 17, support cardiac ring 110 that remains after removal of the deficient native valve, while portions 104 support walls 111 bordering ring 110. These respective diameters are preferably such that said supporting operations take place with slight radial restraint of ring 110 and walls 111. Portion 103 presents in the deployed state a constant diameter. Portions 104 can have a constant diameter in the form of a truncated cone whose diameter increases away from portion 103. The entire support structure 101 can be made from a material with shape memory, such as the nickel-titanium alloy known as "Nitinol." This material allows the structure to be contracted radially, as shown in FIG. 16, at a temperature different from that of the body of the patient and to regain the original shape shown in FIGS. 14 and 15 when its temperature approaches or reaches that of the body of the patient. The entire support structure 101 can also be made from a material that can be expanded using a balloon, such as from medical stainless steel (steel 316 L). Valve 102 can be made of biological or synthetic tissue. It is connected to portion 103 by sutures or by any other appropriate means of attachment. It can also be molded on portion 103. Shell 106 may be made of "Nitinol." It is connected to the undulations of portion 103 at mid-amplitude, and has needles 107 at the site of its regions connected to these undulations. Needles 107 consist of strands of metallic wire pointed at their free ends, which project radially towards the exterior of shell 106.

This shell can take on the undulating form that can be seen in FIG. 16 in the contracted state of support 101 and the circular form which can be seen in FIG. 4 in the deployed state of this support 101. In its undulating form, shell 106 forms undulations 106a projecting radially on the outside of support 101, beyond needles 107, so that these needles 107, in the retracted position, do not obstruct the introduction of support 101 in a catheter or, once support 101 has been introduced into the heart using this catheter, do not obstruct the deployment out of this support 1. The return of shell 106 to its circular form brings needles 107 to a position of deployment, allowing them to be inserted in ring 110 in order to complete the anchoring of support 101. Shell 108 is attached on shell 106. Its compressible material allows it to absorb the surface irregularities that might exist at or near ring 110 and thus to ensure complete sealing of valve 102.

Figure 18:
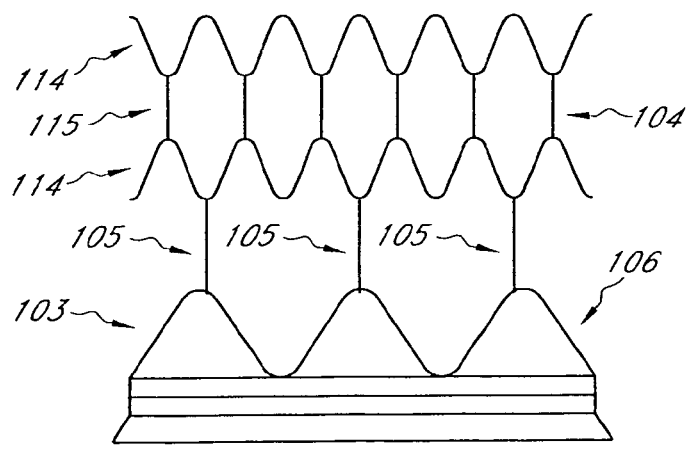
FIG. 18 is a schematic view of an alternative embodiment of the present invention.
Figure 19:
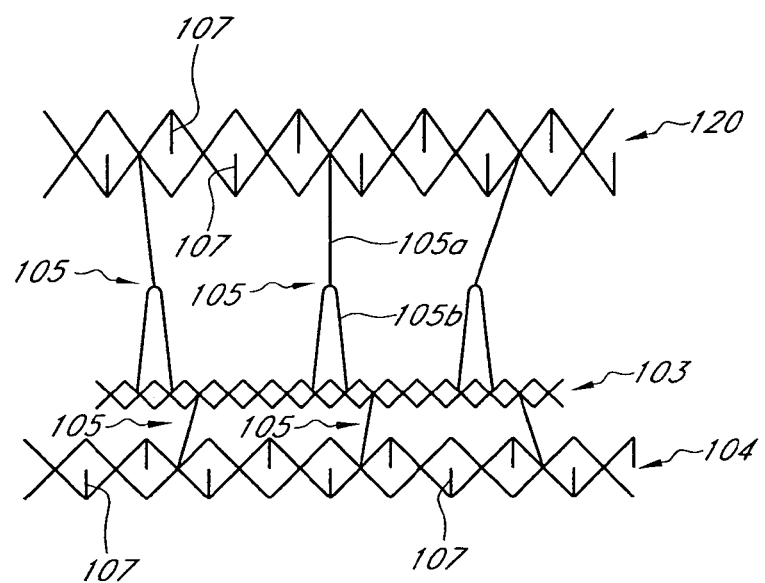
FIG. 19 is schematic view of an alternative embodiment of the present invention.

FIG. 18 shows a support structure 101 having a single portion 104 connected to portion 103 by wires 105. This portion 104 is formed by two undulating wires 114 connected together by wires 115. FIG. 19 shows a support structure 101 that has portion 103 and portion 104 connected by connecting wires 105. These portions 103 and 104 have diamond-shaped mesh structures, these mesh parts being juxtaposed in the direction of the circumference of these portions and connected together at the site of two of their opposite angles in the direction of the circumference of these portions 103 and 104. Wires 105 are connected to these structures at the site of the region of junction of two consecutive mesh parts. These mesh parts also have anchoring hooks 107 extending through them from one of their angles situated in the longitudinal direction of support 101.

Figure 20:
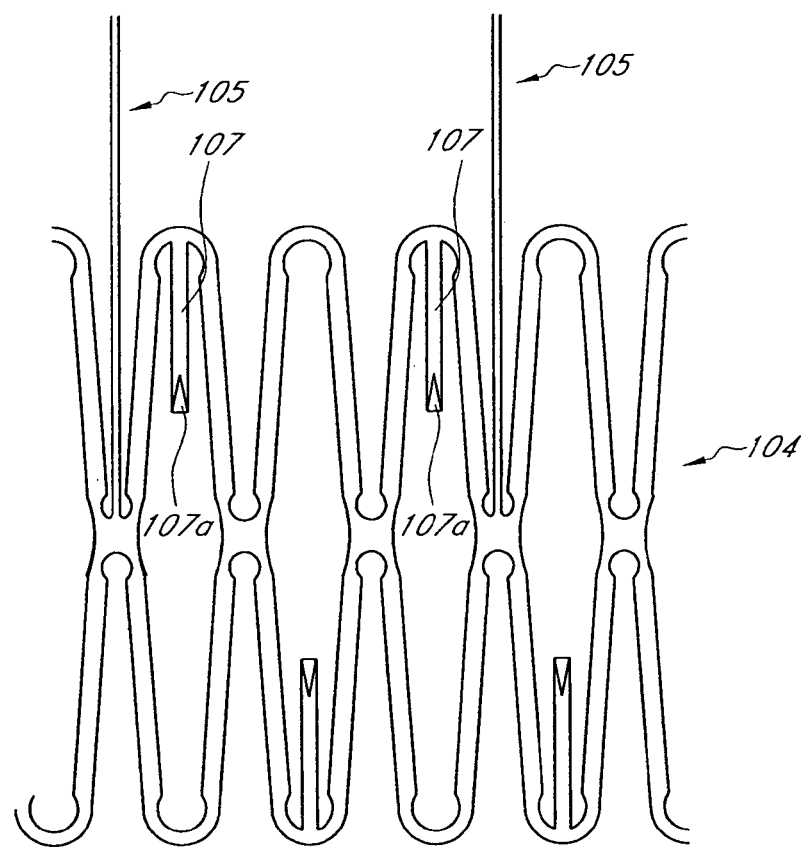
FIG. 20 is a detail view of a part of the support structure of one embodiment of the present invention.

FIG. 20 illustrates, in an enlarged scale, the structure of this portion 104 and of a part of wires 105, as cut, for example, with a laser from a cylinder of stainless steel, and after bending of sharp ends 107a of hooks 107. These hooks, in a profile view, can have the shape as shown in FIG. 24 or 26. The structure represented in FIG. 19 also has axial holding portion 120, which has a structure identical to that of portion 104 but with a coarser mesh size, and three wires 105 of significant length connecting this portion 120 to portion 103. These wires 105, on the side of portion 120, have a single link 105a and on the side of portion 103, a double link 105b. Their number corresponds to the three junctions formed by the three valves of valve 102, which facilitates mounting of valve 102 on support 101 thus formed. The support according to FIG. 19 is intended to be used, as appears in FIG. 21, when the body passage with the valve to be replaced, in particular the aorta, has a variation in diameter at the approach to the valve. The length of wires 105 connecting portions 103 and 120 is provided so that after implantation, portion 120 is situated in a non-dilated region of said body passage, and this portion 120 is provided so as to engage the wall of the passage.

Figure 22:
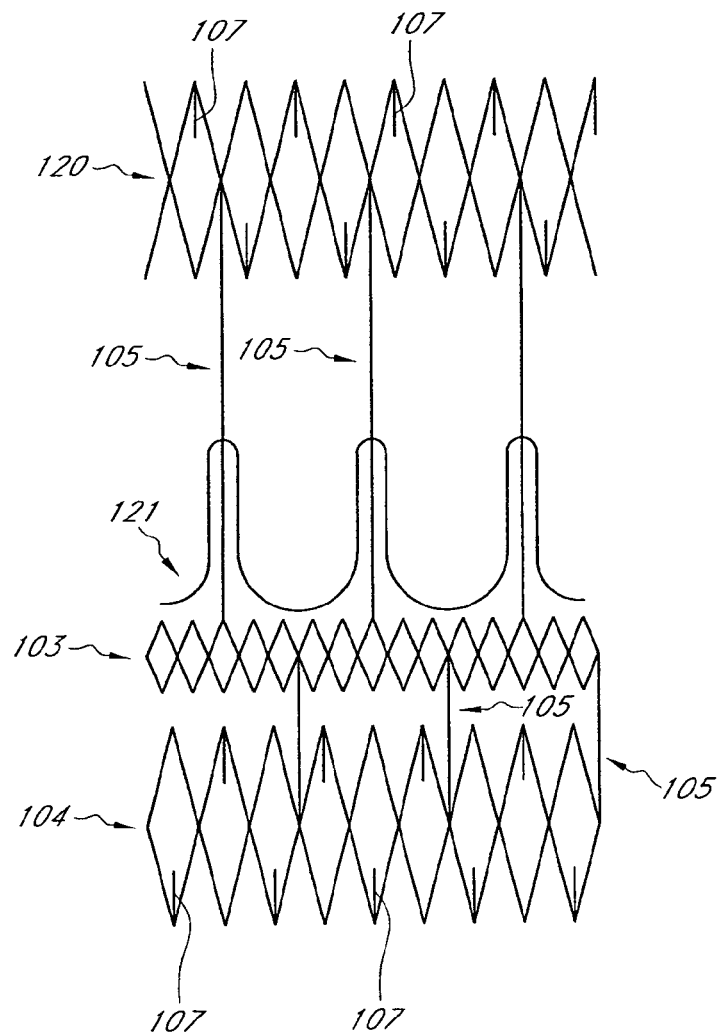
FIG. 22 is schematic view of an alternative embodiment of the present invention.

FIG. 22 shows a structure similar to that of FIG. 19 but unexpanded, except that the three wires 105 have a single wire structure but have an undulating wire 121 ensuring additional support near portion 103. This wire 121 is designed to support valve 102 with three valve leaflets. FIGS. 23 to 26 show an embodiment variant of the structure of portions 103, 104 or 120, when this structure is equipped with hooks 107. In this case, the structure has a zigzagged form, and each hook 107 has two arms 107b; each of these arms 107b is connected to the other arm 107b at one end and to an arm of structure 101 at its other end. The region of junction of the two arms 107b has bent hooking pin 107a.

Figure 29:
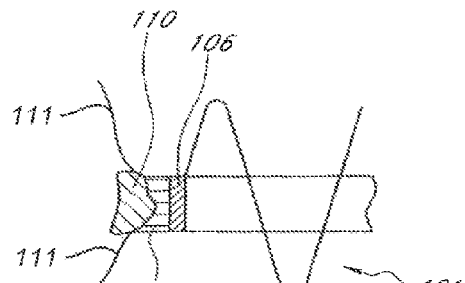
FIG. 29 is a partial schematic view in longitudinal section of the support of the present invention and of a calcified cardiac ring.
Figure 30:
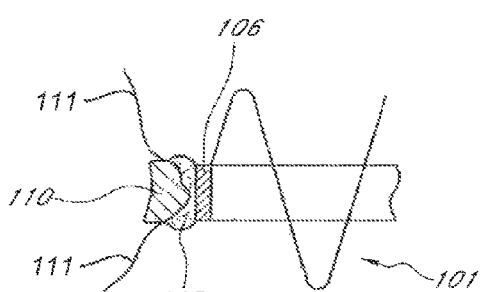
FIG. 30 is a schematic view of an alternative to the support of FIG. 29.

FIG. 27 shows portion 103 that has two undulating wires 125, 126 extending in the vicinity of one another and secondary undulating wire 127. As represented in FIG. 28, wires 125, 126 can be used to execute the insertion of valve 102 made of biological material between them and the attachment of this valve 102 to them by means of sutures 127. FIG. 29 shows a part of support 101 according to FIGS. 13 to 17 and the way in which the compressible material constituting shell 108 can absorb the surface irregularities possibly existing at or near ring 110, which result from calcifications. FIG. 30 shows support 101 whose shell 106 has no compressible shell. A material can then be applied, by means of an appropriate cannula (not represented), between ring 110 and this shell 106, this material being able to solidify after a predetermined delay following application.

Figure 31:
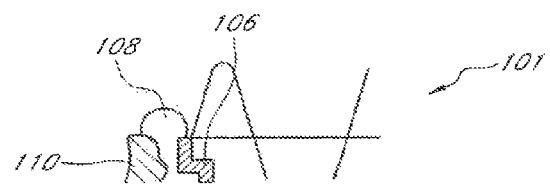
FIG. 31 is a schematic view of an alternative to the support of FIG. 29.

FIG. 31 shows support 101 whose shell 106 has a cross section in the form of a broken line, delimiting, on the exterior radial side, a lower shoulder. Housed in the step formed by this shoulder and the adjacent circumferential wall is peripheral shell 108 which can be inflated by means of a catheter (not represented). This shell 108 delimits a chamber and has a radially expandable structure, such that it has in cross section, in the inflated state, two widened ends projecting on both sides of shell 106. This chamber can receive an inflating fluid that can solidify in a predetermined delay following its introduction into said chamber. Once this material has solidified, the inflating catheter is cut off.

Figure 32:
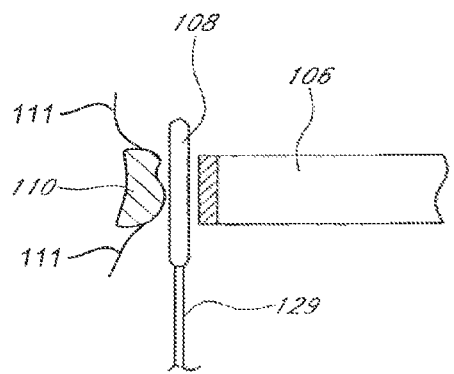
FIGS. 32 and 33 are schematic views of an alternative to the support of FIG. 29.
Figure 33:
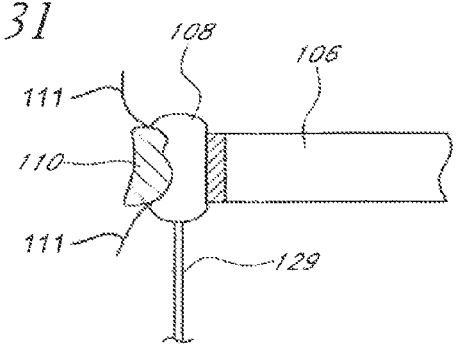

FIGS. 32 and 33 show support 101 whose shell 106 receives inflatable insert 108 which has a spool-shaped cross section in the inflated state; this insert 108 can be inflated by means of catheter 129. Insert 108 is positioned in the uninflated state (FIG. 32) at the sites in which a space exists between shell 106 and existing cardiac ring 110. Its spool shape allows this insert (cf. FIG. 33) to conform as much as possible to the adjacent irregular structures and to ensure a better seal.

Figure 21:
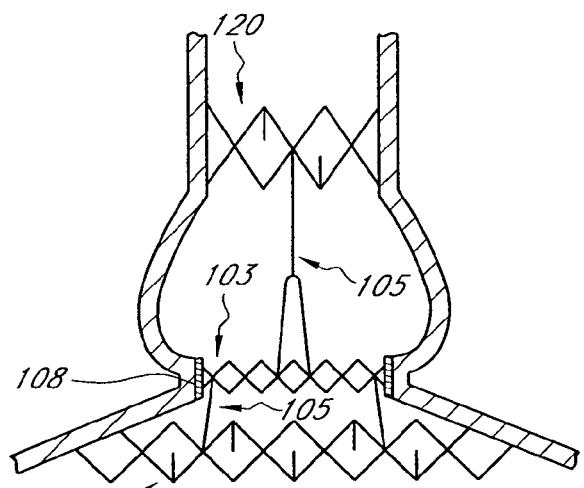
FIG. 21 is a schematic view of the support of FIG. 19 shown in a deployed state.
Figure 34:
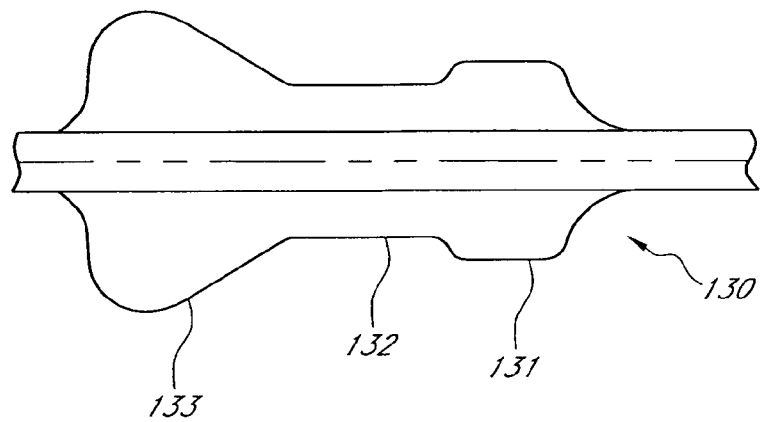
FIG. 34 is a schematic cross-sectional view of a balloon corresponding to the support structure of FIGS. 19 to 21.
Figure 35:
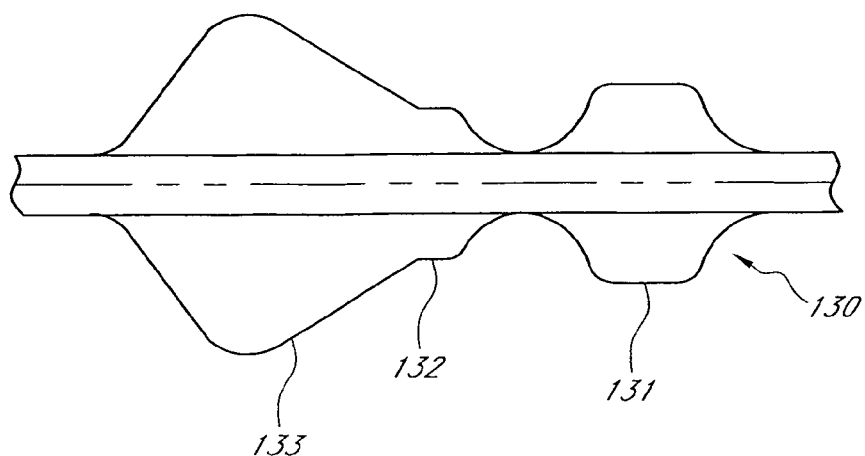
FIG. 35 is a schematic longitudinal sectional view of an alternative embodiment of the balloon of FIG. 34.

FIG. 34 shows balloon 130 making it possible to deploy support 101 according to FIGS. 19 to 21. This balloon 130 has cylindrical portion 131 whose diameter in the inflated state makes possible the expansion of holding portion 120, a cylindrical portion 132 of lesser diameter, suitable for producing the expansion of portion 103, and portion 133 in the form of a truncated cone, makes possible the expansion of portion 104. As shown by FIG. 35, portion 132 can be limited to what is strictly necessary for deploying portion 103, which makes it possible to produce balloon 130 in two parts instead of a single part, thus limiting the volume of this balloon 130.

Figure 36:
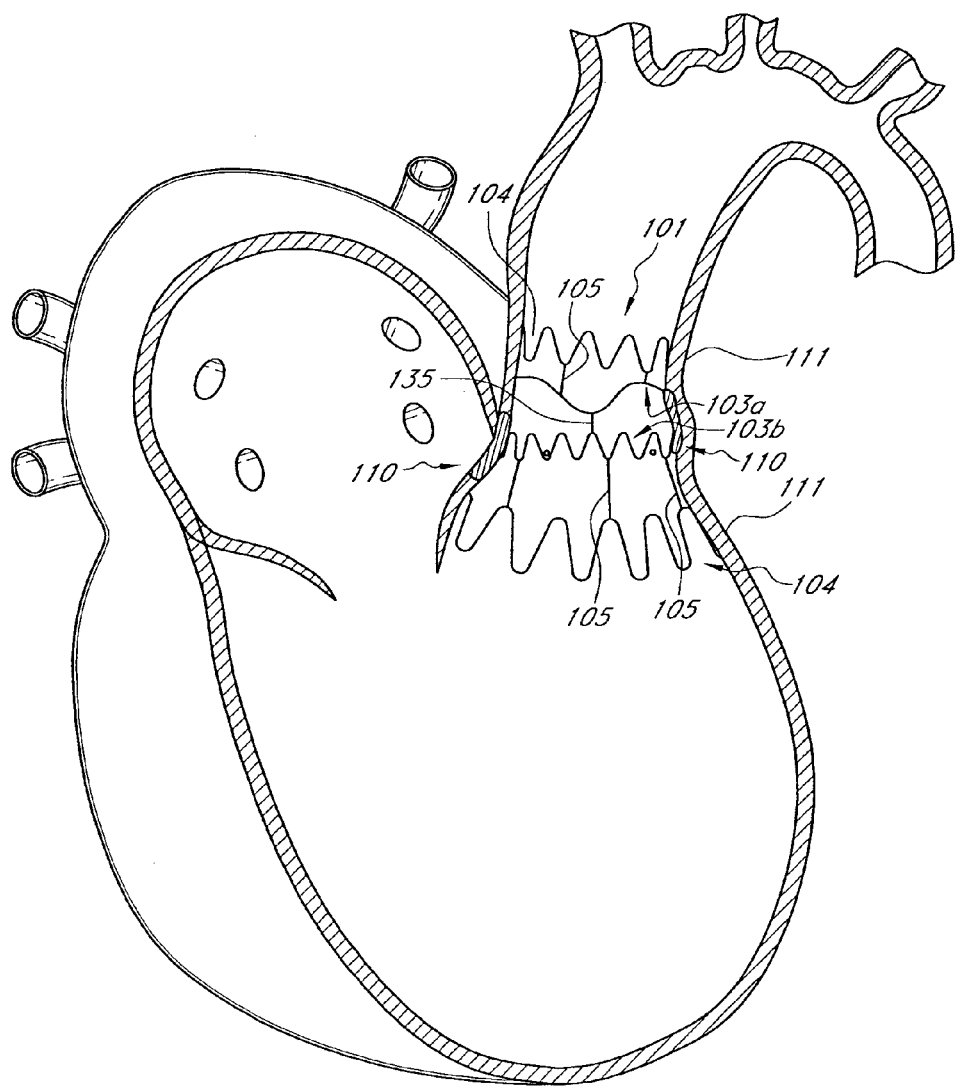
FIG. 36 is a schematic view of a heart with an embodiment of the present inventive prosthesis shown deployed in place.

FIG. 36 shows support 101 whose median portion 103 is in two parts 103a, 103b. Part 103a is made of undulating wire with large-amplitude undulations, in order to support valve 102, and part 103b, adjacent to said part 103a and connected to it by bridges 135, is made of undulating wire with small-amplitude undulations. Due to its structure, this part 103b presents a relatively high radial force of expansion and is intended to be placed opposite ring 110 in order to push back the native valve sheets which are naturally calcified, thickened and indurated, or the residues of the valve sheets after valve resection against or into the wall of the passage. This axial portion 103a, 103b thus eliminates the problem induced by these sheets or residual sheets at the time of positioning of valve 102.

It is apparent from the preceding that one embodiment of the invention provides a tubular support for positioning, by percutaneous route, of a replacement heart valve, which provides, due to its portions 103 and 104, complete certitude as to its maintenance of position after implantation. This support also makes possible a complete sealing of the replacement valve, even in case of a cardiac ring with a surface that is to varying degrees irregular and/or calcified, and its position can be adapted and/or corrected as necessary at the time of implantation.

Figure 37:
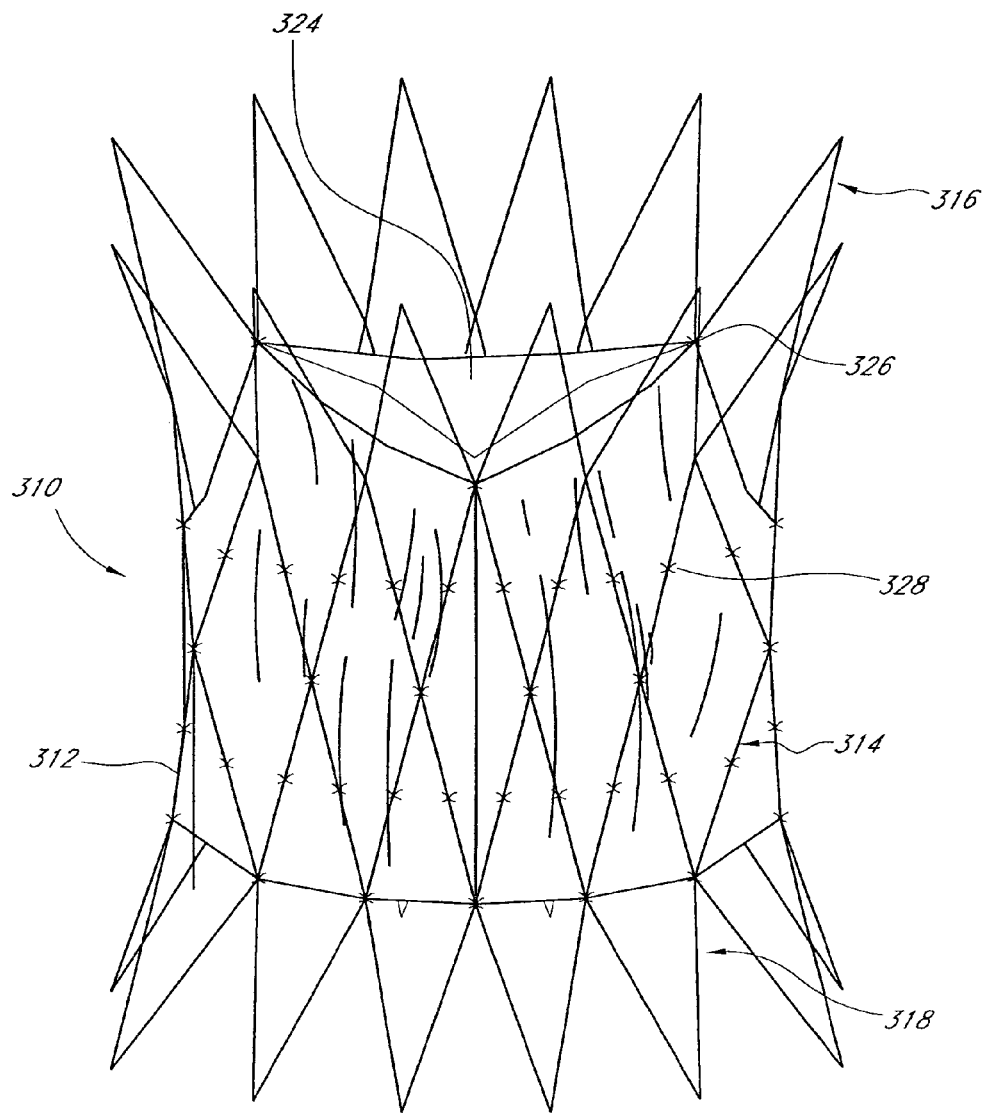
FIG. 37 is a perspective view of one embodiment of a prosthetic valve assembly of the present invention.
Figure 38:
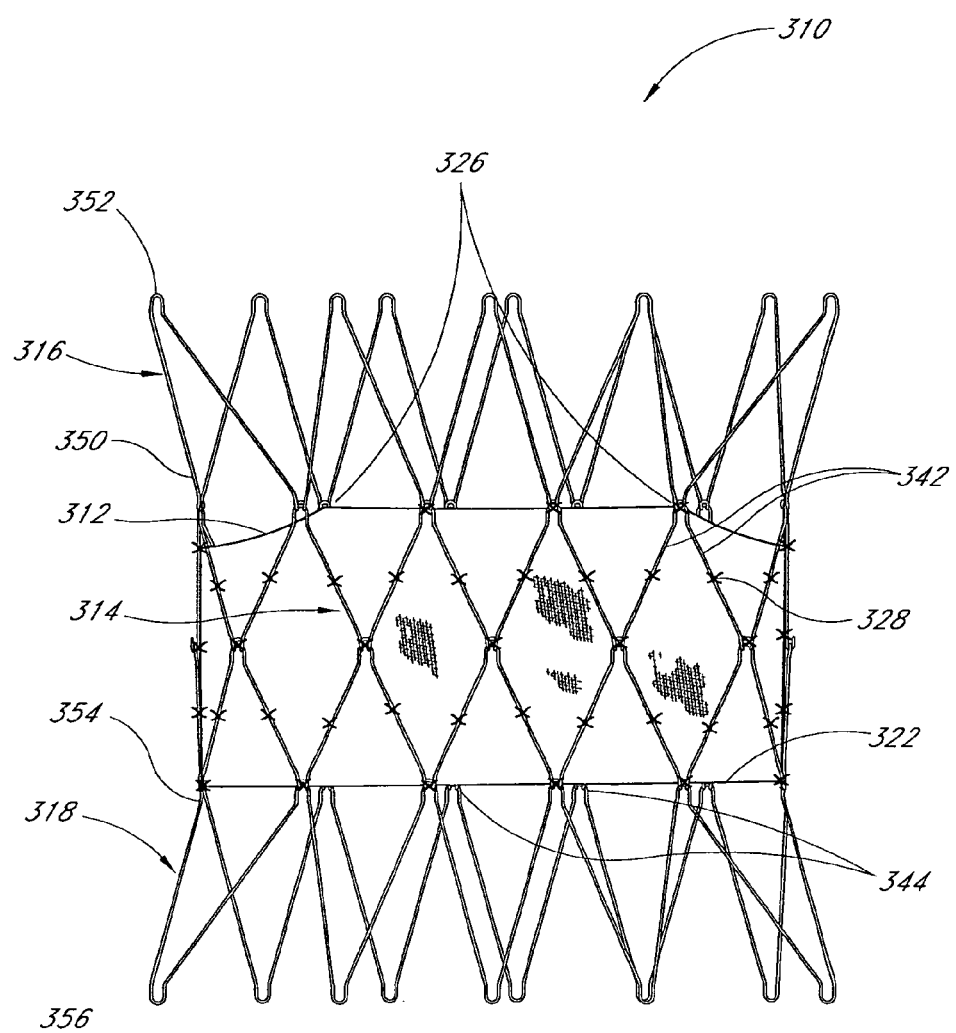
FIG. 38 is a side view of the prosthetic valve assembly of FIG. 37.

Referring to FIGS. 37 and 38, the present invention also comprises an alternative prosthetic valve assembly 310, which further comprises a prosthetic valve 312, a valve support band 314, distal anchor 316, and a proximal anchor 318. Valve 312 can be made from a biological material, such as one originating from an animal or human, or from a synthetic material, such as a polymer. Depending upon the native valve to be replaced, the prosthetic valve 312 comprises an annulus 322, a plurality of leaflets 324 and a plurality of commissure points 326. The leaflets 324 permit the flow of blood through the valve 312 in only one direction. In the preferred embodiment, the valve annulus 322 and the commissure points 326 are all entirely supported within the central support band 314. Valve 312 is attached to the valve support band 314 with a plurality of sutures 328, which can be a biologically compatible thread. The valve could also be supported on band 314 with adhesive, such as cyanoacrylate.

Figure 40:
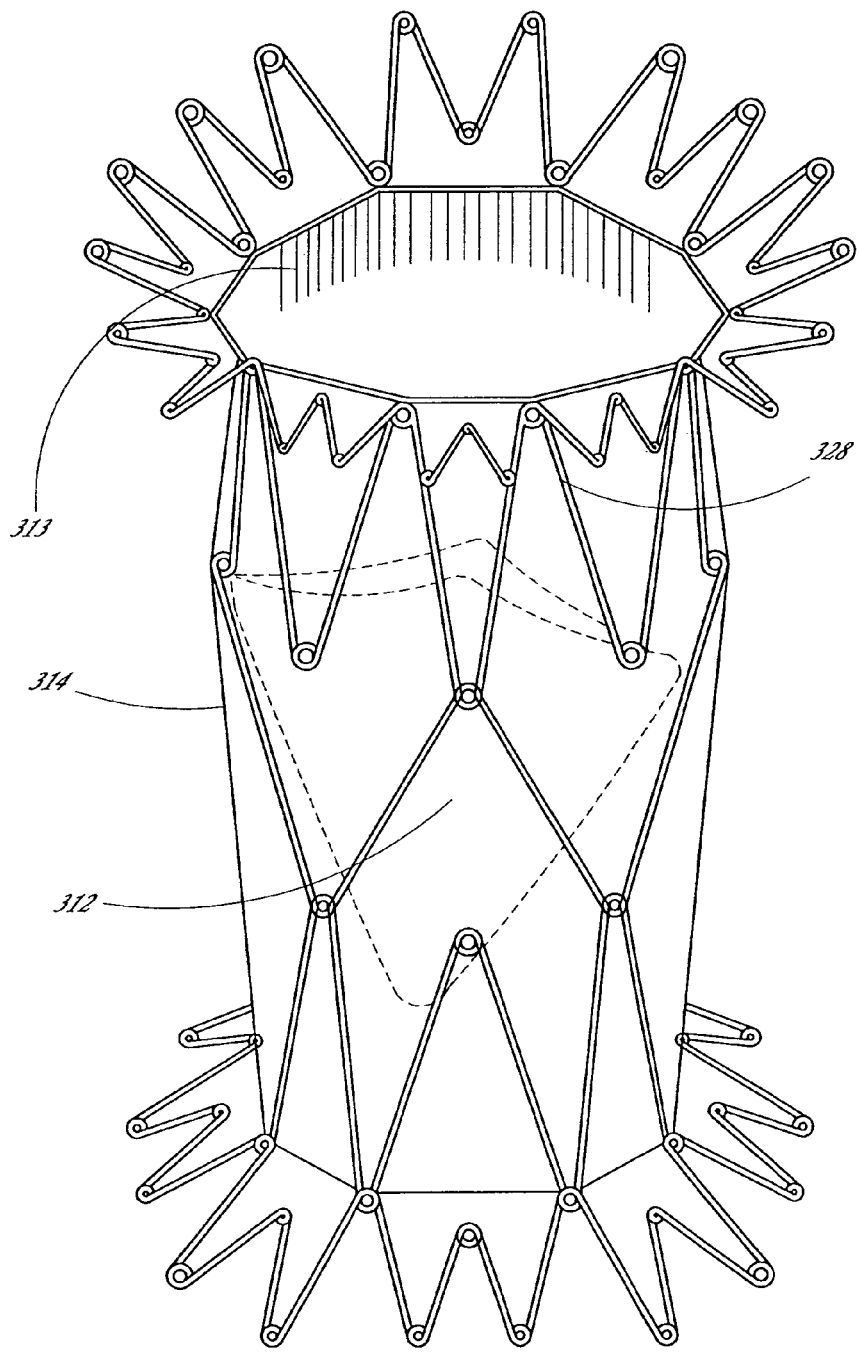
FIG. 40 is a perspective view of an alternative embodiment of the prosthetic valve assembly with a sheath around the valve.

In one embodiment, valve 312 can be attached to, or may integral with, a sleeve or sheath 313. The sheath is secured to the valve support band 314 such that the outer surface of the sheath is substantially in contact with the inner surface of the valve support band 314. In such embodiment, the sheath can be attached to the valve support band 314 with sutures 328. FIG. 40 is a schematic of the concept of this alternative embodiment. If desired, the sheath 313 can be secured to the outside of valve support band 314 (not shown).

Referring to FIGS. 37 and 38, in one embodiment, valve support band 314 is made from a single wire 342 configured in a zigzag manner to form a cylinder. Alternatively, valve support band 314 can be made from a plurality of wires 342 attached to one another. In either case, the band may comprise one or more tiers, each of which may comprise one or more wires arranged in a zigzag manner, for structural stability or manufacturing ease, or as anatomical constraints may dictate. If desired, even where the central valve support 314 is manufactured having more than one tier, the entire valve support 314 may comprise a single wire. Wire 342 can be made from, for example, stainless steel, silver, tantalum, gold, titanium or any suitable plastic material. Valve support band 314 may comprise a plurality of loops 344 at opposing ends to permit attachment to valve support band 314 of anchors 316 and/or 318 with a link. Loops 344 can be formed by twisting or bending the wire 342 into a circular shape. Alternatively, valve support band 314 and loops 344 can be formed from a single wire 342 bent in a zigzag manner, and twisted or bent into a circular shape at each bend. The links can be made from, for example, stainless steel, silver, tantalum, gold, titanium, any suitable plastic material, solder, thread, or suture. The ends of wire 342 can be joined together by any suitable method, including welding, gluing or crimping.

Still referring to FIGS. 37 and 38, in one embodiment, distal anchor 316 and proximal anchor 318 each comprise a discrete expandable band made from one or more wires 342 bent in a zigzag manner similar to the central band. Distal anchor band 316 and proximal anchor band 318 may comprise a plurality of loops 344 located at an end of wire 342 so that distal anchor band 316 and proximal anchor band 318 can each be attached to valve support band 314 with a link. Loop 344 can be formed by twisting or bending the wire 342 into a circular shape. As desired, distal and/or proximal anchors 316, 318 may comprise one or more tiers, as explained before with the valve support 314. Likewise, each anchor may comprise one or more wires, regardless of the number of tiers. As explained above in regard to other embodiments, the distal anchor may be attached to the central valve support band 314 directly, as in FIG. 37, or spaced distally from the distal end of the valve support 314, as shown above schematically in FIGS. 18, 19, 21 and 22. In the later instance, one or more struts may be used to link the distal anchor band to the valve support band, as described above.

Distal anchor band 316 has a first end 350 attached to the central valve band 314, and a second end 352. Similarly, proximal anchor band 318 has first attached end 354 and a second end 356. The unattached ends 352, 356 of the anchors 316, 318, respectively are free to expand in a flared manner to conform to the local anatomy. In such embodiment, the distal and proximal anchor bands 316, 318 are configured to exert sufficient radial force against the inside wall of a vessel in which it can be inserted. Applying such radial forces provides mechanical fixation of the prosthetic valve assembly 310, reducing migration of the prosthetic valve assembly 310 once deployed. It is contemplated, however, that the radial forces exerted by the valve support 314 may be sufficient to resist more than a minimal amount of migration, thus avoiding the need for any type of anchor.

In an alternative embodiment, distal and proximal anchors may comprise a fixation device, including barbs, hooks, or pins (not shown). Such devices may alternatively or in addition be placed on the valve support 314. If so desired, the prosthetic valve assembly 310 may comprise an adhesive on the exterior thereof to adhere to the internal anatomical lumen.

Figure 39:
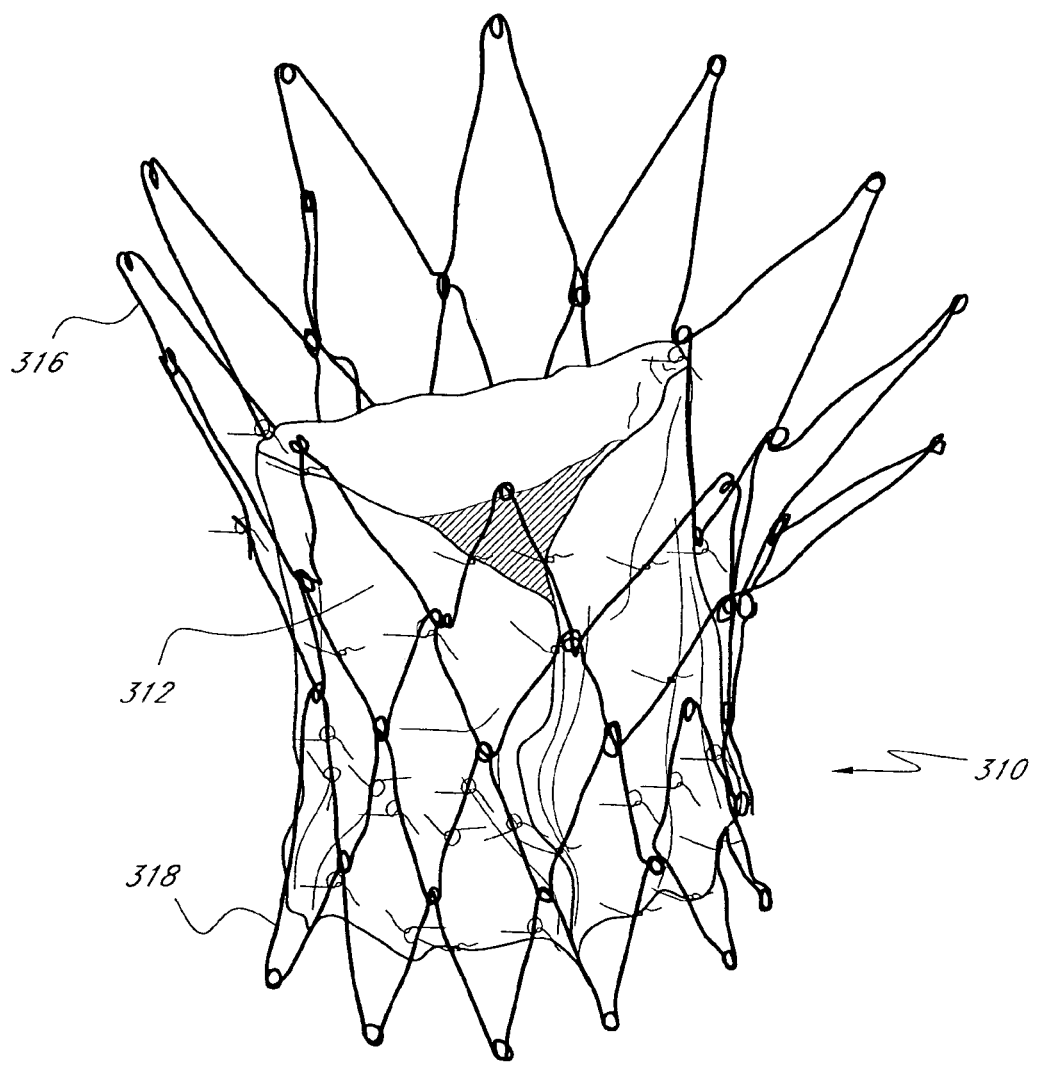
FIG. 39 is a perspective view of one embodiment of the prosthetic valve assembly of FIG. 37.
Figure 49:
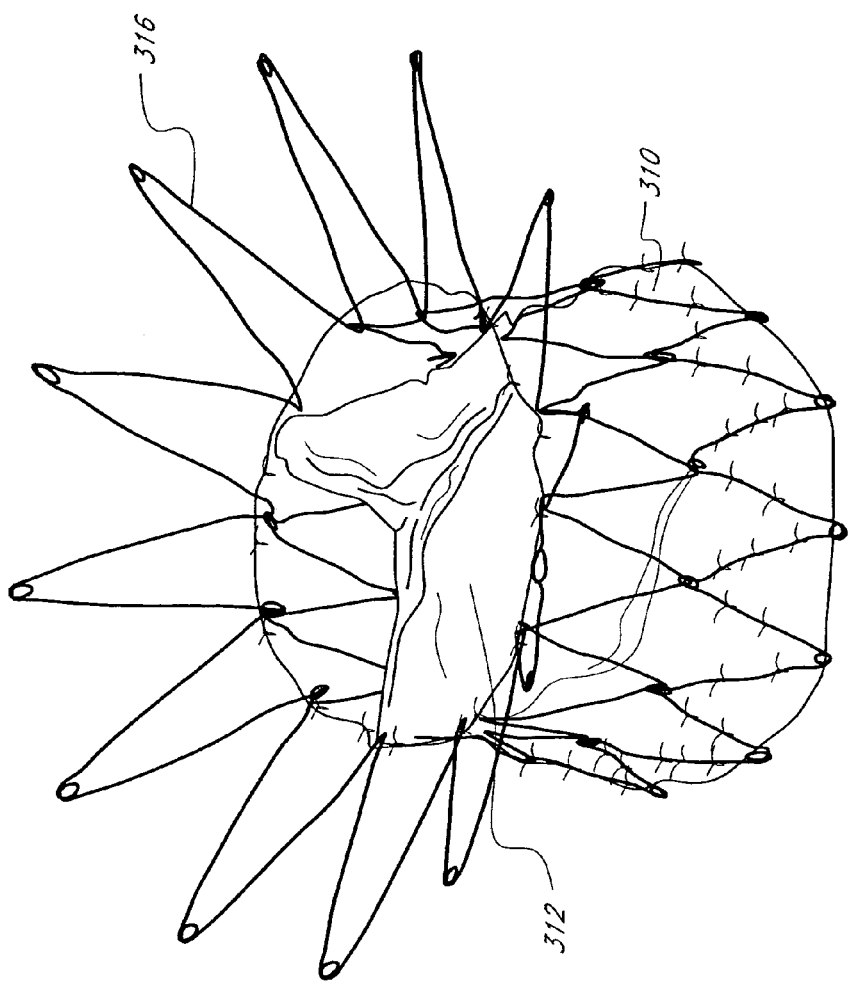
FIG. 49 is a perspective view of an alternative embodiment of the prosthetic valve assembly of FIG. 37 showing a distal anchor.

Prosthetic valve assembly 310 is compressible about its center axis such that its diameter may be decreased from an expanded position to a compressed position. When placed into the compressed position, valve assembly 310 may be loaded onto a catheter and transluminally delivered to a desired location within a body, such as a blood vessel, or a defective, native heart valve. Once properly positioned within the body the valve assembly 310 can be deployed from the compressed position to the expanded position. FIG. 39 is a schematic of one embodiment of the prosthetic valve assembly described with both distal and proximal anchor bands 316, 318 while FIG. 49 is a schematic showing only a distal anchor 316.

In the preferred embodiment, the prosthetic valve assembly 310 is made of self-expanding material, such as Nitinol. In an alternative embodiment, the valve assembly 310 requires active expansion to deploy it into place. Active expansion may be provided by an expansion device such as a balloon.

Figures 41A, 41B:
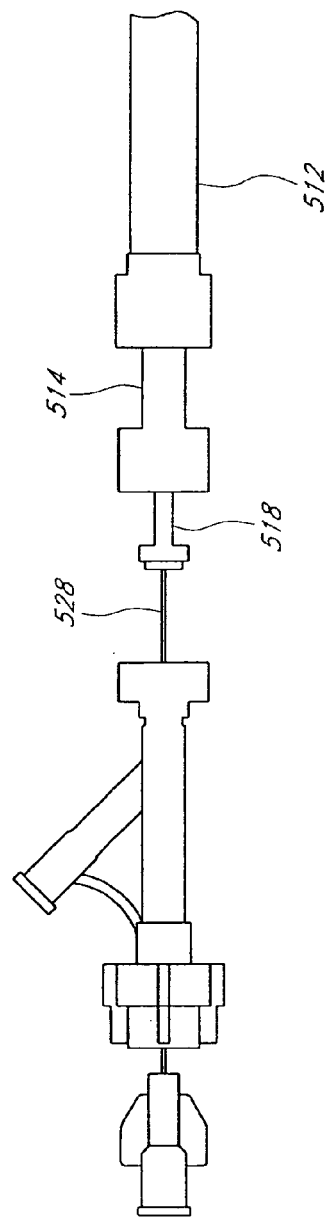
FIG. 41A is a perspective view of a distal portion of a catheter assembly for use in deploying the prosthetic valve assembly described herein.
FIG. 41B is a perspective view of a proximal portion of the catheter assembly of FIG. 41A.
Figure 42:
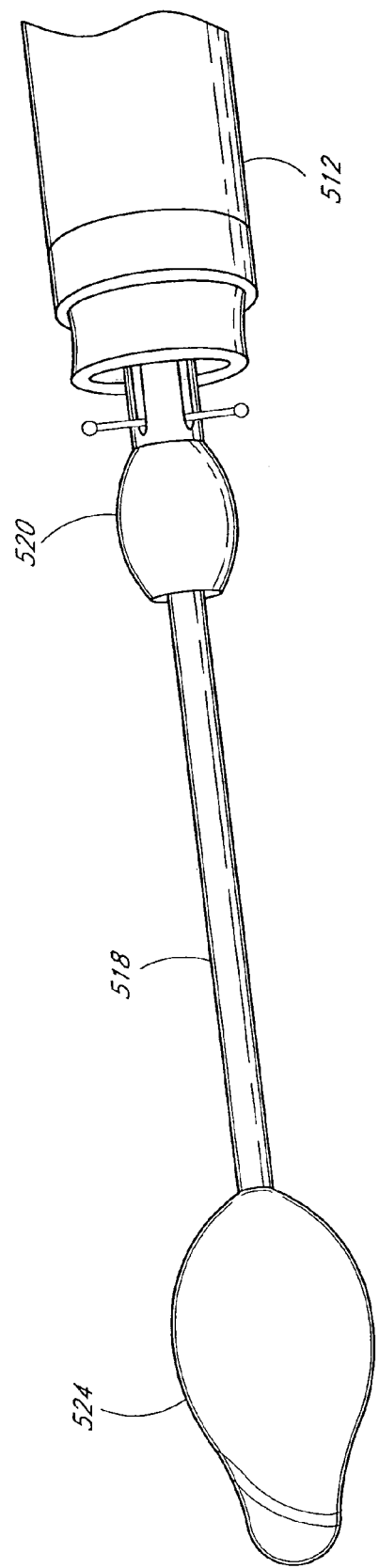
FIG. 42 is a perspective view of the distal portion of the catheter assembly of FIG. 41A.
Figure 43:
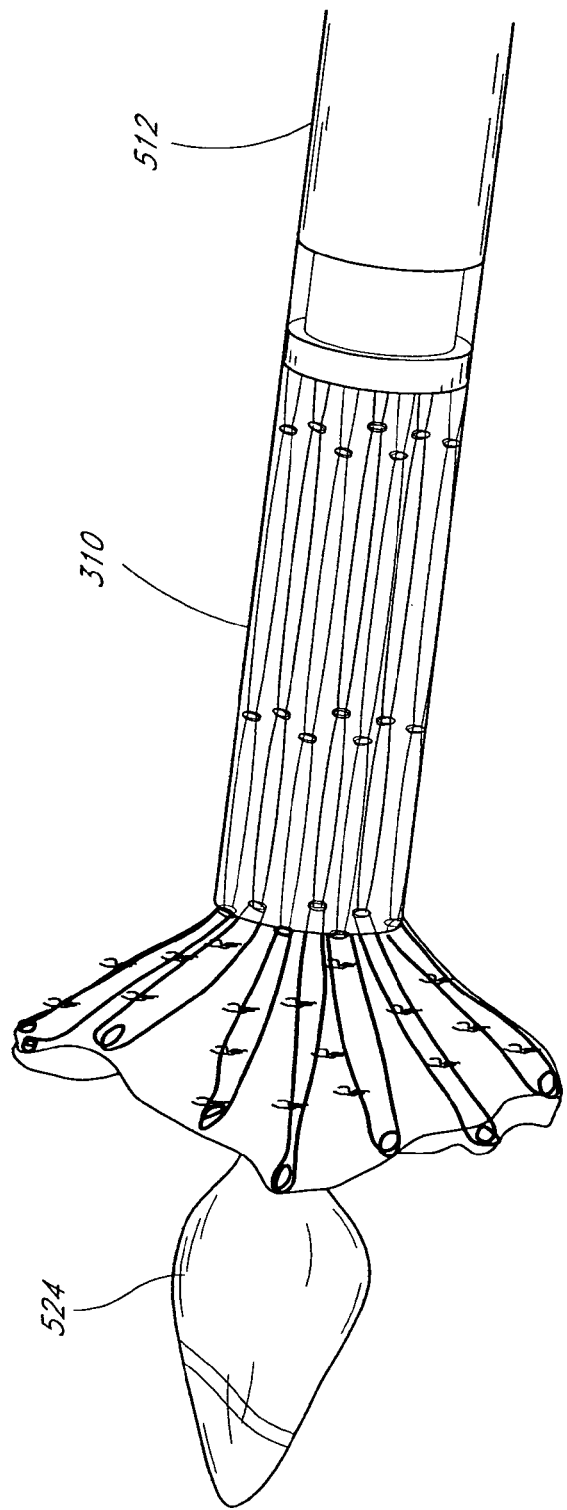
FIGS. 43 through 45 are perspective views of the catheter assembly of FIG. 41A showing deployment of a prosthesis assembly in sequence.
Figure 44:
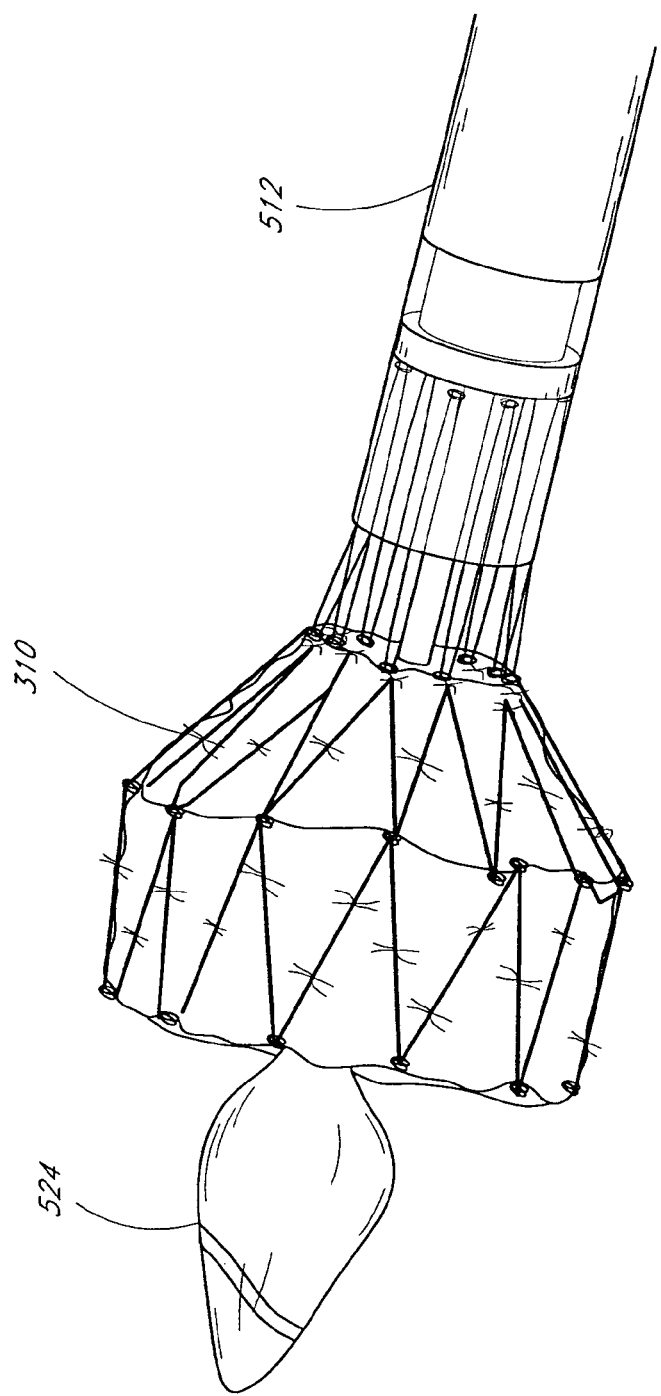
Figure 45:
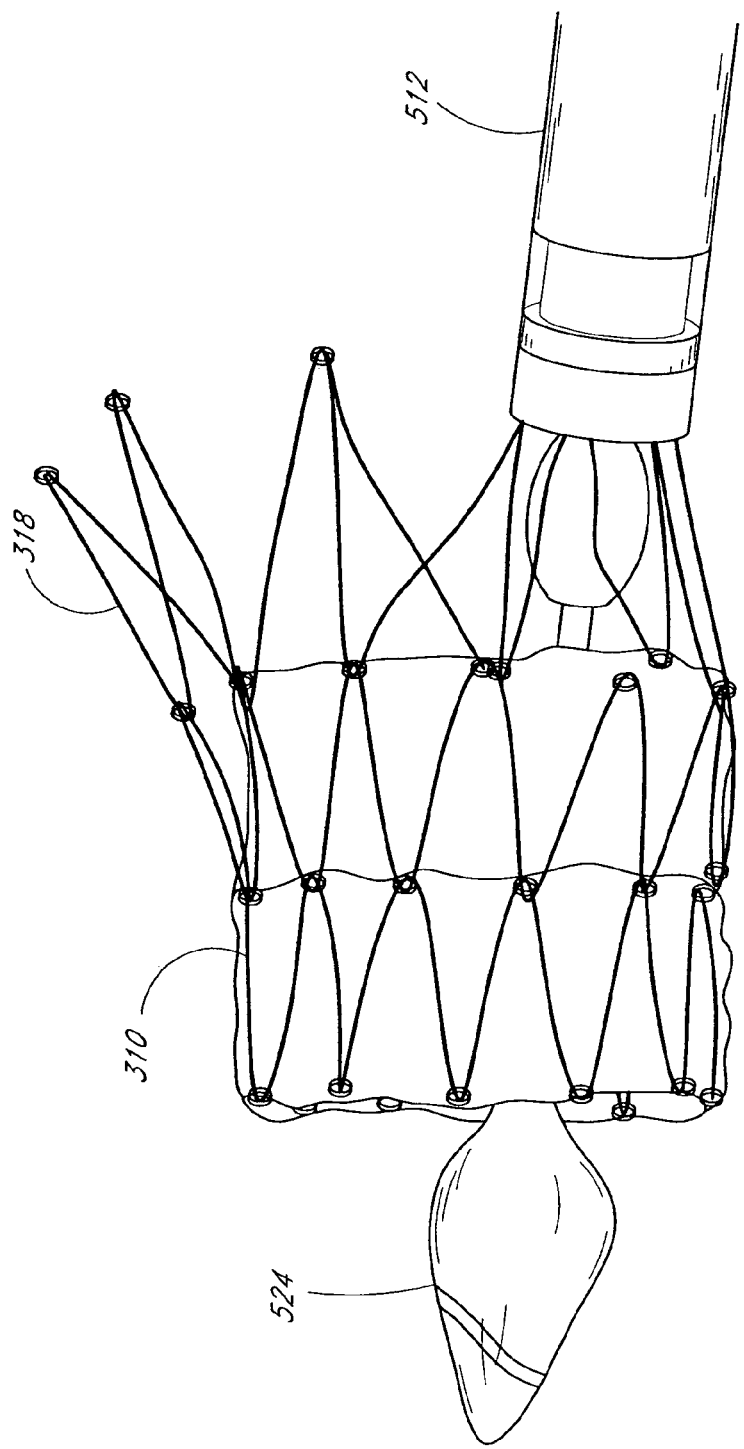

As referred to above in association with other embodiments, the prosthetic valve assembly of the present invention is intended to be percutaneously inserted and deployed using a catheter assembly. Referring to FIG. 41A, the catheter assembly 510 comprises an outer sheath 512, an elongate pusher tube 514, and a central tube 518, each of which are concentrically aligned and permit relative movement with respect to each other. At a distal end of the pusher tube 514 is a pusher tip 520 and one or more deployment hooks 522 for retaining the prosthesis assembly (not shown). The pusher tip 520 is sufficiently large so that a contracted prosthesis assembly engages the pusher tip 520 in a frictional fit arrangement. Advancement of the pusher tube 514 (within the outer sheath 512) in a distal direction serves to advance the prosthesis relative to the outer sheath 512 for deployment purposes.

At a distal end of the central tube 518 is an atraumatic tip 524 for facilitating the advancement of the catheter assembly 510 through the patient's skin and vasculature. The central tube 518 comprises a central lumen (shown in phantom) that can accommodate a guide wire 528. In one embodiment, the central lumen is sufficiently large to accommodate a guide wire 528 that is 0.038 inch in diameter. The guide wire can slide through the total length of the catheter form tip to handle ('over the wire' catheter) or the outer sheath 512 can be conformed so as to allow for the guide wire to leave the catheter before reaching its proximal end ('rapid exchange' catheter). The space between the pusher tube 514 and the outer sheath 512 forms a space within which a prosthetic valve assembly may be mounted.

Hooks 522 on the distal end of the pusher tube 514 may be configured in any desired arrangement, depending upon the specific features of the prosthetic assembly. With regard to the prosthesis assembly of FIGS. 37 and 38, the hooks 522 preferably comprise an L-shaped arrangement to retain the prosthesis assembly axially, but not radially. With a self-expanding assembly, as the prosthesis assembly is advanced distally beyond the distal end of the outer sheath 512, the exposed portions of the prosthesis assembly expand while the hooks 522 still retain the portion of the prosthesis still housed within the outer sheath 512. When the entire prosthesis assembly is advanced beyond the distal end of the outer sheath, the entire prosthesis assembly is permitted to expand, releasing the assembly from the hooks. FIGS. 42 through 45 show the distal end of one embodiment of the catheter assembly, three of which show sequenced deployment of a valve prosthesis.

Figure 46:
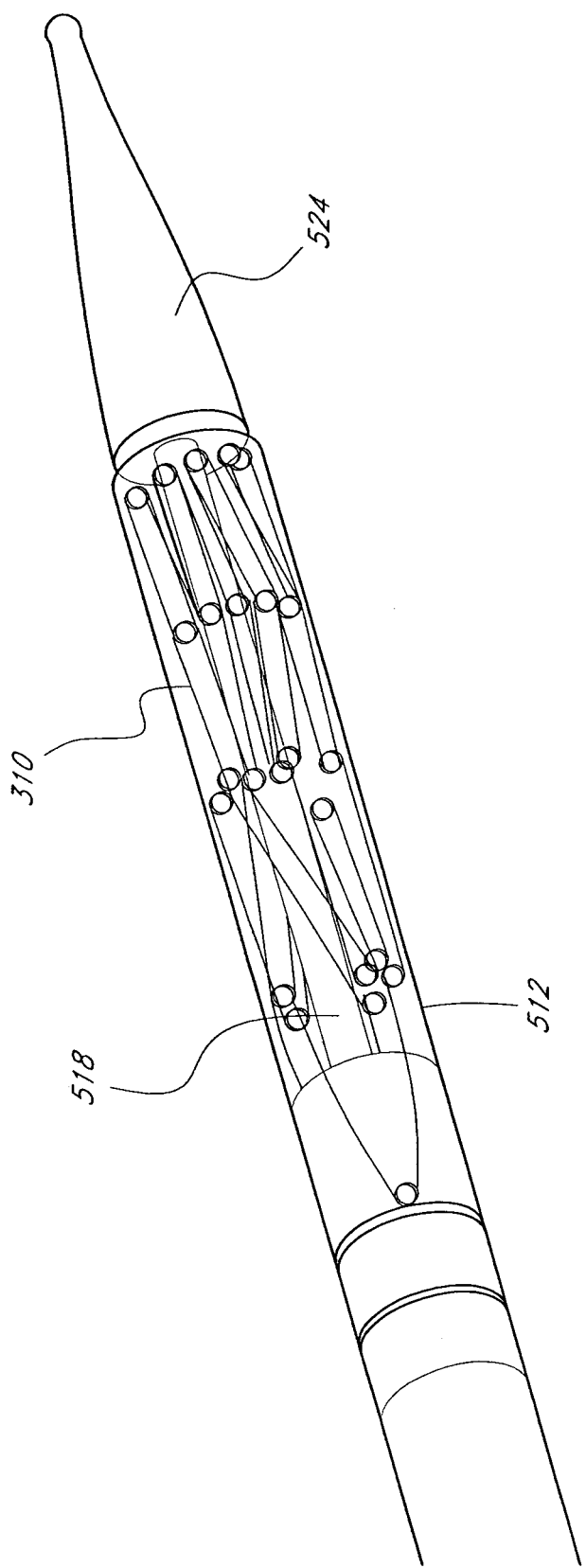
FIGS. 46 and 47 are perspective views of the catheter assembly of FIG. 41A showing deployment of an alternative prosthesis assembly.
Figure 47:
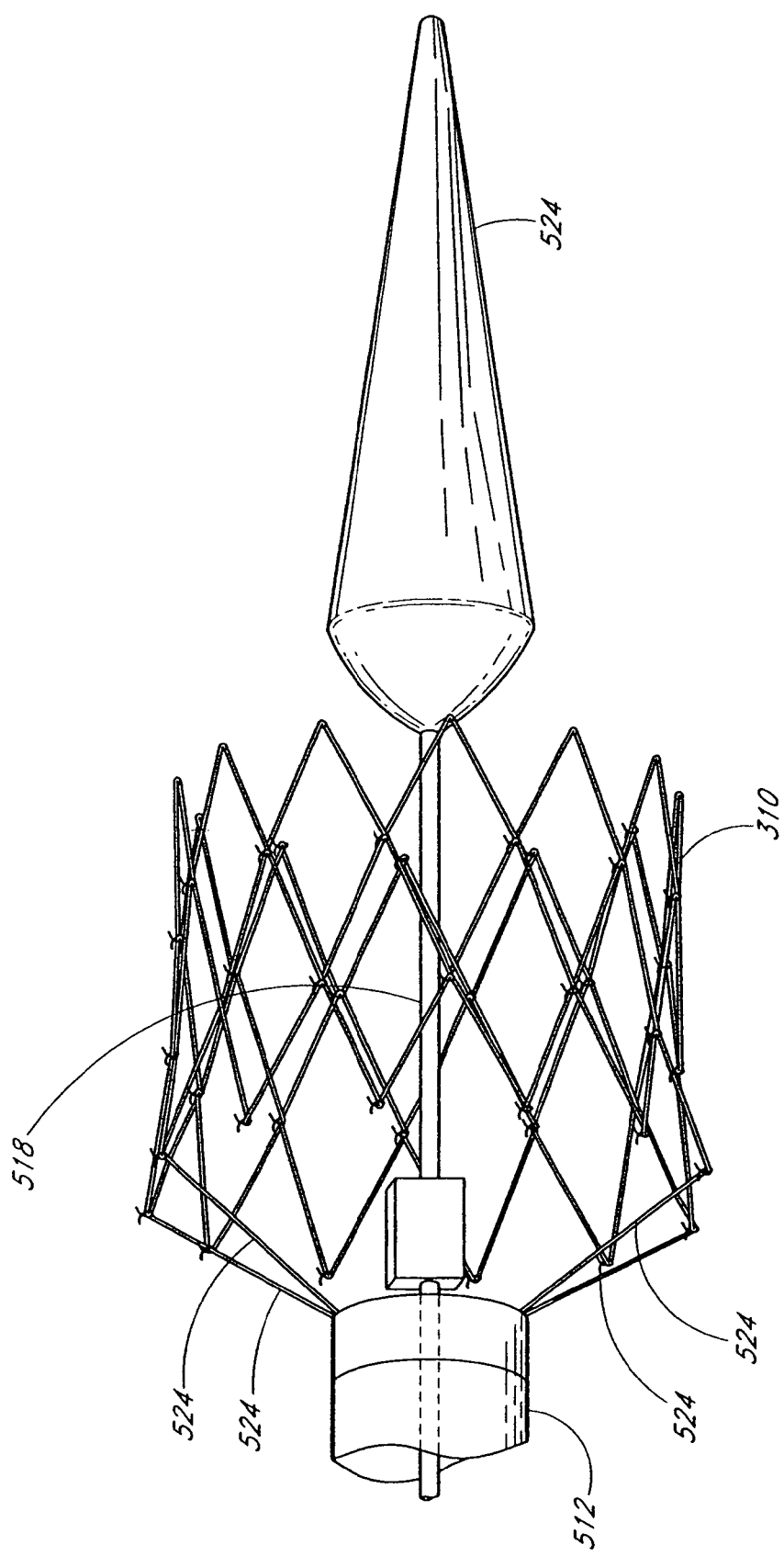
Figure 48:
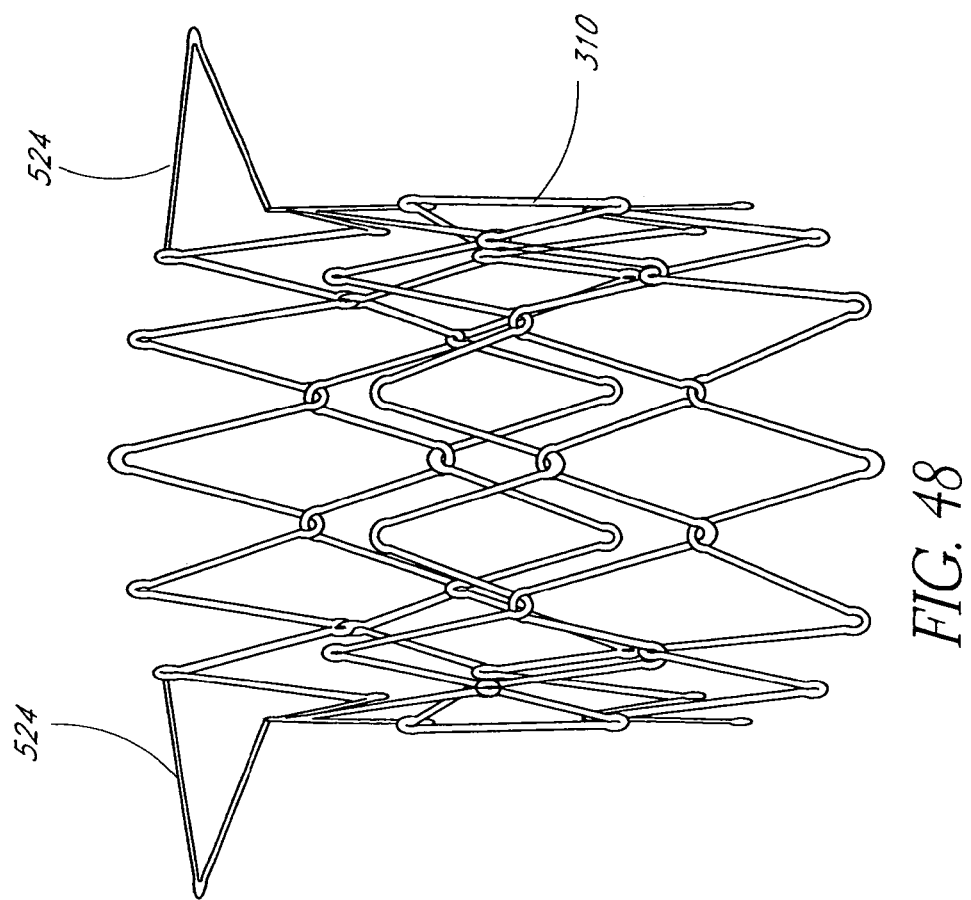
FIG. 48 is a perspective view of the alternative prosthesis assembly shown in FIGS. 46 and 47.
Figure 55:
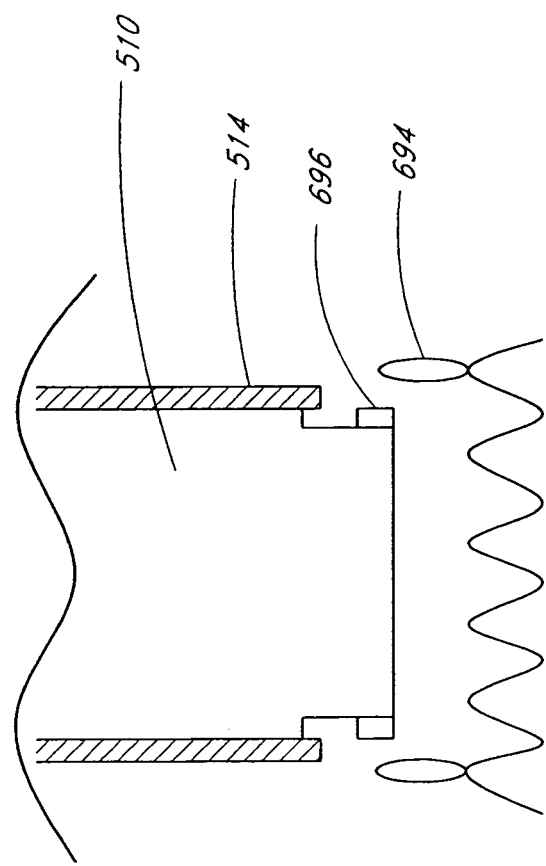
FIG. 55 depicts one embodiment of the present invention comprising loop elements released from a delivery catheter after withdrawal of an outer sheath.

FIG. 48 shows an alternative embodiment of the valve prosthesis, where loop elements extend axially from one end of the prosthesis and are retained by the hooks 522 on pusher tube 514 during deployment. FIGS. 46 and 47 show a catheter assembly used for deploying the alternative prosthesis assembly of FIG. 48. By adding loop elements to the prosthesis, the prosthesis may be positioned with its support and anchors fully expanded in place while permitting axial adjustment into final placement before releasing the prosthesis entirely from the catheter. Referring to FIG. 55, an alternative embodiment of a self-expanding valve prosthesis and delivery system comprises loop elements 694 on prosthetic assembly 310 retained by disks 696 on pusher tube 514 by outer sheath 512. When outer sheath 512 is pulled back to expose disks 696, self-expanding loop elements 694 are then released from pusher tube 514.

FIG. 41B shows the proximal end of the catheter assembly 510 that, to a greater extent, has many conventional features. At the distal end of the pusher tube 514 is a plunger 530 for advancing and retreating the pusher tube 514 as deployment of the prosthesis assembly is desired. As desired, valves and flush ports proximal and distal to the valve prosthesis may be provided to permit effective and safe utilization of the catheter assembly 510 to deploy a prosthesis assembly.

In one embodiment, prosthetic valve assembly 310 (not shown) is mounted onto catheter 510 so that the valve assembly 310 may be delivered to a desired location inside of a body. In such embodiment, prosthetic valve assembly 310 is placed around pusher tip 520 and compressed radially around the tip 520. The distal end of prosthetic valve assembly 310 is positioned on the hooks 522. While in the compressed position, outer sheath 512 is slid toward the atraumatic tip 524 until it substantially covers prosthetic valve assembly 310.

To deliver prosthetic valve assembly 310 to a desired location within the body, a guide wire 528 is inserted into a suitable lumen of the body, such as the femoral artery or vein to the right atrium, then to the left atrium through a transseptal approach, and maneuvered, utilizing conventional techniques, until the distal end of the guide wire 528 reaches the desired location. The catheter assembly 510 is inserted into the body over the guide wire 528 to the desired position. Atraumatic tip 524 facilitates advancement of the catheter assembly 510 into the body. Once the desired location is reached, the outer sheath 512 is retracted permitting the valve prosthesis to be released from within the outer sheath 512, and expand to conform to the anatomy. In this partially released state, the position of prosthetic valve 310 may be axially adjusted by moving catheter assembly 510 in the proximal or distal direction.

It is apparent that the invention advantageously contemplates a prosthesis that may have a non-cylindrical shape, as shown in several earlier described embodiments including but not limited to FIGS. 21, 37-40, 49 and 59. This non-cylindrical shape results from controlling the diameters at some portions of prosthetic valve assembly 310. Referring to FIG. 56A, yet another non-cylindrical prosthesis is shown. Central support band 314 comprises a diameter-restrained portion of valve assembly 310 attached to distal and proximal anchors 316, 318, that comprise discrete self-expandable bands capable of expanding to a flared or frusta-conical configuration. Anchors 316, 318 further accentuate the non-cylindrical shape of central support band 314. FIG. 56A shows one embodiment of the invention for limiting the diameter of portions of the valve assembly 310 from excessive expansion, whereby valve assembly 310 further comprises a radial restraint 690 to limit the diameter of central support band 314. Radial restraint, as used herein, shall mean any feature or process for providing a desired diameter or range of diameters, including but not limited to the selection of materials or configurations for valve assembly 310 such that it does not expand beyond a preset diameter. Controlling radial expansion to a preset diameter at central support band 314 helps maintain the coaptivity of valve 312 and also preserves the patency of the coronary ostia by preventing central support band 314 from fully expanding to the lumen or chamber wall to cause occlusion. Restraint 690 may be sufficiently flexible such that restraint 690 may contract radially with valve assembly 310, yet in the expanded state resists stretching beyond a set limit by the radial expansion forces exerted by a self-expanding valve assembly 310 or from a balloon catheter applied to valve assembly 310. Referring to FIG. 56A and 56B, restraint 690 may take any of a variety of forms, including wires 700 of a specified length that join portions of central support band 314. Threads may also be used for radial restraint 690. The slack or bends in the wires allow a limited radial expansion to a maximum diameter. Once the slack is eliminated or the bends are straightened, further radial expansion is resisted by tension created in wires 700. These wires may be soldered, welded or interwoven to valve assembly 310. By changing the length of wire joining portions of valve assembly 310, radial restraints of different maximum diameters are created. For example, by using short wires to form the radial restraint, the valve support structure may expand a shorter distance before tension forms in the short wires. If longer wires are used, the support structure may expand farther before tension develops in the longer wires.

Figure 57:
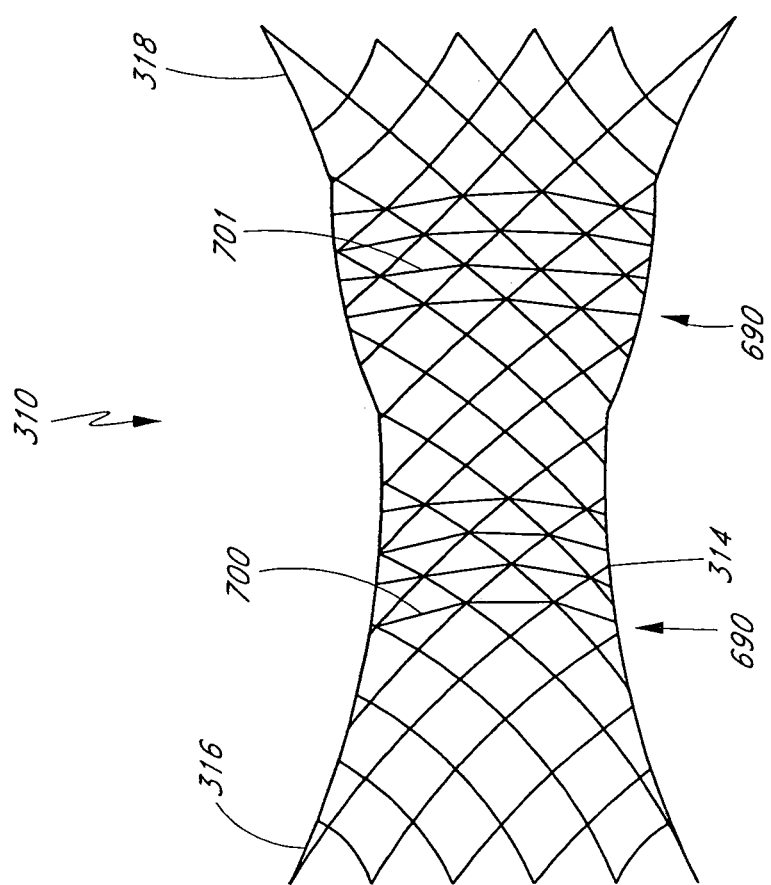
FIG. 57 depicts another embodiment of the invention wherein two radial restraints of different size are attached to different portions of the support structure.
Figure 58:
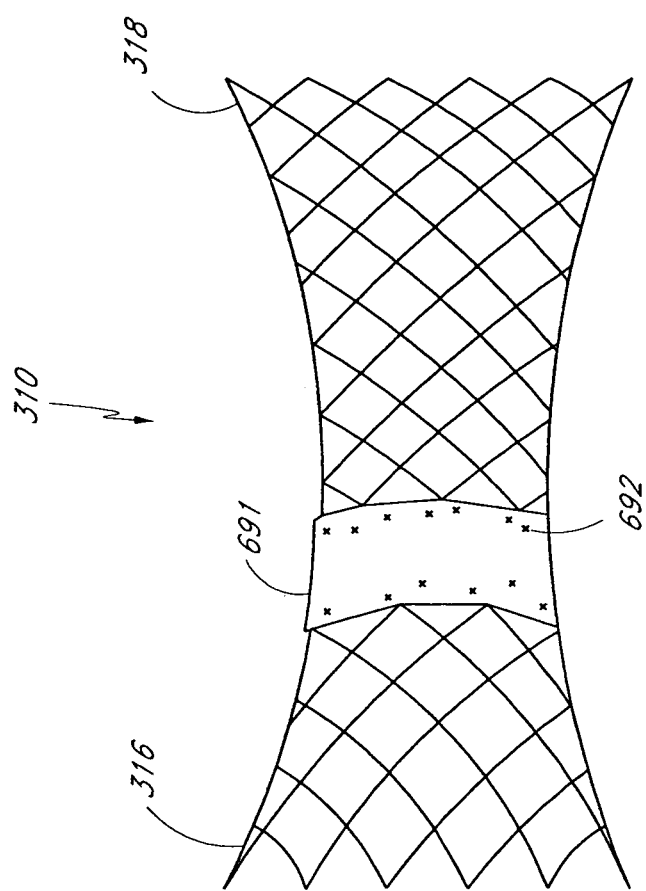
FIG. 58 represents one embodiment of the radial restraint comprising a cuff-type restraint.

FIG. 57 depicts central support band 314 with a radial restraint 700 of a smaller diameter and another portion of the same valve assembly 310 with longer lengths of wire 701 and allowing a larger maximum diameter. The portion of valve assembly 310 with the larger diameter can be advantageously used to allow greater dilation around cardiac ring 110 and native valve sheets. The degree of resistance to expansion or recollapse can be altered by changing the diameter of the radial restraint or by changing the configuration of the restraint. For example, a cross-linked radial restraint will have a greater resistance to both expansion and recollapse. Referring to FIG. 58, restraint 690 may alternatively comprise a cuff 691 encompassing a circumference of central support band 314 that resists expansion of central support band 314 beyond the circumference formed by cuff 691. Cuff 691 may be made of ePTFE or any other biocompatible and flexible polymer or material as is known to those skilled in the art. Cuff 691 may be attached to valve assembly 310 by sutures 692 or adhesives.

Figure 71:
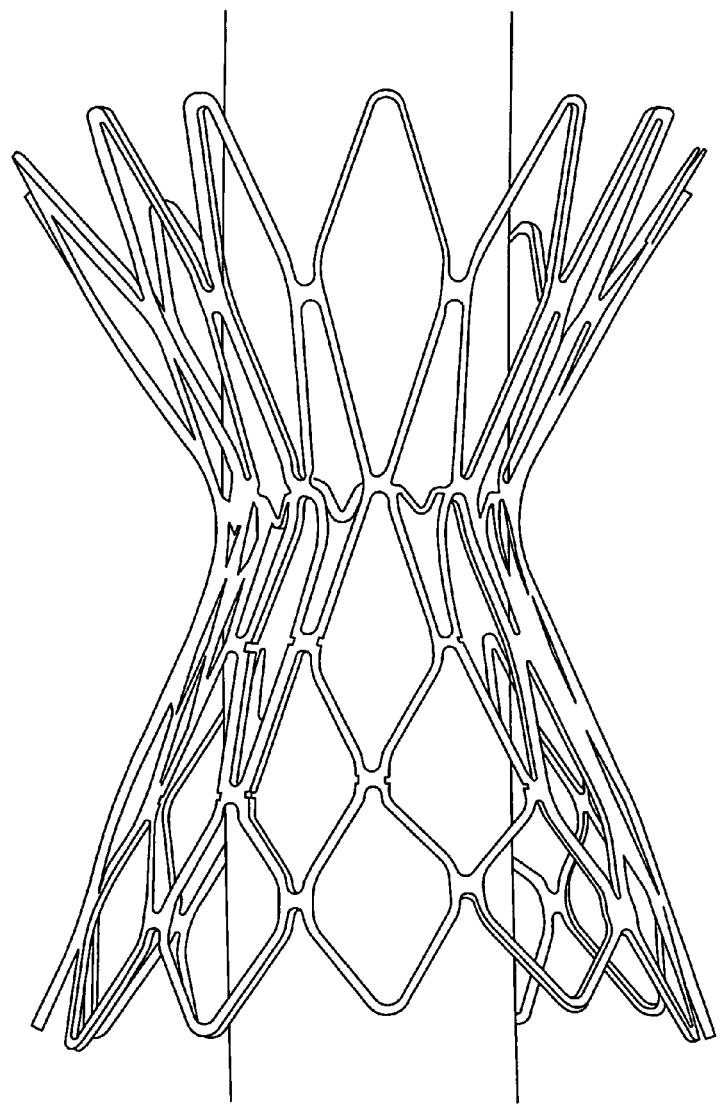
FIG. 71 is a photograph of a valve assembly with radial restraints integrally formed by laser cutting.
Figure 72A:
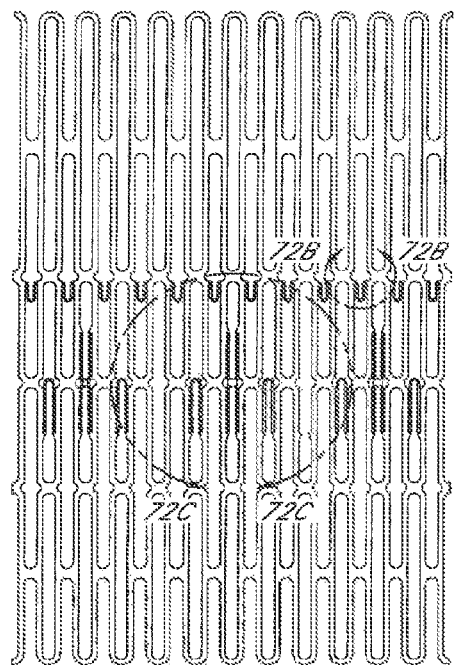
FIGS. 72A through 72C are schematic views of a portion of a valve assembly with different radial restraints formed by laser cutting.
Figure 72B:
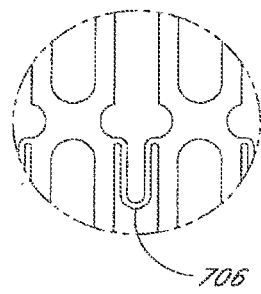
Figure 72C:
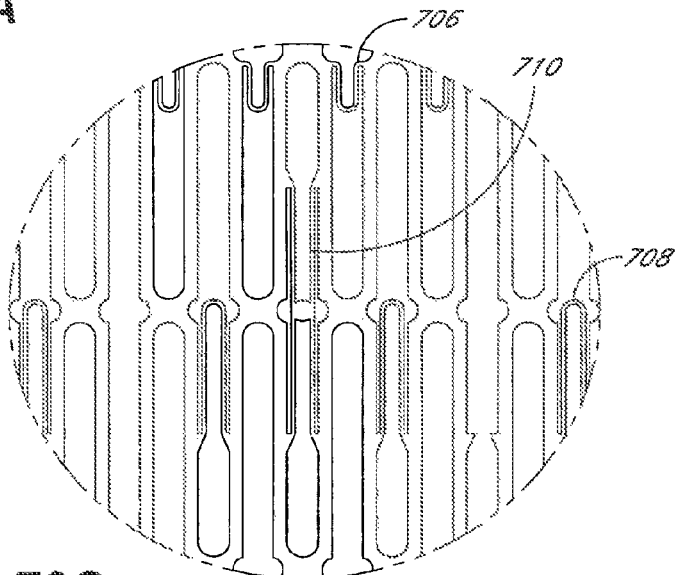
Figure 73A:
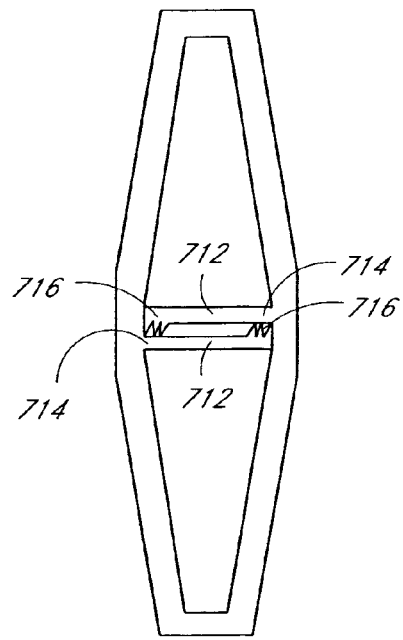
FIGS. 73A through 73E are schematic views of another embodiment of a laser cut anti-recoil feature, in various states of expansion.
Figure 73B:
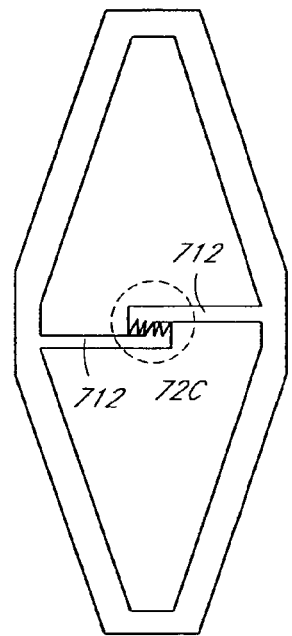
Figure 73C:
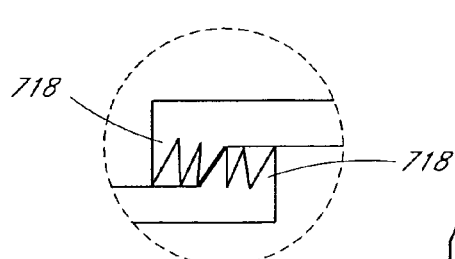
Figure 73D:
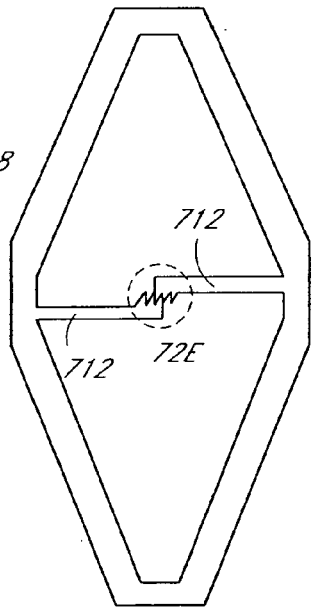
Figure 73E:
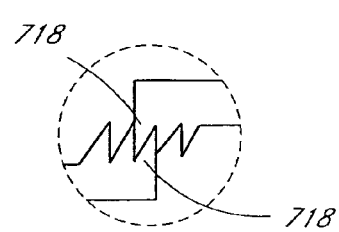

FIG. 71 illustrates one embodiment of the invention where radial restraints are integrally formed as part of valve assembly 310 by using a laser cutting manufacturing process, herein incorporated by reference. FIG. 72A depicts a schematic view of a laser-cut portion of valve assembly 310 in the unexpanded state with several radial restraints 706, 708, 710. Each end of radial restraints 706, 708, 710 is integrally formed and attached to valve assembly 310. An integrally formed radial restraint may be stronger and may have a lower failure rate compared to radial restraints that are sutured, welded or soldered to valve assembly 310. FIG. 72B depicts a shorter radial restraint 706 along one circumference of valve assembly 310. FIG. 72C depicts another portion of valve assembly 310 with a longer radial restraint 708 and a cross-linked radial restraint 710 positioned along the same circumference. Thus, the segments of a radial restraint along a given circumference need not have the same characteristics or size.

Another embodiment of the radial restraint comprises at least one protrusion extending from valve assembly 310 to provide a mechanical stop arrangement. The mechanical stop arrangement restricts radial expansion of valve assembly 310 by using the inverse relationship between the circumference of valve assembly 310 and the length of valve assembly 310. As valve assembly 310 radially expands, the longitudinal length of valve assembly 310 may contract or compress as the diameter of valve assembly 310 increases, depending upon the particular structure or configuration used for valve assembly 310. For example, FIGS. 37, 38, 56A, 57 and 71 depict embodiments of the invention wherein valve assembly 310 comprises a diamond-shaped mesh. The segments of the mesh have a generally longitudinal alignment that reorient to a more circumferential alignment during radial expansion of valve assembly 310. By limiting the distance to which valve assembly 310 can compress in a longitudinal direction, or by restricting the amount of angular reorientation of the wires of valve assembly 310, radial expansion in turn may be controlled to a pre-set diameter. FIG. 74A shows one embodiment of the mechanical stop arrangement comprising an angular stop 730 and an abutting surface 732 on the wire structure of valve assembly 310. A plurality of stops 730 and abutting surfaces 732 may be used along a circumference of valve assembly 310 to limit expansion to a preset diameter. Angular stop 730 may be located between two adjoining portions of valve assembly 310 forming an angle that reduces with radial expansion. As shown in FIG. 74B, as valve assembly 310 radially expands, angular stop 730 will come in closer proximity to surface 732 and eventually abut against surface 732 to prevent further diameter expansion of valve assembly 310. The angular size 734 of stop 730 can be changed to provide different expansion limits. The radial size 736 of stop 730 can also be changed to alter the strength of stop 730. One skilled in the art will understand that many other configurations may be used for valve assembly 310 besides a diamond-shape configuration. For example, FIGS. 15 and 16 depict support 101 with an undulating wire stent configuration that exhibits minimal longitudinal shortening when expanding. The mechanical stop arrangements described above may be adapted by those skilled in the art to the undulating wire stent configuration, or any other stent configuration, for controlling the diameter of the support structure or valve assembly 310.

The particular method of maintaining the valve diameter within a preset range described previously relates to the general concept of controlling the expanded diameter of the prosthesis. The diameter attained by a portion of the prosthesis is a function of the radial inward forces and the radial expansion forces acting upon that portion of the prosthesis. A portion of the prosthesis will reach its final diameter when the net sum of these forces is equal to zero. Thus, controlling the diameter of the prosthesis can be addressed by changing the radial expansion force, changing the radial inward forces, or a combination of both. Changes to the radial expansion force generally occur in a diameter-related manner and can occur extrinsically or intrinsically. Radial restraint 690, cuff 691 and mechanical stop 730 of FIGS. 56A, 58 and 74A, respectively, are examples of extrinsic radial restraints that can limit or resist diameter changes of prosthetic valve assembly 310 once a preset diameter is reached.

Other ways to control diameter may act intrinsically by controlling the expansion force so that it does not expand beyond a preset diameter. This can be achieved by the use of the shape memory effect of certain metal alloys like Nitinol. As previously mentioned, when a Nitinol prosthesis is exposed to body heat, it will expand from a compressed diameter to its original diameter. As the Nitinol prosthesis expands, it will exert a radial expansion force that decreases as the prosthesis expands closer to its original diameter, reaching a zero radial expansion force when its original diameter is reached. Thus, use of a shape memory alloy such as Nitinol is one way to provide an intrinsic radial restraint. A non-shape memory material that is elastically deformed during compression will exhibit similar diameter-dependent expansion forces when returning to its original shape.

The other way of controlling diameter mentioned previously is to alter the radial inward or recoil forces acting upon the support or prosthesis. Recoil forces refer to any radially inward force acting upon the valve assembly that prevents the valve support from maintaining a desired expanded diameter. Recoil forces include but are not limited to radially inward forces exerted by the surrounding tissue and forces caused by elastic deformation of prosthetic valve assembly 310. Countering or reducing recoil forces help to ensure deployment of prosthetic valve assembly 310 to the desired diameter or diameter range, particularly at the native valve. For example, when the prosthetic valve assembly 310 of FIGS. 37, 38, 56A, 57 and 58 is deployed, some recoil or diameter reduction may occur that can prevent portions of valve assembly 310 from achieving it pre-set or desired diameter. This recoil can be reduced by applying an expansion force, such as with a balloon, that stresses the material of valve assembly 310 beyond its yield point to cause plastic or permanent deformation, rather than elastic or transient deformation. Similarly, balloon expansion can be used to further expand a self-expanded portion of valve assembly 310 where radially inward anatomical forces have reduced the desired diameter of that portion. Balloon expansion of a self-expanded portion of valve assembly 310 beyond its yield point provides plastic deformation to a larger diameter.

In addition to the use of a balloon catheter to deform valve assembly 310 beyond its yield point, other means for reducing recoil are contemplated. In the preferred embodiment of the invention, a separate stent may be expanded against cardiac ring 110 in addition or in place of valve assembly 310. The separate stent may further push back the native valve sheets or residues of the resected valve and reduce the recoil force of these structures on valve assembly 310. If the separate stent is deployed against cardiac ring 110 prior to deployment of valve assembly 310, a higher radial force of expansion is exerted against ring 110 without adversely affecting the restrained radial force of expansion desired for the central support band 314 supporting valve 312. Alternatively, the separate stent may be deployed after valve assembly 310 and advantageously used to reduce the recoil of valve assembly 310 caused by the elastic deformation of the material used to form valve assembly 310. The separate stent may be self-expanding or balloon-expandable, or a combination thereof.

Another means for addressing recoil involves providing the radial restraint and mechanical stop arrangements previously described with an additional feature that forms an interference fit when the valve assembly 310 is at its preset diameter. By forming an interference fit, the radial restraint or mechanical stop will resist both further expansion and recollapse from recoil. FIGS. 73A through 73E depict an embodiment of a radial restraint with a recoil-resistant configuration integrally formed with valve assembly 310. In this embodiment, each segment of the radial restraint comprises a pair of protrusions 712 having a proximal end 714 and a distal end 716. Proximal end 714 is integrally formed and attached to valve assembly 310 while distal end 716 is unattached. Each pair of protrusions 712 is configured so that distal end 716 of one protrusion 712 is in proximity to the proximal end 714 of other protrusion 712 in the unexpanded state, and where distal ends 716 come close together as valve assembly 310 radially expands. Distal ends 716 comprise a plurality of teeth 718 for providing an interference fit between distal ends 716 upon contact with each other. The interference fit that is formed will resist both further radial expansion and collapse of valve assembly 310. As mentioned earlier, collapse may result from the inherent elastic properties of the materials used for valve assembly 310 or from radially inward forces exerted by the tissue surrounding valve assembly 310. The interference fit may be provided over a range of expansion, as depicted in FIGS. 72B and 72C from the self-expanded state through the extra-expanded state. This allows the inference fit to act even when a self-expanded valve assembly 310 is further expanded by a balloon catheter to an extra-expanded state as the expansion diameter is further adjusted. The lengths of protrusions 712 will determine the amount of radial restraint provided. Shorter protrusions 712 have distal ends 716 that contact each other after a shorter distance of radial expansion, while longer protrusions 712 will form an interference fit after a longer distance.

FIGS. 75A and 75B depict another embodiment of a radial restraint with a recoil resistant feature. Angular stop 730 from FIGS. 74A and 74B is provided with a notch 736 that forms an interference fit with a latch 738 protruding from valve assembly 310 adjacent to surface 732. As valve assembly 310 expands, angular stop 730 will eventually abut against to surface 732 to prevent further expansion. Latch 738 will also move closer to notch 736 as valve assembly 310 expands. When the preset diameter is reached, latch 738 forms an interference fit with notch 736 that resists collapse to a smaller diameter. It is contemplated that a balloon catheter may be used to expand valve assembly 310 to the desired diameter and to engage latch 738 to notch 736.

Figure 59:
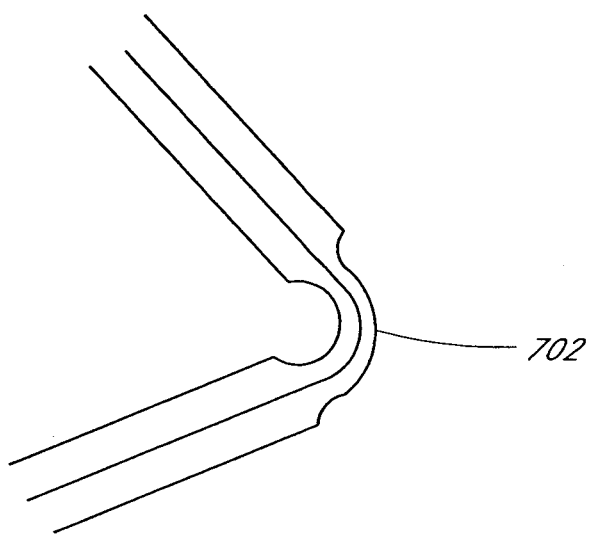
FIG. 59 is a schematic view of a wire bend with a symmetrically reduced diameter.
Figure 60:
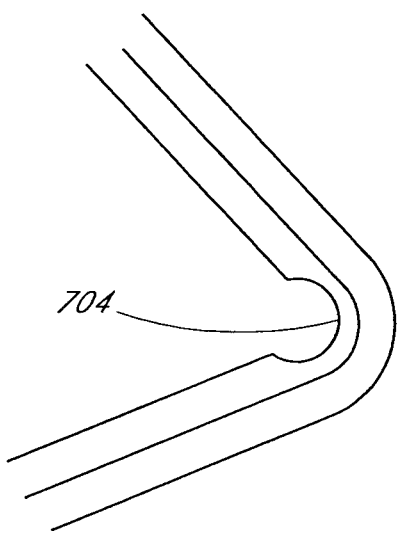
FIG. 60 is a schematic view of an alternative embodiment of a wire bend with an asymmetrically reduced diameter.

Although both shape memory and non-shape memory based prostheses provide diameter-dependent expansion forces that reach zero upon attaining their original shapes, the degree of force exerted can be further modified by altering the thickness of the wire or structure used to configure the support or prosthesis. A prosthesis can be configured with thicker wires to provide a greater expansion force to resist, for example, greater radial inward forces located at the native valve site, but the greater expansion force will still reduce to zero upon the prosthesis attaining its preset diameter. Changes to wire thickness need not occur uniformly throughout a support or prosthesis. Wire thickness can vary between different circumferences of a support or prosthesis, or between straight portions and bends of the wire structure. As illustrated in FIG. 59, the decreased diameter 702 may be generally symmetrical about the longitudinal axis of the wire. Alternatively, as in FIG. 60, the decreased diameter 704 may be asymmetrical, where the diameter reduction is greater along the lesser curvature of the wire bend or undulation relative to the longitudinal axis of the wire. At portions of the prosthesis where the exertion of a particular expansion force against surrounding tissue has importance over the actual diameter attained by that portion of the prosthesis, the various methods for controlling diameter can be adapted to provide the desired expansion force. These portions of the prosthesis may include areas used for anchoring and sealing such as the axial wedging portions or anchors previously described.

Figure 62:
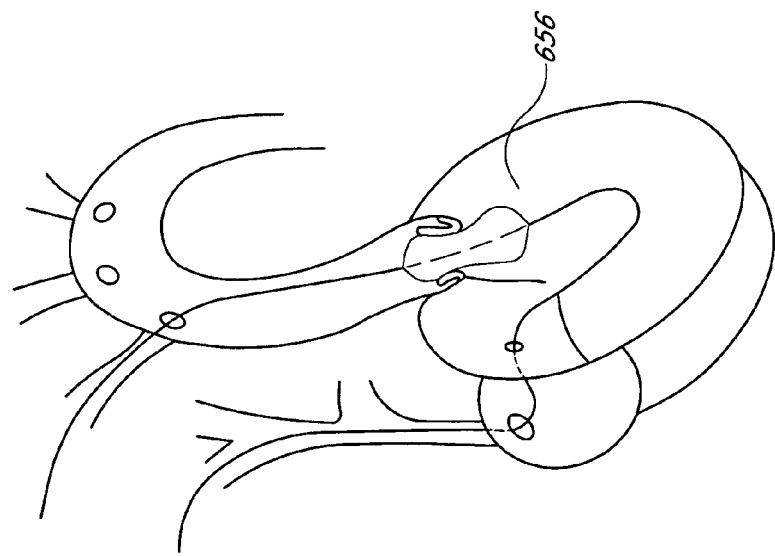
FIG. 62 is a schematic view of a balloon catheter passed over the guidewire of FIG. 61 to dilate the native valve.
Figure 61:
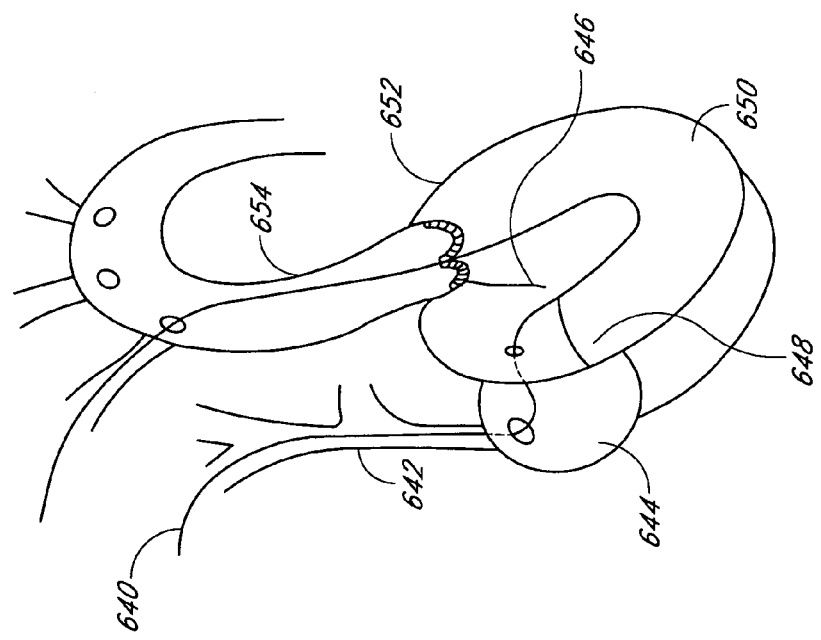
FIG. 61 is a schematic view of one embodiment of the implantation procedure for the prosthetic valve where the distal end of a transseptally placed guidewire has been externalized from the arterial circulation.
Figure 64:
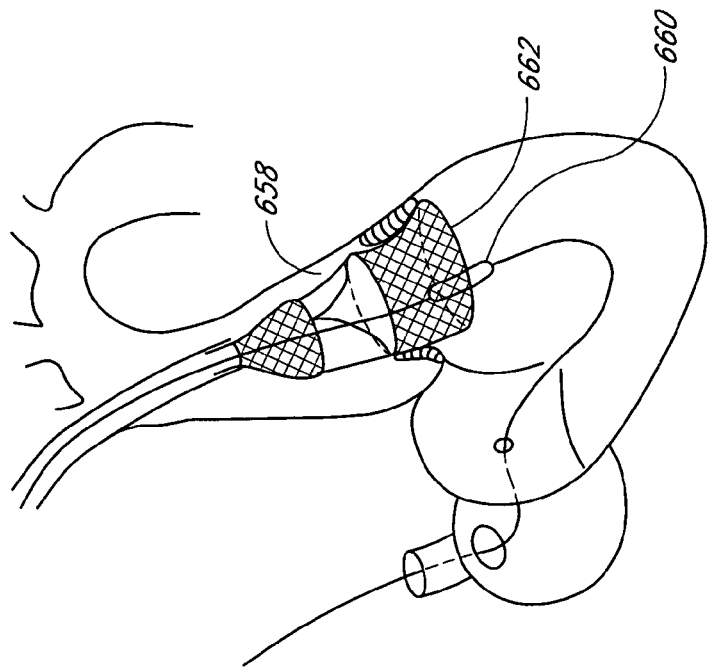
FIG. 64 is a schematic view showing a balloon catheter passed over the guidewire of FIG. 63 from a venous approach and placed opposite the stented native valve for additional ablation and/or securing of the lower portion of the stent.
Figure 63:
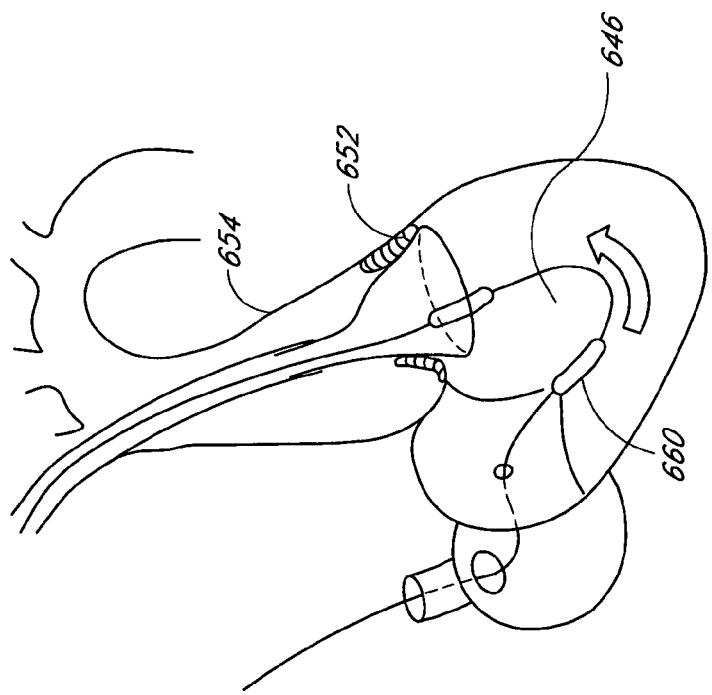
FIG. 63 is a schematic view showing the deployment of a prosthetic valve by an arterial approach over the guidewire of FIG. 62.
Figure 65:
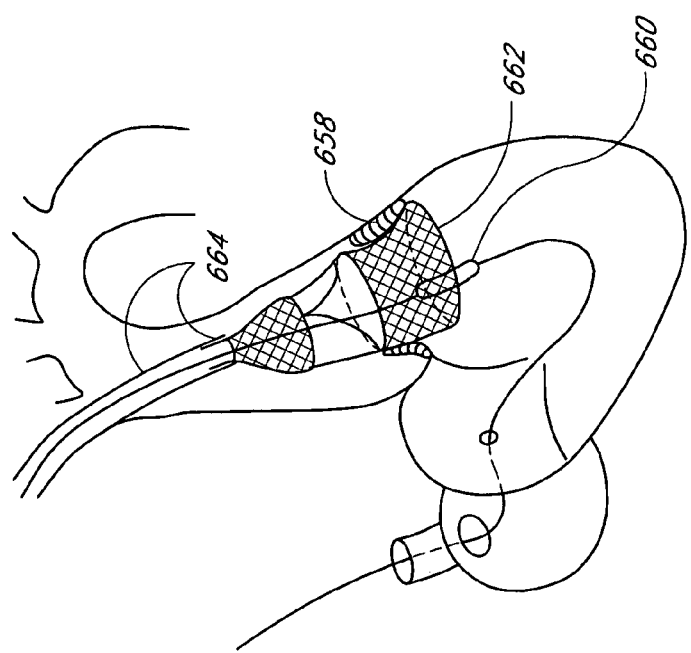
FIG. 65 is a schematic view showing how the stent of FIG. 64 remains attached to the delivery system by braces to allow full positioning of the stent.

Referring to FIG. 61, a method for deploying the preferred embodiment of the invention using the separate stent is provided. The method of deployment comprises a guidewire 640 inserted via a venous approach 642 and passed from the right 644 to left atrium 646 through a known transseptal approach, herein incorporated by reference. After transseptal puncture, guidewire 640 is further directed from left atrium 646 past the mitral valve 648 to the left ventricle 650 and through the aortic valve 652. An introducer (not shown) is inserted via an arterial approach and a snare (not shown), such as the Amplatz GOOSE NECK® snare (Microvena, Minn.), is inserted through the introducer to grasp the distal end of guidewire 640 and externalize guidewire 640 out of the body through the introducer. With both ends of guidewire 640 external to the body, access to the implantation site is available from both the venous 642 and arterial approaches 654. In FIG. 62, aortic valve 652 is pre-dilated by a balloon catheter 656 using a well-known valvuloplasty procedure, herein incorporated by reference. The prosthesis is then implanted as previously described by passing the delivery system from either the venous or arterial approaches. As illustrated in FIG. 63, the prosthesis 658 may be implanted using arterial approach 654 with prosthetic valve 658 implanted above the level of native valve 652. As shown in FIG. 64, a balloon catheter 660 may be passed by venous approach 642 for further displacement of native valve 652 and/or to further secure the lower stent 662 to the annulus. Hooks 664, shown in FIG. 65, connecting the delivery catheter to prosthetic valve 658 allow full control of prosthetic valve 658 positioning until the operator chooses to fully release and implant prosthetic valve 658. A separate stent may then be implanted by venous approach 642 at the valvular ring to further push back the native valve or valve remnants and reduce recoil forces from these structures. Passing balloon 660 by the venous approach 642 avoids interference with superiorly located prosthetic valve 658. Implantation of replacement valve 658 by arterial approach 654 prior to the ablation of the native valve 652 or valve remnants by venous approach 642 may reduce the risks associated with massive aortic regurgitation when native valve 652 is pushed back prior to implantation of replacement valve 658. Reducing the risks of massive aortic regurgitation may provide the operator with additional time to position replacement valve 658.

It is further contemplated that in the preferred embodiment of the invention, valve assembly 310 also comprises a drug-eluting component well known in the art and herein incorporated by reference. The drug-eluting component may be a surface coating or a matrix system bonded to various portions of valve assembly 310, including but not limited to central support band 314, anchors 316 318, valve 312, loop elements 352 or wires 342. The surface coating or matrix system may have a diffusion-type, erosive-type or reservoir-based drug release mechanism. Drugs comprising the drug-eluting component may include antibiotics, cellular anti-proliferative and/or anti-thrombogenic drugs. Drugs, as used herein, include but are not limited to any type of biologically therapeutic molecule. Particular drugs may include but are not limited to actinomycin-D, batimistat, c-myc antisense, dexamethasone, heparin, paclitaxel, taxanes, sirolimus, tacrolimus and everolimus.

Figures 50, 51, 52:
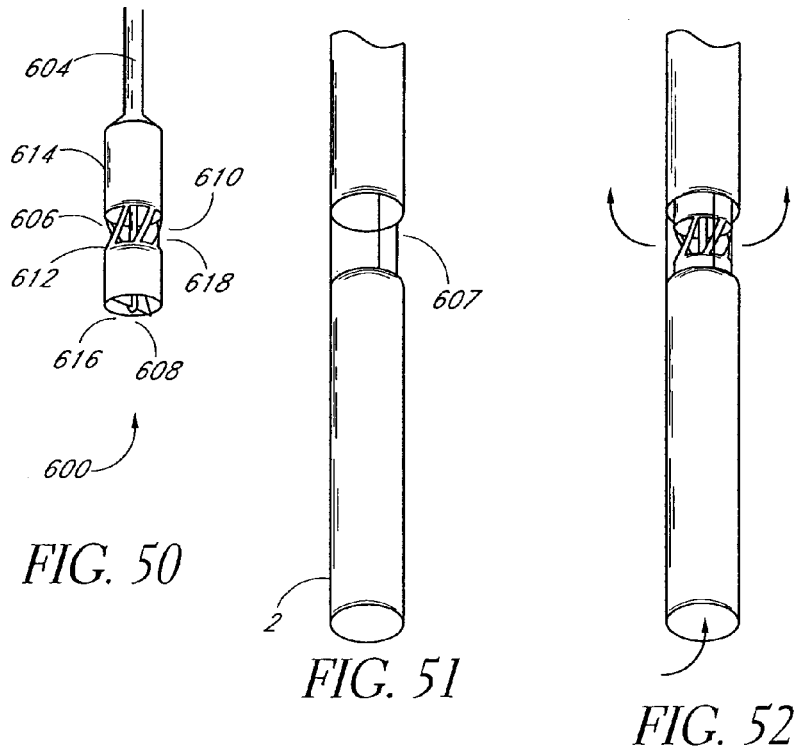
FIG. 50 is side view of an impeller and impeller housing of one embodiment of the blood pump.
FIG. 51 is a side view of a catheter with catheter openings that allow blood flow by the impeller.
FIG. 52 is a side view of the catheter with the impeller in place and blood flow depicted by arrows.

As previously mentioned, one embodiment of the system for implanting the prosthesis and/or excising the native valve leaflets contemplates maintaining blood flow across the native valve site during the excision and implantation procedure. By maintaining blood flow across the native valve, use of extracorporeal circulation or peripheral aorto-venous heart assistance and their side effects may be reduced or avoided. Major side effects of extracorporeal circulation and peripheral aorto-venous heart assistance include neurological deficits, increased bleeding and massive air emboli. FIGS. 50 through 52 depict one embodiment of the invention for maintaining blood perfusion during the procedure. This embodiment comprises a blood pump 600 and an opening 602 positioned in the wall of tubular catheter 2 of the excision system. When the tubular catheter 2 is positioned at the excision site, blood pump 600 allows continued blood flow across the excision site that would otherwise be interrupted during the excision procedure. Blood pump 600 may comprise a motor, a shaft and an impeller. Blood pump 600 is insertable through passage 15 of tubular catheter 2. The motor is connected to a shaft 604 that in turn is coupled to an impeller 606. The motor is capable of rotating shaft 604, resulting in the rotation of impeller 606. Impeller 606 comprises a proximal end 608, a distal end 610 and a plurality of fins 612 angled along the longitudinal axis of impeller 606, such that when impeller 606 is rotated in one direction, fins 612 are capable of moving blood from a proximal to distal direction. When impeller 606 is rotated in the other direction, fins 612 are capable of moving blood in a distal to proximal direction. The ability to rotate impeller 606 in either direction allows but is not limited to the use of the blood pump in both anterograde and retrograde approaches to a heart valve. The blood pump is positioned generally about catheter opening 602. The blood pump has an external diameter of about 4-mm and the passage of the catheter has a 4-mm internal diameter. Catheter opening 602 has a longitudinal length of about 4-mm. Catheter opening 602 may comprise a plurality of openings located along a circumference of tubular catheter 2. To reduce interruption of blood flow through tubular catheter 2 during the implantation portion of the procedure, catheter opening 602 should preferably be about 30 mm from the tip of catheter 2 or distal to the bell housing 6a. This positioning of catheter opening 602 reduces the risk of occlusion of catheter opening 602 by the replacement valve.

FIG. 50 depicts an optional feature of blood pump 600 further comprising an impeller housing 614 having at least one proximal housing opening 616 and at least one distal housing opening 618. Housing 614 protects passage 15 of tubular catheter 2 from potential damage by rotating impeller 600. Proximal 616 and distal housing openings 618 provide inflow and outflow of blood from the impeller, depending on the rotation direction of impeller 600.

To reduce interruption of blood flow through catheter 2 during the implantation portion of the procedure, catheter opening 602 should preferably be at least a distance of about 30 mm from the distal tip of the catheter or about distal to the bell housing 6a to avoid occlusion of catheter opening 602 by the replacement valve.

Figures 53, 54:
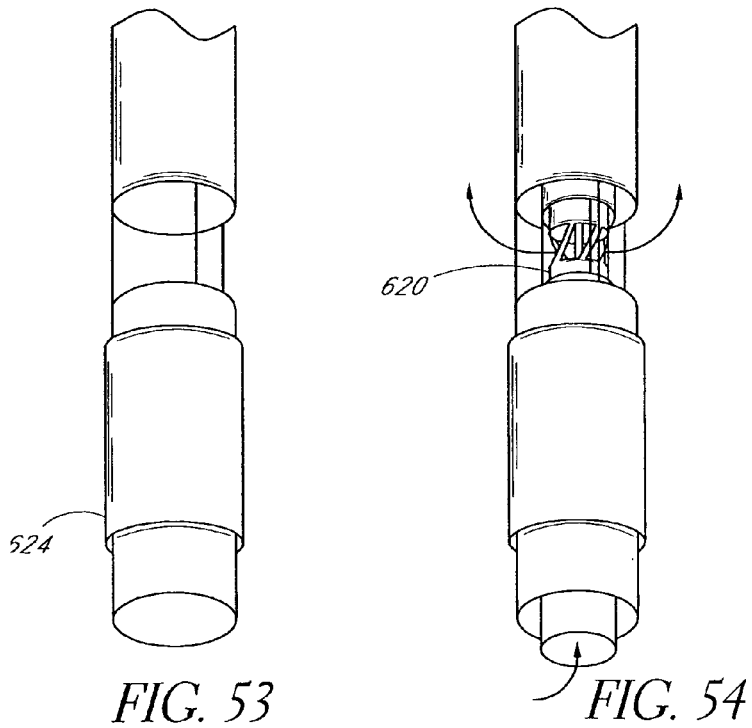
FIG. 53 depicts another embodiment of the invention with a separate blood pump catheter relative to the prosthesis delivery system.
FIG. 54 illustrates the embodiment shown in FIG. 16 with the blood pump in place and blood flow shown by arrows.

FIGS. 53 and 54 depict an alternative embodiment, where blood pump 620 is located in a second catheter 622 in the prosthesis delivery system. Once blood pump 620 and second catheter 622 are in position, the prosthesis delivery system 624 is slid over the separate catheter 622 to position the prosthesis for implantation, while avoiding blockage of blood flow in separate catheter 622. In this embodiment, the diameter of the delivery system is preferably about 8 mm.

Figure 66:
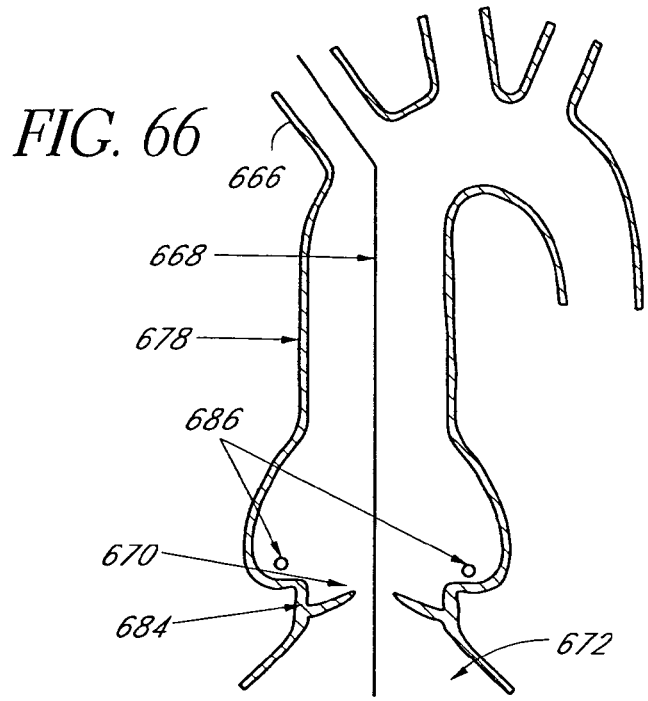
FIG. 66 depicts a schematic view of another embodiment of the implantation procedure for the prosthetic valve where a guidewire is inserted into the axillary artery and passed to the left ventricle.
Figure 67:
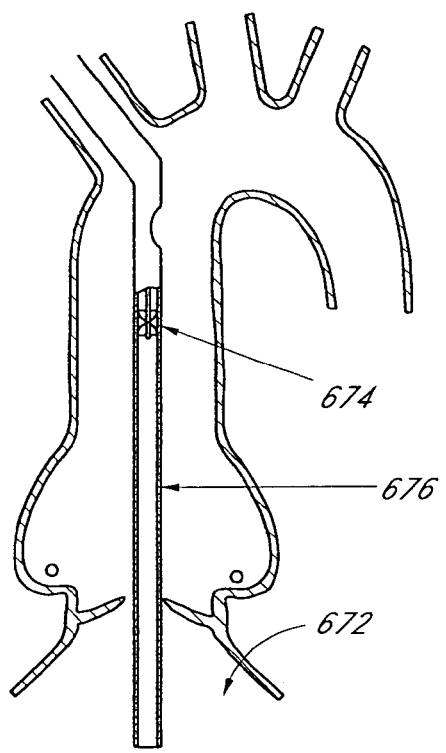
FIG. 67 depicts a schematic view of a blood pump passed over the guidewire of FIG. 66.
Figure 68:
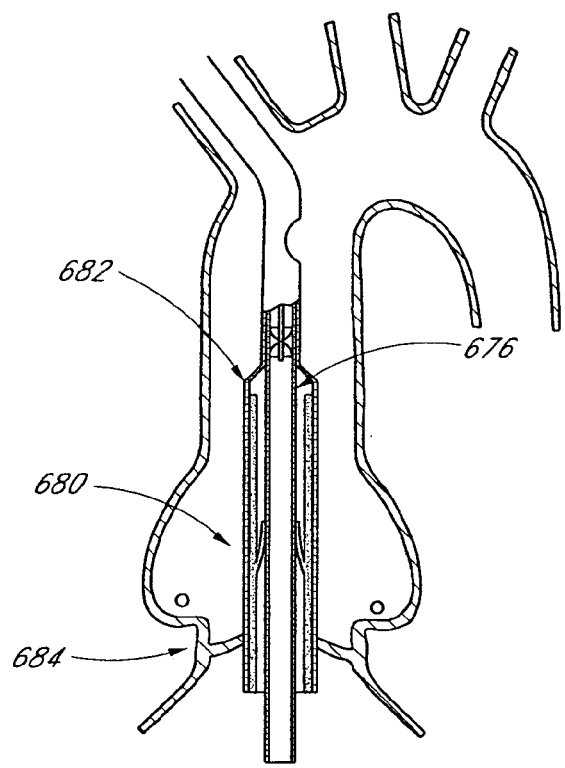
FIG. 68 depicts a schematic view of a valve prosthesis passed over the blood pump of FIG. 67.
Figure 69:
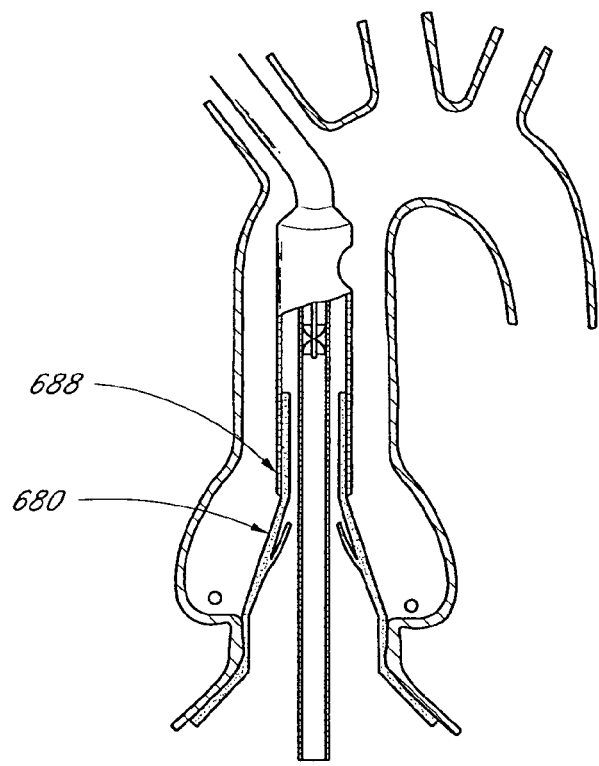
FIGS. 69 and 70 depict schematic views of the deployment and attachment of the prosthesis of FIG. 68 to the vessel wall.
Figure 70:
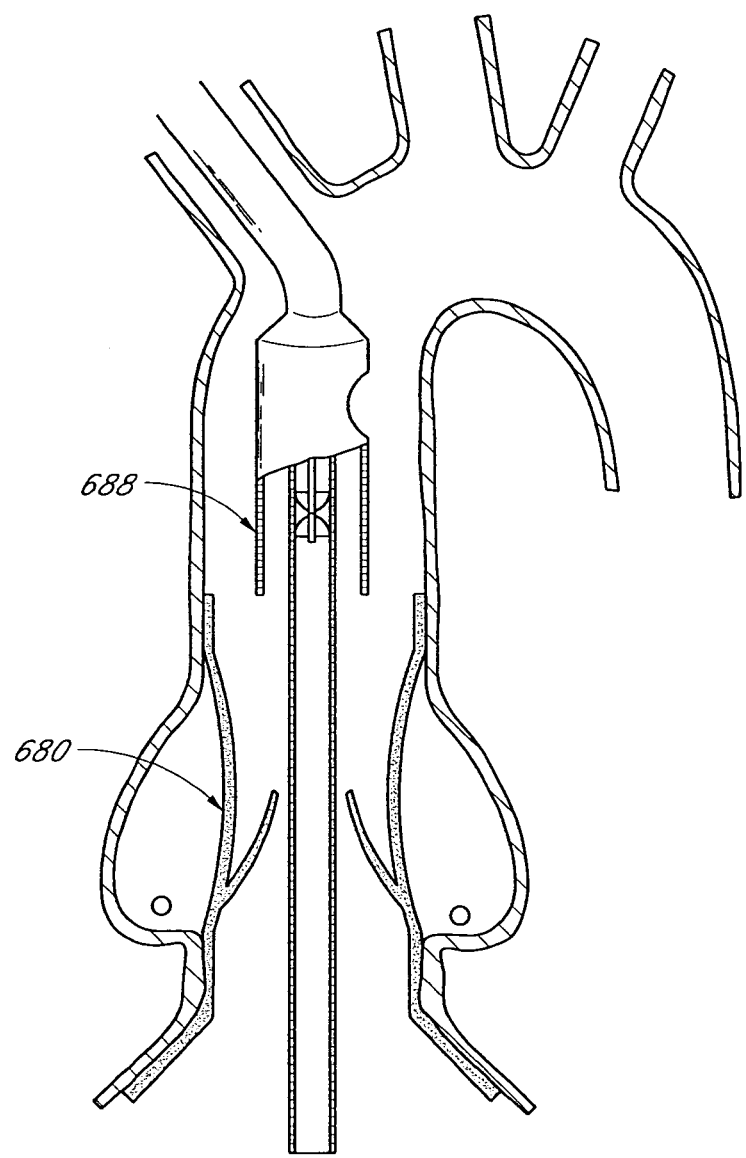

One method of using the blood flow pump during the implantation of the prosthesis is now described. This procedure may be performed under fluoroscopy and/or transesophageal echocardiography. FIG. 66 shows vascular access made through the axillary artery 666. A guidewire 668 is inserted past the aortic valve 670 and into the left ventricle 672. In FIG. 67, a blood pump 674 is inserted into a hollow catheter passed 676 over guidewire 668 inside the aorta 678 and pushed into left ventricle 672. Blood pump 674 is started to ensure a steady and sufficient blood flow of about 2.5 L/min from left ventricle 672 downstream during the valve replacement. FIG. 68 depicts valve prosthesis 680, retained on the delivery system 682 and positioned by sliding over blood pump catheter 676. Prosthesis 680 is positioned generally about the valve annulus 684 and the coronary ostia 686, with the assistance of radiographic markers. As shown in FIGS. 69 and 70, the sheath 688 overlying prosthesis 680 is pulled back and prosthesis 680 is deployed as previously described Catheter hooks 690 connecting the delivery catheter to the prosthetic valve allow full control of prosthetic valve positioning until the operator chooses to fully release and implant the prosthetic valve. Optional anchoring hooks, described previously, may be deployed generally about he annulus, the ventricle and the ascending aorta. Deployment of the anchoring hooks may be enhanced by radial expansion of a balloon catheter that further engages the hooks into the surrounding structures. Blood pump 674 is stopped and blood pump catheter 676 is removed. Other configurations may be adapted for replacing a valve at other site will be familiar to those skilled in the art.

The present invention may be embodied in other specific forms without departing from its spirit or essential characteristics. The described embodiments are to be considered in all respects only as illustrative, and not restrictive and the scope of the invention is, therefore, indicated by the appended claims rather than by the foregoing description. For all of the embodiments described above, the steps of the methods need not be performed sequentially. All changes that come within the meaning and range of equivalency of the claims are to be embraced within their scope.

What is claimed is:

1. A prosthetic cardiac valve assembly comprising:
 a) a replacement valve comprising:
  a plurality of leaflets configured to permit blood to selectively flow therethrough; and
  a plurality of commissure points from which the replacement valve is suspended;
 b) a valve support connected to the replacement valve and configured to be collapsible for trans luminal delivery,
  said valve support having an axial length sufficient to extend, when implanted, from a position of a native annulus, past the replacement valve, past the commissure points, and past the patient's coronary ostia, and into an ascending aorta;
  wherein outer circumference of the valve support varies along at least some portions of the axial length;

wherein the valve support further comprises:
a first section terminating in a first end, said first end comprising an outer circumference having a first diameter, said first section configured to engage the native annulus; and
a second section terminating in a second end, said second end comprising an outer circumference having a second diameter, said second section configured to extend past the coronary ostia and into the ascending aorta,
wherein the second circumference is greater than the first circumference.

2. The prosthetic cardiac valve assembly of claim 1, wherein said first section comprises a plurality of intersecting members forming a plurality of cells, said cells having a first cross-sectional size and arranged substantially uniformly around a periphery of the valve support;
wherein the second section comprises a plurality of intersecting members forming a plurality of cells, said cells having a second cross-sectional size and arranged substantially uniformly around a periphery of the valve support; and
wherein the second cross-sectional size is greater than the first cross-sectional size.

3. The prosthetic cardiac valve assembly of claim 2, wherein the cells at the first and second sections comprise a diamond shape.

4. The prosthetic cardiac valve assembly of claim 1, wherein the valve support is self-expanding.

5. The prosthetic cardiac valve assembly of claim 1, wherein the valve support comprises a plurality of wires.

6. The prosthetic cardiac valve assembly of claim 1, wherein the valve support comprises a shape memory material.

7. The prosthetic cardiac valve assembly of claim 6, wherein the shape memory material comprises Nitinol.

8. The prosthetic cardiac valve assembly of claim 1, wherein the replacement valve is secured to the valve support using at least one suture.

9. The prosthetic cardiac valve assembly of claim 1, wherein the replacement valve comprises at least three leaflets.

10. The prosthetic cardiac valve assembly of claim 1, wherein at least a portion of the valve support is configured to apply a radial expansion force up to a predetermined diameter.

11. A prosthetic cardiac valve assembly comprising:
a replacement valve comprising a plurality of leaflets and a plurality of commissure points from which the replacement valve is generally suspended; and
a valve support having a proximal portion and a distal portion, said valve support connected to the replacement valve and configured to be collapsible for trans luminal delivery;
wherein the valve support is configured to extend, when implanted into a patient, from a native annulus at the proximal portion to an ascending aorta at the distal portion, past a location of the patient's coronary ostia;
wherein an outer shape of the valve support varies along an axial length of said valve support such that a cross-sectional dimension of the distal portion is generally larger than a cross-sectional dimension of the proximal portion;
wherein the valve support comprises a plurality of intersecting members forming a plurality of cells, said cells being arranged substantially uniformly around a periphery of the valve support; and
wherein the plurality of cells located along the distal portion of the valve support have a larger cross-sectional size than the plurality of cells located along the proximal portion of the valve support.

12. The prosthetic cardiac valve assembly of claim 11, wherein the valve support comprises a proximal end and a distal end, a cross-sectional dimension of said distal end being larger than a cross-sectional dimension of said proximal end.

13. The prosthetic cardiac valve assembly of claim 11, wherein the plurality of cells at the proximal and distal portions comprise a diamond shape.

14. The prosthetic cardiac valve assembly of claim 11, wherein the valve support is self-expanding.

15. The prosthetic cardiac valve assembly of claim 11, wherein the valve support comprises a plurality of wires.

16. The prosthetic cardiac valve assembly of claim 11, wherein the valve support comprises a shape memory material.

17. The prosthetic cardiac valve assembly of claim 16, wherein the shape memory material comprises Nitinol.

18. The prosthetic cardiac valve assembly of claim 11, wherein the replacement valve is secured to the valve support using at least one suture.

19. The prosthetic cardiac valve assembly of claim 11, wherein the replacement valve comprises at least three leaflets.

20. The prosthetic cardiac valve assembly of claim 11, wherein at least a portion of the valve support is configured to apply a radial expansion force up to a predetermined diameter.

21. A prosthetic cardiac valve comprising:
a) a replacement valve comprising:
a plurality of leaflets configured to permit blood to selectively flow therethrough; and
a plurality of commissure points from which the replacement valve is suspended; and
b) a valve support connected to the replacement valve and configured to be collapsible for transluminal delivery,
wherein, when the valve support is implanted in a patient and the replacement valve is positioned in a native aortic valve annulus, said valve support is sized and shaped to extend from a position of the native annulus, past the replacement valve, the commissure points, and the patient's coronary ostia, and into an ascending aorta;
wherein outer circumference of the valve support varies along at least some portions of the axial length;
wherein the valve support further comprises:
a first section terminating in a first end, said first end comprising an outer circumference having a first diameter, said first section configured to engage the native annulus; and
a second section terminating in a second end, said second end comprising an outer circumference having a second diameter, said second section configured to extend past the coronary ostia and into the ascending aorta,
wherein the second circumference is greater than the first circumference.

* * * * *

UNITED STATES PATENT AND TRADEMARK OFFICE
CERTIFICATE OF CORRECTION

PATENT NO. : 8,579,966 B2   Page 1 of 1
APPLICATION NO. : 10/772101
DATED : November 12, 2013
INVENTOR(S) : Jacques Seguin et al.

It is certified that error appears in the above-identified patent and that said Letters Patent is hereby corrected as shown below:

On the Title Page

Item (63) "Related U.S. Application Data":

"application No. 10/130,355, filed as" should be replaced with --application No. 10/130,355, filed on May 17, 2002 and having a § 371(c) date of November 26, 2002, filed as--

Item (30) "Foreign Application Priority Data" should be inserted:

--(30) Foreign Application Priority Data
Nov. 17, 1999 (FR) ............................. 99/14462
Oct. 31, 2000 (FR) ............................. 00/14028--

In the Specification

In column 1, line 8: "filed on Apr. 10, 2003, which is" should be replaced with
--filed on Apr. 10, 2003, now U.S. Patent No. 7,018,406, which is--

In column 1, lines 9-10: "filed on May 17, 2002, which is" should be replaced with --filed on May 17, 2002 and having a § 371(c) date of November 26, 2002, now U.S. Patent No. 6,830,584, which is--

Signed and Sealed this
Eleventh Day of March, 2014

Michelle K. Lee
*Deputy Director of the United States Patent and Trademark Office*